United States Patent
Milo et al.

(10) Patent No.: US 11,378,449 B2
(45) Date of Patent: Jul. 5, 2022

(54) ACCESSORIES FOR HANDHELD SPECTROMETER

(71) Applicant: Verifood, Ltd., Herzliya (IL)

(72) Inventors: Renan Milo, Rechovot (IL); Uri Kinrot, Hod HaSharon (IL); Liron Nunez Weissman, Rosh-Haayin (IL); Yaron Dycian, Kadima (IL)

(73) Assignee: VERIFOOD, LTD., Herzliya (IL)

( * ) Notice: Subject to any disclaimer, the term of this patent is extended or adjusted under 35 U.S.C. 154(b) by 0 days.

(21) Appl. No.: 16/251,509

(22) Filed: Jan. 18, 2019

(65) Prior Publication Data
US 2019/0285471 A1   Sep. 19, 2019

Related U.S. Application Data

(63) Continuation of application No. PCT/IL2017/050808, filed on Jul. 18, 2017.
(Continued)

(51) Int. Cl.
*G01J 3/02* (2006.01)
*G01J 3/10* (2006.01)
(Continued)

(52) U.S. Cl.
CPC ........ *G01J 3/0297* (2013.01); *A61B 1/00131* (2013.01); *A61B 1/07* (2013.01);
(Continued)

(58) Field of Classification Search
None
See application file for complete search history.

(56) References Cited

U.S. PATENT DOCUMENTS

| | | |
|---|---|---|
| 679,577 A | 7/1901 | Henry |
| 5,305,077 A | 4/1994 | Grego et al. |

(Continued)

FOREIGN PATENT DOCUMENTS

| | | |
|---|---|---|
| CN | 1437702 A | 8/2003 |
| CN | 1846114 A | 10/2006 |

(Continued)

OTHER PUBLICATIONS

Acktar Advanced Coatings Website. Accessed Jun. 3, 2015. http://www.acktar.com/.
(Continued)

*Primary Examiner* — Matthew D Krcha
*Assistant Examiner* — Brittany I Fisher
(74) *Attorney, Agent, or Firm* — Wilson Sonsini Goodrich & Rosati

(57) ABSTRACT

A handheld spectrometer apparatus may comprise an accessory coupled to a spectrometer, where the accessory is configured to receive a liquid sample pipette to facilitate measurement, using the spectrometer, of a liquid sample within the pipette. A handheld spectrometer apparatus to measure a body lumen of a subject can include an illumination unit, a spectrometer unit, a housing containing the illumination unit and the spectrometer unit and an accessory comprising a plurality of optical fibers. The optical fibers can be configured to guide light from the illumination unit to the body lumen and back from the body lumen to the spectrometer unit.

8 Claims, 47 Drawing Sheets
(8 of 47 Drawing Sheet(s) Filed in Color)

Related U.S. Application Data

(60) Provisional application No. 62/504,579, filed on May 11, 2017, provisional application No. 62/364,331, filed on Jul. 20, 2016.

(51) Int. Cl.

| | |
|---|---|
| *G01N 21/27* | (2006.01) |
| *G01N 21/31* | (2006.01) |
| *G01N 21/3577* | (2014.01) |
| *G01J 3/50* | (2006.01) |
| *B01L 3/02* | (2006.01) |
| *A61B 1/227* | (2006.01) |
| *A61B 1/00* | (2006.01) |
| *A61B 5/00* | (2006.01) |
| *A61B 1/07* | (2006.01) |
| *A61B 5/1495* | (2006.01) |
| *G01J 3/12* | (2006.01) |
| *G01N 21/65* | (2006.01) |
| *G01N 21/64* | (2006.01) |

(52) U.S. Cl.
CPC ............ *A61B 1/227* (2013.01); *A61B 5/0075* (2013.01); *A61B 5/1495* (2013.01); *B01L 3/0217* (2013.01); *G01J 3/0202* (2013.01); *G01J 3/0205* (2013.01); *G01J 3/0218* (2013.01); *G01J 3/0256* (2013.01); *G01J 3/0264* (2013.01); *G01J 3/0272* (2013.01); *G01J 3/0286* (2013.01); *G01J 3/0289* (2013.01); *G01J 3/0291* (2013.01); *G01J 3/10* (2013.01); *G01J 3/50* (2013.01); *G01N 21/274* (2013.01); *G01N 21/31* (2013.01); *G01N 21/3577* (2013.01); *A61B 2560/0223* (2013.01); *A61B 2562/0233* (2013.01); *G01J 2003/1221* (2013.01); *G01N 21/65* (2013.01); *G01N 2021/6417* (2013.01); *G01N 2201/0221* (2013.01)

(56) References Cited

U.S. PATENT DOCUMENTS

| | | | |
|---|---|---|---|
| 5,469,252 | A | 11/1995 | Doles et al. |
| 5,966,212 | A | 10/1999 | Hendler et al. |
| 6,031,233 | A | 2/2000 | Levin et al. |
| 6,031,619 | A | 2/2000 | Wilkens et al. |
| 6,069,696 | A | 5/2000 | McQueen et al. |
| 6,072,576 | A | 6/2000 | McDonald et al. |
| 6,119,031 | A | 9/2000 | Crowley |
| 6,212,312 | B1 | 4/2001 | Grann et al. |
| 6,324,418 | B1 | 11/2001 | Crowley et al. |
| 6,333,501 | B1 | 12/2001 | Labrenz |
| 6,383,209 | B1 * | 5/2002 | Crowley ............ A61B 1/00142 600/121 |
| 6,437,345 | B1 | 8/2002 | Bruno-Raimondi et al. |
| 6,441,375 | B1 | 8/2002 | Joseph et al. |
| 6,456,373 | B1 | 9/2002 | Wienecke et al. |
| 6,483,583 | B1 | 11/2002 | Wright et al. |
| 6,615,142 | B1 | 9/2003 | Hovde |
| 6,639,666 | B2 | 10/2003 | Li |
| 6,700,661 | B1 | 3/2004 | Cadell et al. |
| 6,717,669 | B2 | 4/2004 | Ruiz |
| 6,836,325 | B2 | 12/2004 | Maczura et al. |
| 6,864,978 | B1 | 3/2005 | Hazen et al. |
| 6,958,479 | B2 | 10/2005 | Burling-Claridge et al. |
| 7,009,702 | B2 | 3/2006 | Caruso et al. |
| 7,038,774 | B2 | 5/2006 | Hazen et al. |
| 7,068,366 | B2 | 6/2006 | Burk et al. |
| 7,075,643 | B2 | 7/2006 | Holub |
| 7,084,974 | B1 | 8/2006 | Barwicz et al. |
| 7,145,650 | B2 | 12/2006 | Wang et al. |
| 7,151,600 | B2 | 12/2006 | Imura |
| 7,158,225 | B2 | 1/2007 | Tedesco et al. |
| 7,235,766 | B2 | 6/2007 | Shur et al. |
| 7,236,243 | B2 | 6/2007 | Beecroft et al. |
| 7,245,372 | B2 | 7/2007 | Han |
| 7,248,370 | B2 | 7/2007 | Jones |
| 7,251,037 | B2 | 7/2007 | Jones |
| 7,262,839 | B2 | 8/2007 | Treado et al. |
| 7,286,233 | B2 | 10/2007 | Pizzi |
| 7,339,665 | B2 | 3/2008 | Imura |
| 7,414,724 | B2 | 8/2008 | Eckert et al. |
| 7,420,663 | B2 | 9/2008 | Wang et al. |
| 7,426,446 | B2 | 9/2008 | Hagler |
| 7,433,042 | B1 | 10/2008 | Cavanaugh et al. |
| 7,436,511 | B2 | 10/2008 | Ruchti et al. |
| 7,489,396 | B1 | 2/2009 | Vrhel et al. |
| 7,528,957 | B2 | 5/2009 | Lewis et al. |
| 7,535,617 | B2 | 5/2009 | Gupta et al. |
| 7,649,627 | B2 | 1/2010 | Yamamoto |
| 7,667,740 | B2 | 2/2010 | Hofer |
| 7,697,136 | B2 | 4/2010 | Imura |
| 7,767,969 | B2 | 8/2010 | Nagai et al. |
| 7,805,319 | B2 | 9/2010 | Badinelli |
| 7,817,273 | B2 | 10/2010 | Bahatt et al. |
| 7,868,296 | B2 | 1/2011 | Haran et al. |
| 7,876,435 | B2 | 1/2011 | Becker-Ross et al. |
| 7,881,892 | B2 | 2/2011 | Soyemi et al. |
| 7,897,923 | B2 | 3/2011 | Shelley et al. |
| 7,907,282 | B2 | 3/2011 | Coates |
| 7,929,130 | B2 | 4/2011 | Dirk |
| 7,986,193 | B2 | 7/2011 | Krah |
| 7,999,933 | B2 | 8/2011 | McClure |
| 8,027,041 | B1 | 9/2011 | Mitchell et al. |
| 8,060,383 | B2 | 11/2011 | Badinelli |
| 8,125,633 | B2 | 2/2012 | Whelan et al. |
| 8,144,322 | B2 | 3/2012 | Nagashima et al. |
| 8,149,415 | B2 | 4/2012 | Sanders et al. |
| 8,169,607 | B2 | 5/2012 | Sano et al. |
| 8,169,608 | B2 | 5/2012 | Sano et al. |
| 8,247,774 | B2 | 8/2012 | Chou et al. |
| 8,269,174 | B2 | 9/2012 | Gardner, Jr. et al. |
| 8,274,739 | B2 | 9/2012 | Lee et al. |
| 8,284,401 | B2 | 10/2012 | Choi et al. |
| 8,330,945 | B2 | 12/2012 | Choi et al. |
| 8,462,420 | B2 | 6/2013 | Lee et al. |
| 8,477,305 | B2 | 7/2013 | Shibayama et al. |
| 8,526,002 | B2 | 9/2013 | Deflores et al. |
| 8,542,359 | B2 | 9/2013 | Choi et al. |
| 8,593,628 | B2 | 11/2013 | Shimbo et al. |
| 8,604,412 | B2 | 12/2013 | Shibayama et al. |
| 8,654,327 | B2 | 2/2014 | Bohle et al. |
| 8,665,440 | B1 | 3/2014 | Kompaniets et al. |
| 8,675,188 | B2 | 3/2014 | Liu et al. |
| 8,711,360 | B2 | 4/2014 | Funamoto |
| 8,711,362 | B2 | 4/2014 | Funamoto |
| 8,735,820 | B2 | 5/2014 | Mertens |
| 8,742,320 | B2 | 6/2014 | Shibayama et al. |
| 8,760,645 | B2 | 6/2014 | Misener et al. |
| 8,773,659 | B2 | 7/2014 | McClure |
| 8,786,854 | B2 | 7/2014 | Miyazono |
| 8,848,187 | B2 | 9/2014 | Uematsu et al. |
| 8,862,445 | B2 | 10/2014 | Priore et al. |
| 8,867,033 | B2 | 10/2014 | Carron et al. |
| 8,868,387 | B2 | 10/2014 | Den et al. |
| 8,873,046 | B2 | 10/2014 | Miyazono |
| 8,937,717 | B2 | 1/2015 | Preston et al. |
| 8,976,357 | B2 | 3/2015 | Uematsu et al. |
| 9,030,662 | B2 | 5/2015 | Lee et al. |
| 9,060,113 | B2 | 6/2015 | Rhoads et al. |
| 9,063,011 | B2 | 6/2015 | Chen et al. |
| 9,074,933 | B2 | 7/2015 | Yokino et al. |
| 9,128,055 | B2 | 9/2015 | Sekino et al. |
| 9,163,986 | B2 | 10/2015 | Bouckaert |
| 9,173,508 | B2 | 11/2015 | Tornwall et al. |
| 9,182,280 | B1 | 11/2015 | Gardner et al. |
| 9,234,800 | B2 | 1/2016 | Kawamata et al. |
| 9,239,264 | B1 | 1/2016 | Demers |
| D750,988 | S | 3/2016 | Goldring |
| D751,435 | S | 3/2016 | Goldring |
| 9,291,504 | B2 | 3/2016 | Goldring et al. |
| 9,297,821 | B2 | 3/2016 | Walter et al. |

(56) References Cited

U.S. PATENT DOCUMENTS

| | | |
|---|---|---|
| 9,301,626 B2 | 4/2016 | Tornwall et al. |
| 9,310,564 B2 | 4/2016 | Martinelli et al. |
| 9,377,396 B2 | 6/2016 | Goldring et al. |
| 9,383,258 B2 | 7/2016 | Goldring et al. |
| 9,383,308 B2 | 7/2016 | Bradley et al. |
| 9,395,244 B2 | 7/2016 | Kurokawa et al. |
| 9,417,180 B2 | 8/2016 | Seo et al. |
| 9,448,114 B2 | 9/2016 | Goldring et al. |
| 9,448,165 B2 | 9/2016 | Gulati et al. |
| 9,453,794 B2 | 9/2016 | Gulati et al. |
| 9,464,934 B2 | 10/2016 | Priore et al. |
| 9,488,468 B2 | 11/2016 | Tsujii et al. |
| 9,488,523 B2 | 11/2016 | Yokino et al. |
| 9,500,523 B2 | 11/2016 | Goldring et al. |
| 9,508,765 B2 | 11/2016 | Owa et al. |
| 9,518,917 B2 | 12/2016 | Scherer et al. |
| 9,546,902 B2 | 1/2017 | Kovacich et al. |
| 9,546,904 B2 | 1/2017 | Pawluczyk et al. |
| 9,557,220 B2 | 1/2017 | Yasui et al. |
| 9,562,848 B2 | 2/2017 | Goldring et al. |
| 9,568,363 B2 | 2/2017 | Yu et al. |
| 9,574,942 B2 | 2/2017 | Goldring et al. |
| 9,587,982 B2 | 3/2017 | Goldring et al. |
| 9,933,305 B2 | 4/2018 | Goldring et al. |
| 9,952,098 B2 | 4/2018 | Goldring et al. |
| 10,203,246 B2 | 2/2019 | Rosen et al. |
| 10,254,215 B2 | 4/2019 | Wilk et al. |
| 10,323,982 B2 | 6/2019 | Goldring et al. |
| 10,330,531 B2 | 6/2019 | Goldring et al. |
| 10,502,679 B2 | 12/2019 | Aphek |
| 2001/0009972 A1 | 7/2001 | Doi et al. |
| 2001/0028648 A1 | 10/2001 | Suzuki |
| 2002/0039186 A1 | 4/2002 | Rosenberg et al. |
| 2002/0131044 A1 | 9/2002 | Kobayashi et al. |
| 2002/0131047 A1 | 9/2002 | Zarrabian et al. |
| 2002/0145728 A1 | 10/2002 | Adams et al. |
| 2002/0163641 A1 | 11/2002 | Shroder |
| 2002/0191127 A1 | 12/2002 | Roberts et al. |
| 2002/0193671 A1 | 12/2002 | Ciurczak et al. |
| 2003/0122080 A1 | 7/2003 | Burling-Claridge et al. |
| 2004/0019462 A1 | 1/2004 | Gehrlein et al. |
| 2004/0136577 A1 | 7/2004 | Rao et al. |
| 2004/0213459 A1 | 10/2004 | Ishimaru et al. |
| 2005/0037505 A1 | 2/2005 | Samsoondar |
| 2005/0117151 A1 | 6/2005 | Han |
| 2005/0128477 A1 | 6/2005 | Caruso et al. |
| 2005/0149598 A1 | 7/2005 | Mendlovic et al. |
| 2005/0151975 A1 | 7/2005 | Melnyk |
| 2005/0196046 A1 | 9/2005 | Hudnut et al. |
| 2006/0086901 A1 | 4/2006 | Price et al. |
| 2006/0124656 A1 | 6/2006 | Popovich, Jr. et al. |
| 2006/0132760 A1 | 6/2006 | Imura |
| 2006/0146315 A1 | 7/2006 | Treado |
| 2006/0279732 A1 | 12/2006 | Wang et al. |
| 2006/0280096 A1 | 12/2006 | Riley et al. |
| 2007/0084990 A1* | 4/2007 | Coates .................. G01J 3/0272 250/226 |
| 2007/0230932 A1 | 10/2007 | Tanaka et al. |
| 2007/0236697 A1 | 10/2007 | Zribi et al. |
| 2008/0061236 A1 | 3/2008 | Meredith et al. |
| 2008/0073510 A1 | 3/2008 | Finlay |
| 2008/0112853 A1 | 5/2008 | Hall |
| 2008/0137328 A1 | 6/2008 | Lee et al. |
| 2008/0204578 A1 | 8/2008 | Scheuch et al. |
| 2008/0265146 A1 | 10/2008 | Coates |
| 2008/0277625 A1 | 11/2008 | Nakamura et al. |
| 2008/0297379 A1 | 12/2008 | Yang et al. |
| 2008/0297791 A1 | 12/2008 | Imura |
| 2009/0051910 A1 | 2/2009 | Imura |
| 2009/0201577 A1 | 8/2009 | LaPlante et al. |
| 2009/0213361 A1 | 8/2009 | Vander et al. |
| 2009/0294637 A1 | 12/2009 | Kusano et al. |
| 2010/0045616 A1 | 2/2010 | Li et al. |
| 2010/0080351 A1 | 4/2010 | Hession-Kunz et al. |
| 2010/0085537 A1 | 4/2010 | Ramella-Roman et al. |
| 2010/0110442 A1 | 5/2010 | Adibi et al. |
| 2010/0128370 A1 | 5/2010 | Chen et al. |
| 2010/0132484 A1* | 6/2010 | Schacher ............ G01N 35/1002 73/863.01 |
| 2010/0134794 A1 | 6/2010 | Odegard et al. |
| 2010/0165337 A1 | 7/2010 | Dirk |
| 2010/0191493 A1 | 7/2010 | Brown et al. |
| 2010/0201979 A1 | 8/2010 | Momtahan et al. |
| 2010/0271352 A1 | 10/2010 | Nakano et al. |
| 2010/0284005 A1 | 11/2010 | Malinen et al. |
| 2010/0292581 A1 | 11/2010 | Howard et al. |
| 2010/0309454 A1 | 12/2010 | Zhang |
| 2011/0037975 A1 | 2/2011 | McClure |
| 2011/0255745 A1 | 10/2011 | Hodder et al. |
| 2011/0261252 A1 | 10/2011 | Chen |
| 2011/0318717 A1 | 12/2011 | Adamowicz |
| 2012/0001083 A1 | 1/2012 | Knapp |
| 2012/0018829 A1 | 1/2012 | Beck et al. |
| 2012/0019819 A1 | 1/2012 | Messerchmidt |
| 2012/0053426 A1 | 3/2012 | Webster et al. |
| 2012/0088486 A1 | 4/2012 | Messerchmidt |
| 2012/0099102 A1 | 4/2012 | Bello |
| 2012/0286046 A1 | 11/2012 | Ciurczak et al. |
| 2013/0021611 A1 | 1/2013 | Tsurutani |
| 2013/0107260 A1 | 5/2013 | Nozawa |
| 2013/0155402 A1 | 6/2013 | Walton et al. |
| 2013/0182250 A1 | 7/2013 | McClure |
| 2013/0258341 A1 | 10/2013 | Day et al. |
| 2014/0004548 A1* | 1/2014 | Gordon .................. G01N 21/94 435/21 |
| 2014/0046630 A1 | 2/2014 | Smith et al. |
| 2014/0052555 A1 | 2/2014 | MacIntosh |
| 2014/0064479 A1 | 3/2014 | Manikandan et al. |
| 2014/0168636 A1 | 6/2014 | Funamoto et al. |
| 2014/0293091 A1 | 10/2014 | Rhoads et al. |
| 2014/0320858 A1 | 10/2014 | Goldring et al. |
| 2014/0333932 A1 | 11/2014 | Uematsu et al. |
| 2015/0036138 A1 | 2/2015 | Watson et al. |
| 2015/0055132 A1 | 2/2015 | Ricketts et al. |
| 2015/0062577 A1 | 3/2015 | Hartwell et al. |
| 2015/0069239 A1 | 3/2015 | Kester et al. |
| 2015/0103354 A1 | 4/2015 | Saptari |
| 2015/0108333 A1 | 4/2015 | Bouckaert |
| 2015/0116707 A1 | 4/2015 | Tatsuda |
| 2015/0119661 A1 | 4/2015 | Gilbert et al. |
| 2015/0153225 A1 | 6/2015 | Baudelet |
| 2015/0204833 A1 | 7/2015 | O'Brien et al. |
| 2015/0300879 A1 | 10/2015 | Goldring et al. |
| 2015/0323383 A1 | 11/2015 | Pastore et al. |
| 2015/0369725 A1 | 12/2015 | Carvalho et al. |
| 2016/0018260 A1 | 1/2016 | Samuels |
| 2016/0033328 A1 | 2/2016 | Walters |
| 2016/0091369 A1 | 3/2016 | Sakurai et al. |
| 2016/0103069 A1 | 4/2016 | Umapathy et al. |
| 2016/0177366 A1 | 6/2016 | Auner et al. |
| 2016/0223400 A1 | 8/2016 | Carron et al. |
| 2016/0231171 A1 | 8/2016 | Assefa et al. |
| 2016/0238449 A1 | 8/2016 | Goldring et al. |
| 2016/0245700 A1 | 8/2016 | Uematsu et al. |
| 2016/0258813 A1 | 9/2016 | Kuri |
| 2016/0263910 A1 | 9/2016 | Kanai et al. |
| 2016/0282182 A1 | 9/2016 | Kanai et al. |
| 2016/0290863 A1 | 10/2016 | Goldring et al. |
| 2016/0299004 A1 | 10/2016 | Thamm |
| 2016/0299061 A1 | 10/2016 | Goldring et al. |
| 2016/0305820 A1 | 10/2016 | Zollars et al. |
| 2016/0313184 A1 | 10/2016 | Owechko |
| 2016/0334274 A1 | 11/2016 | Xu |
| 2016/0356646 A1 | 12/2016 | Wiegand et al. |
| 2016/0356647 A1 | 12/2016 | Wiegand et al. |
| 2016/0356704 A1 | 12/2016 | Kim et al. |
| 2017/0003167 A1 | 1/2017 | Ave |
| 2017/0010160 A1 | 1/2017 | Rosen et al. |
| 2017/0027447 A1 | 2/2017 | Sutin et al. |
| 2017/0038257 A1 | 2/2017 | Liu et al. |
| 2017/0160131 A1 | 6/2017 | Goldring et al. |
| 2017/0234729 A1 | 8/2017 | Goldring et al. |
| 2017/0309763 A1 | 10/2017 | Sweeney et al. |
| 2018/0003558 A1 | 1/2018 | Goldring et al. |

(56) References Cited

U.S. PATENT DOCUMENTS

| | | |
|---|---|---|
| 2018/0085003 A1 | 3/2018 | Goldring et al. |
| 2018/0120155 A1 | 5/2018 | Rosen et al. |
| 2018/0172510 A1 | 6/2018 | Rosen et al. |
| 2018/0180478 A1 | 6/2018 | Goldring et al. |
| 2018/0188110 A1 | 7/2018 | Goldring et al. |
| 2019/0011313 A1 | 1/2019 | Goldring et al. |
| 2019/0033130 A1 | 1/2019 | Goldring et al. |
| 2019/0033132 A1 | 1/2019 | Goldring et al. |
| 2019/0041265 A1 | 2/2019 | Rosen et al. |
| 2019/0056315 A1 | 2/2019 | Kinrot et al. |
| 2019/0310134 A1 | 10/2019 | Goldring et al. |
| 2020/0292385 A1 | 9/2020 | Goldring et al. |

FOREIGN PATENT DOCUMENTS

| | | |
|---|---|---|
| CN | 101501465 A | 8/2009 |
| CN | 102369421 A | 3/2012 |
| CN | 102435311 A | 5/2012 |
| CN | 102589700 A | 7/2012 |
| CN | 104777146 A | 7/2015 |
| DE | 10149879 A1 | 4/2003 |
| DE | 102012221527 A1 | 6/2014 |
| EP | 2783193 A1 | 10/2014 |
| EP | 3028020 A2 | 6/2016 |
| EP | 3090239 A2 | 11/2016 |
| JP | H0792022 A | 4/1995 |
| JP | 2001236583 A | 8/2001 |
| JP | 2002277326 A | 9/2002 |
| JP | 2004294361 A | 10/2004 |
| JP | 2005148018 A | 6/2005 |
| JP | 2007218878 A | 8/2007 |
| JP | 2008286522 A | 11/2008 |
| JP | 2009104547 A | 5/2009 |
| JP | 2011198801 A | 10/2011 |
| WO | WO-9953350 A1 | 10/1999 |
| WO | WO-2005008198 A2 | 1/2005 |
| WO | WO-2007064820 A2 | 6/2007 |
| WO | WO-2010027982 A2 | 3/2010 |
| WO | WO-2010036906 A1 | 4/2010 |
| WO | WO-2012040362 A2 | 3/2012 |
| WO | WO-2013065035 A1 | 5/2013 |
| WO | WO-2013082272 A1 | 6/2013 |
| WO | WO-2013106307 A1 | 7/2013 |
| WO | WO-2013148461 A1 | 10/2013 |
| WO | WO-2013150290 A1 | 10/2013 |
| WO | WO-2013162850 A1 | 10/2013 |
| WO | WO-2013163268 A1 | 10/2013 |
| WO | WO-2013165887 A1 | 11/2013 |
| WO | WO-2013184226 A1 | 12/2013 |
| WO | WO-2014014534 A2 | 1/2014 |
| WO | WO-2014033783 A1 | 3/2014 |
| WO | WO-2014014534 A3 | 4/2014 |
| WO | WO-2014064447 A1 | 5/2014 |
| WO | WO-2014102629 A1 | 7/2014 |
| WO | WO-2014129305 A1 | 8/2014 |
| WO | WO-2014139003 A1 | 9/2014 |
| WO | WO-2014192007 A1 | 12/2014 |
| WO | WO-2015009602 A1 | 1/2015 |
| WO | WO-2015015493 A2 | 2/2015 |
| WO | WO-2015015493 A3 | 3/2015 |
| WO | WO-2015038372 A1 | 3/2015 |
| WO | WO-2015042617 A1 | 3/2015 |
| WO | WO-2015058166 A2 | 4/2015 |
| WO | WO-2015058166 A3 | 6/2015 |
| WO | WO-2015101992 A2 | 7/2015 |
| WO | WO-2015101992 A3 | 9/2015 |
| WO | WO-2015138028 A2 | 9/2015 |
| WO | WO-2015138028 A3 | 11/2015 |
| WO | WO-2016022283 A1 | 2/2016 |
| WO | WO-2016033224 A1 | 3/2016 |
| WO | WO-2016059946 A1 | 4/2016 |
| WO | WO-2016063284 A2 | 4/2016 |
| WO | WO-2016124659 A1 | 8/2016 |
| WO | WO-2016125164 A2 | 8/2016 |
| WO | WO-2016125165 A2 | 8/2016 |
| WO | WO-2016162865 A1 | 10/2016 |
| WO | WO-2016196727 A2 | 12/2016 |
| WO | WO-2016196727 A3 | 1/2017 |
| WO | WO-2017051424 A1 | 3/2017 |
| WO | WO-2018015951 A1 | 1/2018 |
| WO | WO-2020075036 A1 | 4/2020 |

OTHER PUBLICATIONS

Anoplate Website. Accessed Jun. 3, 2015. http://www.anoplate.com/capabilities/anoblack_ni.html.

Avian Technologies Website. Accessed Jun. 3, 2015. http://www.aviantechnologies.com/products/coatings/diffuse_black.php.

Co-pending U.S. Appl. No. 15/479,105, filed Apr. 4, 2017.

Co-pending U.S. Appl. No. 15/667,360, filed Aug. 2, 2017.

Co-pending U.S. Appl. No. 15/713,198, filed Sep. 22, 2017.

Co-pending U.S. Appl. No. 15/858,340, filed Dec. 29, 2017.

Co-pending U.S. Appl. No. 15/867,245, filed Jan. 10, 2018.

Co-pending U.S. Appl. No. 15/901,627, filed Feb. 21, 2018.

Co-pending U.S. Appl. No. 15/905,578, filed Feb. 26, 2018.

Co-pending U.S. Appl. No. 16/232,959, filed Dec. 26, 2018.

Co-pending U.S. Appl. No. 16/389,723, filed Apr. 19, 2019.

Co-pending U.S. Appl. No. 16/437,826, filed Jun. 11, 2019.

Co-pending U.S. Appl. No. 16/450,695, filed Jun. 24, 2019.

Co-pending U.S. Appl. No. 16/657,847, filed Oct. 18, 2019.

Co-pending U.S. Appl. No. 16/744,062, filed Jan. 15, 2020.

Co-pending U.S. Appl. No. 16/746,588, filed Jan. 17, 2020.

EP17830604.9 Supplementary European Search report dated Feb. 6, 2020.

European search report and search opinion dated Feb. 7, 2017 for EP Application No. 14831451.1.

European search report and search opinion dated Jul. 24, 2015 for EP Application No. 12845773.6.

European search report and search opinion dated Aug. 7, 2017 for EP Application No. 15733267.7.

"Extended European Search Report and Search Opinion dated Dec. 13, 2017 for European Patent Application No. EP15733267.7".

"Interference Filter Handbook," published by JDS Uniphase (Second Edition), Sep. 2006, p. 195-202 and 213-214.

International search report and written opinion dated Jan. 26, 2015 for PCT Application No. IL2014/050688.

International search report and written opinion dated Mar. 22, 2013 for PCT Application No. IL2012/000367.

International search report and written opinion dated Jul. 14, 2015 for PCT Application No. PCT/IL2015/050002.

PCT/IL2017/050808 International Search Report and Written Opinion dated Nov. 2, 2017.

Co-pending U.S. Appl. No. 16/878,807, inventors Goldring Damian et al., filed May 20, 2020.

Co-pending U.S. Appl. No. 16/941,248, inventors Goldring Damian et al., filed Jul. 28, 2020.

\* cited by examiner

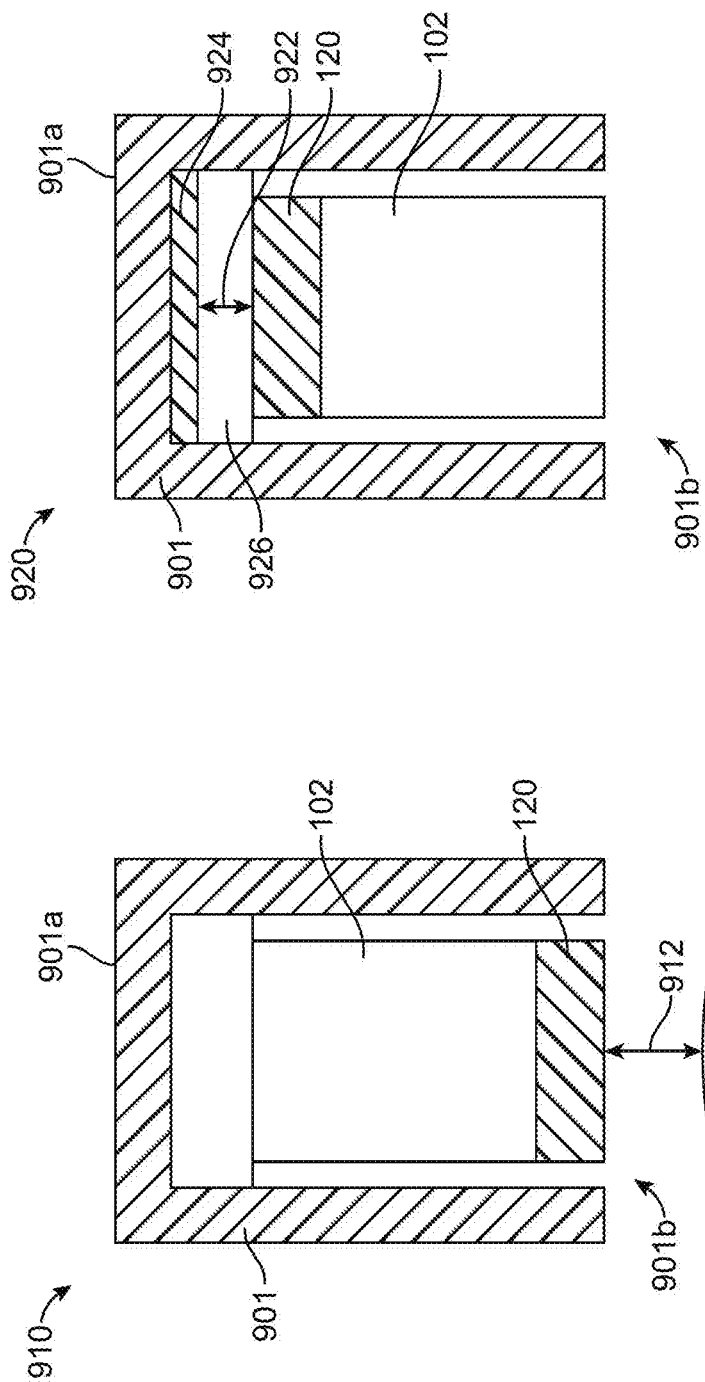

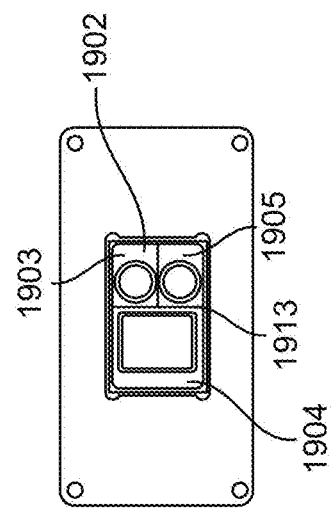
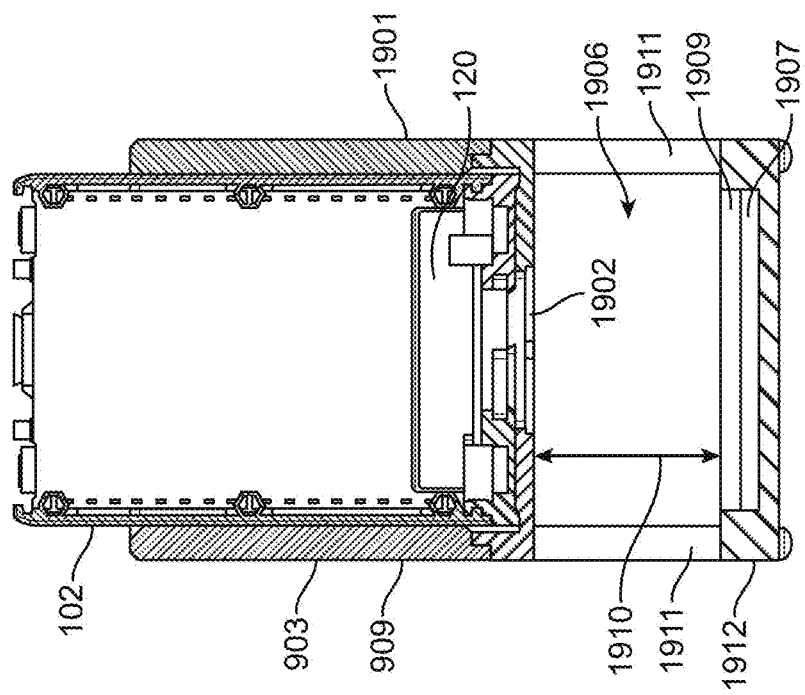
FIG. 19B
FIG. 19A

ACCESSORIES FOR HANDHELD SPECTROMETER

CROSS-REFERENCE

This application is a continuation of PCT Patent Application No. PCT/IL2017/050808, filed Jul. 18, 2017, which claims the benefit of U.S. Provisional Application No. 62/364,331, filed Jul. 20, 2016, and the benefit of U.S. Provisional Application No. 62/504,579 filed May 11, 2017, the disclosure of each of which is incorporated herein by reference.

BACKGROUND

Spectrometers are used for many purposes. For example spectrometers are used in the detection of defects in industrial processes, satellite imaging, and laboratory research. However these instruments have typically been too large and too costly for the consumer market.

Spectrometers detect radiation from a sample and process the resulting signal to obtain and present information about the sample that includes spectral, physical and chemical information about the sample. These instruments generally include some type of spectrally selective element to separate wavelengths of radiation received from the sample, and a first-stage optic, such as a lens, to focus or concentrate the radiation onto an imaging array.

The prior spectrometers can be less than ideal in at least some respects. Prior spectrometers having high resolution can be larger than ideal for use in many portable applications. Also, the cost of prior spectrometers can be greater than would be ideal. The prior spectrometers can be somewhat bulky, difficult to transport and the optics can require more alignment than would be ideal in at least some instances.

Although prior spectrometers with decreased size have been proposed. The prior spectrometers having decreased size and optical path length can have less than ideal resolution, sensitivity and less accuracy than would be ideal.

Work in relation to spectrometers suggests that the calibration and measurements with prior spectrometers can be less than ideal in at least some instances. For example, calibration of the spectrometer can be related to accuracy of the measurements. Also, work in relation to spectrometers suggests that positioning of the sample and related measurements can be less than ideal. Also, back ground noise from sources such as ambient light may affect the measurements. Traditional spectrometers can be large and bulky and approaches to at least some of these problems may not be well suited for use with a hand held portable spectrometer.

Work in relation to spectrometers also suggests that prior methods and apparatus to position a sample with respect to a spectrometer can be less than ideal in at least some instances. For example, variations in distance of the sample from the spectrometer may contribute to variability among results. The orientation of the sample may vary among samples and may contribute to variability among measured spectra. Also, background light and light reflected from surfaces near the sample may affect the measurements.

In light of the above, an improved spectrometer that overcomes at least some of the above mentioned deficiencies of the prior spectrometers would be beneficial. Ideally such a spectrometer would be a compact, provide improved measurements and calibration, be integratable with a consumer device such as a cellular telephone, sufficiently rugged and low in cost to be practical for end-user spectroscopic measurements of items, convenient and convenient to use.

SUMMARY

The present disclosure describes improved spectrometer methods and apparatus. In some cases a liquid measurement accessory for a handheld spectrometer, can comprise:
an injection unit;
a pipette unit said configured to be inserted into a measurement chamber part of the spectrometer.

In some cases, the measurement chamber part is located in the center of the pipette unit.

In some cases an extension device for a handheld spectrometer, can comprise:
one or more optical fiber bundles said bundles are connected to a measurement cup.

In some cases, the one or more optical fiber bundles are connected to a combiner.

In some cases, s handheld spectrometer apparatus to measure a body lumen of a subject, can comprise an illumination unit; a spectrometer unit; a housing containing the illumination unit and the spectrometer unit; an accessory, said accessory comprising a plurality of optical fibers, said optical fibers are configured to guide light from the illumination unit to the body lumen and back from the body lumen to the spectrometer unit.

In some cases, a handheld spectrometer apparatus to measure a body lumen of a subject, can comprise an illumination unit; a spectrometer unit; a housing containing the illumination unit and the spectrometer unit; an accessory, said accessory comprising one or more light pipes, said light pipes are configured to guide light from the illumination unit to the body lumen and back from the body lumen to the spectrometer unit.

In some cases, the handheld spectrometer apparatus of can comprise a cover and one or more adaptors for coupling said cover to the handheld spectrometer apparatus.

In some cases the accessory is a spectro-otoscope.

In some cases said body lumen is selected from the group comprising of: an ear, a nose, rectum In some cases a handheld spectrometer apparatus to measure a body lumen of a subject, can comprise an illumination unit; a spectrometer unit; a housing containing the illumination unit and the spectrometer unit; an accessory, said accessory comprising one or more optical fibers, said optical fibers are configured to guide light from the illumination unit to the body lumen and back from the body lumen to the spectrometer unit.

In some cases an otoscope accessory for a handheld spectrometer, can comprise:
a cover comprising a cavity; one or more engagement structures to couple the cover to a first end of the handheld spectrometer, the first end of the handheld spectrometer comprising an optical module having an illumination unit and a spectrometer; and at least two light pipes disposed within the cavity to be coupled to said illumination unit and a spectrometer to guide light from the illumination unit to the ear and back from the ear to the spectrometer unit.

In some cases an otoscope accessory for a handheld spectrometer, can comprise:
a cover comprising a cavity; one or more engagement structures to couple the cover to a first end of the handheld spectrometer, the first end of the handheld spectrometer comprising an optical module having an illumination unit and a spectrometer; and a plurality of optical fibers disposed within the cavity to be coupled to said illumination unit and a spectrometer to guide light from the illumination unit to the ear and back from the ear to the spectrometer unit.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative instances, in which the principles of the invention are utilized, and the accompanying drawings of which:

FIG. 9C shows a schematic diagram of a spectrometer placed within a cover in a measurement configuration.

FIG. 9D shows a schematic diagram of a spectrometer placed within a cover in a calibration configuration.

FIG. 17 shows an exploded assembly diagram of an.

FIG. 19A shows a cross section view of a spectrometer fitted in an accessory configured to perform a measurement of a liquid sample.

FIG. 19B shows a window provided on an accessory configured to perform a measurement of a liquid sample.

FIGS. 39-44 show a number of accessories to be coupled to a handheld spectrometer device.

FIG. 39 shows an advanced liquid accessory to enable convenient suction of liquid into a measurement chamber.

FIG. 40 shows an extension device configured to be attached to a spectrometer.

FIG. 41 shows measurement cup units as described with reference to FIG. 40.

FIG. 43 shows a perspective view of a spectro-otoscope comprising an otoscope accessory component coupled to a handheld device.

DETAILED DESCRIPTION

Figure 1:
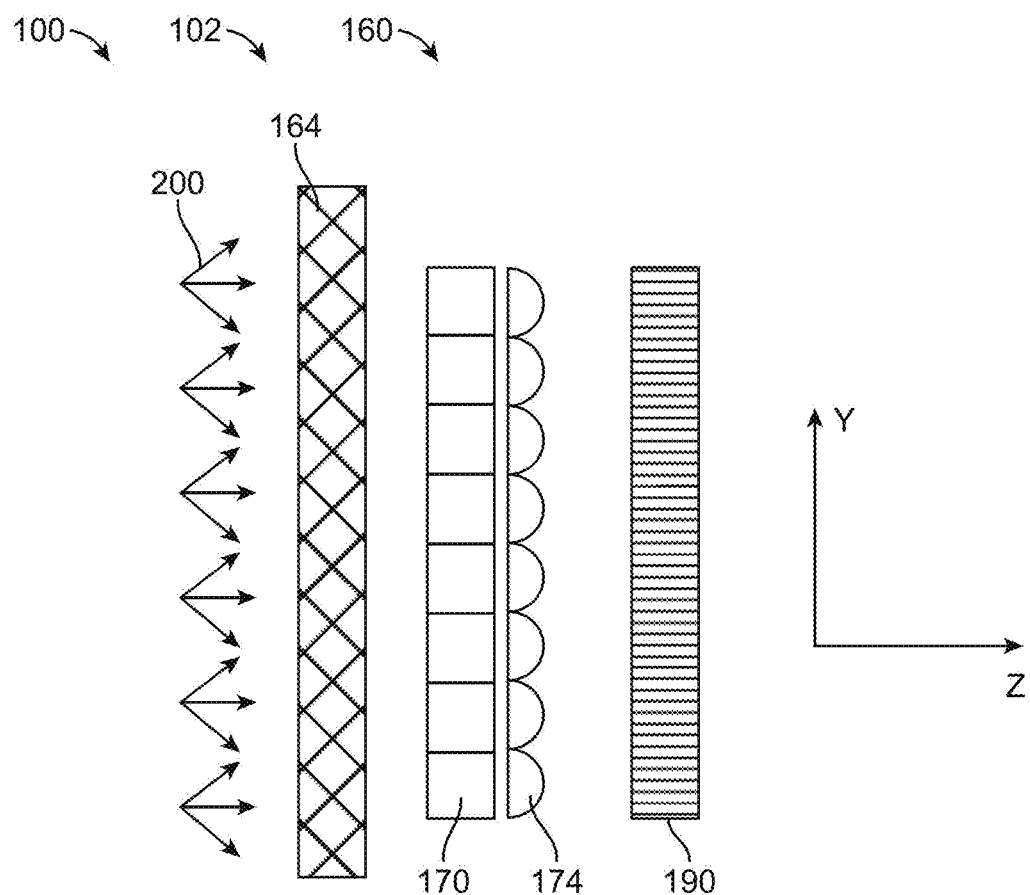
FIG. 1 shows schematic diagrams of the optical layout.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

A better understanding of the features and advantages of the present disclosure will be obtained by reference to the following detailed description that sets forth illustrative embodiments, in which the principles of embodiments of the present disclosure are utilized, and the accompanying drawings.

As used herein like characters identify like elements.

The examples disclosed herein can be combined in one or more of many ways to provide improved spectrometer methods and apparatus.

As used herein like characters refer to like elements.

As used herein "light" encompasses electromagnetic radiation having wavelengths in one or more of the ultraviolet, visible, or infrared portions of the electromagnetic spectrum.

As used herein, the term "dispersive" is used, with respect to optical components, to describe a component that is designed to separate spatially, the different wavelength components of a polychromatic beam of light. Non-limiting examples of "dispersive" optical elements by this definition include diffraction gratings and prisms. The term specifically excludes elements such as lenses that disperse light because of non-idealities such as chromatic aberration or elements such as interference filters that have different transmission profiles according to the angle of incident radiation. The term also excludes the filters and filter matrixes described herein.

The dimensions of an optical beam as described herein can be determined in one or more of many ways. The size of the beam may comprise a full width half maximum of the beam, for example. The measurement beam may comprise blurred edges, and the measurement area of the beam defining the measurement area of the sample may comprise a portion of the beam extending beyond the full width half maximum of the beam, for example. The dimensions of the aiming beam can be similarly determined.

The present disclosure describes improved spectrometer methods and apparatus. The spectrometer comprises a cover that can be used for calibration and sample measurements. The cover may comprise a container that holds one or more of the spectrometer, a calibration material or a reference sample. The cover may comprise a protective sheath having a closed end and an open end sized to receive the spectrometer. The spectrometer can be placed in the sheath to calibrate the spectrometer and to measure samples. In a calibration orientation, an optical head of the spectrometer can be oriented toward the closed end of the sheath where a calibration material is located. In a measurement orientation, the optical head of the spectrometer can be oriented toward the open end of the sheath in order to measure a sample. To change the orientation, the spectrometer can be removed from the sheath container and placed in the sheath container with a calibration orientation or a measurement orientation.

The sheath may comprise a structure having an open end, a closed end, and an interior sized to receive the spectrometer, and one or more engagement structures to receive the spectrometer in a first orientation with spectrometer optics oriented toward the closed end and a second orientation with the spectrometer optics oriented toward the open end.

Accessory container covers can be provided and placed on the open end of the sheath with samples placed therein in order to provide improved measurement of the samples with decreased interference from sources of noise such as ambient light. The accessory cover comprising the container can have the advantage of placing the measured material at a predetermined location and orientation with respect to the spectrometer in order to improve the repeatability and accuracy of the measurements.

The protective sheath cover may comprise an optically non-transmissive material in order to inhibit interference from sources of noise such as background light.

The protective sheath cover may comprise a support having internal engagement structures to receive a housing of the spectrometer, and the housing may comprise one or more corresponding engagement structures to engage the protective sheath cover. The protective sheath cover may comprise a second engagement structures to hold the accessory sample container when the spectrometer is oriented to measure a sample placed in the container.

In many instances, a kit comprises the spectrometer, the protective sheath cover, and an accessory sample container. In many instances, the sheath cover comprises a hollow handle to hold the spectrometer, and the internal engagement structures are located near the closed end of the sheath cover and the second engagement structures are located near the open end with an axis of the handle extending therebetween.

In many instances, the sheath covering, the accessory cover container and the spectrometer are arranged to form an outer closed protective container having the spectrometer contained therein when the accessory cover has been placed on the open end of the protective sheath cover in order to cover the open end.

In many instances, an accessory container comprises a structure shaped to receive a sample such as a pill or liquid in order to accurately hold the sample for measurement. The accessory container may comprise an insert comprising the structure shaped to receive the sample, and a plurality of inserts can be provided to measure objects having different shapes.

In some instances, the spectrometer apparatus can comprise a light source, a sensor array, and an accessory configured to permit sampling of a liquid by the spectrometer. The spectrometer apparatus can further comprise a housing to support the light source and the sensor array. The accessory can form a liquid tight seal with the housing. The accessory can permit the spectrometer to be dipped into a liquid. The accessory can comprise an accessory housing defining an inner chamber. The accessory house can comprise one or more openings to allow liquid to enter an interior of the chamber.

In an aspect, the accessory housing can comprise a diffuser and a reflector. In some cases, the diffuser and the reflector can be a single component. The housing can comprise a reflective diffuser. The diffuser and reflector can be arranged to reflect light transmitted through the diffuser with the reflector. The accessory housing can comprise a reflective diffuser, the reflective diffuser can be arranged to diffusely reflect light transmitted through the reflective diffuser. The accessory can be configured with an engagement structure to place the diffuser and the reflector at a fixed distance from the spectrometer. The accessory can comprise a plurality of energy transmission channels to transmit energy to and from the liquid. The plurality of energy transmission channels can comprise one or more of an optical window or a heat transfer energy channel. In some cases, the heat transfer channel can comprise a layer of metal to conduct heat from the liquid in contact with a first side of the layer to an opposite side of the layer. The optical window can comprises a plurality of optical windows with an opaque material between the plurality of optical windows to inhibit optical cross-talk of a light beam projected to the liquid and light received from the liquid. The plurality of optical windows can comprise a light transmission window and a light receiving window with the opaque material located in between.

In some cases, the spectrometer apparatus can further comprise a heat transfer window configured to transmit infrared light energy to measure a temperature of the sample, the opaque material extending between the light transmission window, the light receiving window and the heat transfer window.

In some instances a spectrometer apparatus can comprise a housing, a light source, a sensor array, and one or more accessories configured to couple to the spectrometer with the housing.

The one or more accessories can comprise one or more of a sheath, a cover, an accessory shaped to receive a pill or an accessory configured to receive a liquid. The one or more accessories can comprise a plurality of one or more accessories. The housing can comprise an engagement structure shaped to couple to the one or more accessories. The housing and the one or more accessories can be configured to place the accessory on an end of the spectrometer.

In some cases, a kit can be housed in a package. In some cases, the package can be provided for sale.

In an instance a spectrometer apparatus can comprise a light source; a sensor array; and a cover to couple to the spectrometer apparatus, wherein the cover comprises a sheath cover sized to receive a housing containing a spectrometer comprising the light source and the sensor array. The cover can comprise a support to hold a sample contained in the cover to couple the light source to a detector with the sample placed thereon.

In an instance, a spectrometer apparatus can comprise a light source; a sensor array; and a cover to couple to the spectrometer apparatus, wherein the cover comprises a sheath cover sized to receive a housing containing a spectrometer comprising the light source and the sensor array.

In some cases, a spectrometer apparatus can comprise: a light source; a sensor array; and an accessory configured to fix or provide one or more of a position or an orientation of a calibration sample relative to the light source, wherein one or more of a sensor in the sensor array can be calibrated based on a signal detected from the calibration sample.

In some cases, a spectrometer apparatus can comprise a light source; an accessory configured to fix one or more of a position or an orientation of a pill shaped sample relative to the light source.

In some cases, a spectrometer apparatus can comprise a light source; an accessory configured to fix one or more of a position or an orientation of a liquid sample relative to the light source.

Reference is now made to FIG. 1, which illustrates non-limiting configurations of the compact spectrometer system 100 herein disclosed. As illustrated the system comprises a diffuser 164, a filter matrix 170, a lens array 174 and a detector 190.

The spectrometer can have a size and weight such that the spectrometer can be held by a user with only one hand. The spectrometer can have a size and weight such that the spectrometer can be portable. The spectrometer can have a weight of about 1 gram (g). For example, the spectrometer can have a weight within a range from about 1 g to about 200 g.

The compact spectrometer 102 may have an optical resolution of less than 10 nm, less than 5 nm, less than 4 nm, less than 3 nm, less than 2 nm, less than 1 nm, less than 0.5 nm, or less than 0.1 nm. The spectrometer can have an optical resolution that is between any of the two values given above. The spectrometer can have a temporal signal-to-noise ratio (SNR) of about 1000 for a single sensor reading (without averaging, at maximum spectral resolution) for a wavelength of about 1000 nm, or an SNR of about 2500 for a wavelength of about 850 nm. The compact spectrometer, when configured to perform algorithmic processing or correction of measured spectral data, may be able to detect changes in normalized signals in the order of about $1 \times 10^{-3}$ to about $1 \times 10^{-4}$, or about $5 \times 10^{-4}$. The light source of the illumination module may be configured to have a stabilization time of less than 1 min, less than 1 s, less than 1 ms, or about 0 s.

The spectrometer system can comprise a plurality of optical filters of filter matrix 170. The optical filter can be of any type known in the art. Non-limiting examples of suitable optical filters include Fabry-Perot (FP) resonators, cascaded FP resonators, and interference filters. For example, a narrow bandpass filter (≤10 nm) with a wide blocking range outside of the transmission band (at least 200 nm) can be used. The center wavelength (CWL) of the filter can vary with the incident angle of the light impinging upon it.

In some instances, the central wavelength of the central band can vary by 10 nm or more, such that the effective range of wavelengths passed with the filter is greater than the bandwidth of the filter. In some instances, the central wavelength varies by an amount greater than the bandwidth of the filter. For example, the bandpass filter can have a bandwidth of no more than 10 nm and the wavelength of the central band can vary by more than 10 nm across the field of view of the sensor.

In some instances, the spectrometer system may comprise a detector 190, which may comprise an array of sensors. In some instances, the detector can be capable of detecting light in the wavelength range of interest. The compact spectrometer system disclosed herein can be used from the UV to the IR, depending on the nature of the spectrum being obtained and the particular spectral properties of the sample being tested. In some instances, a detector that is capable of measuring intensity as a function of position (e.g. an array detector or a two-dimensional image sensor) can be used.

In some cases the spectrometer does not comprise a cylindrical beam volume hologram (CVBH).

In some cases, the spectrometer system can comprise a diffuser. When the light emanating from the sample is not sufficiently diffuse, a diffuser can be placed in front of other elements of the spectrometer. Collimated (or partially collimated light) can impinge on the diffuser, which then produces diffuse light which then impinges on other aspects of the spectrometer, e.g. an optical filter.

In some instances, the spectrometer system can comprise a filter matrix. The filter matrix can comprise one or more filters, for example a plurality of filters. Depending on the number of sub-filters, the wavelength range accessible to the spectrometer can reach hundreds of nanometers. In configurations comprising a plurality of sub-filters, the approximate Fourier transforms formed at the image plane (i.e. one per sub-filter) overlap, and the signal obtained at any particular pixel of the detector can result from a mixture of the different Fourier transforms.

In some cases, the filter matrix can be arranged in a specific order to inhibit cross talk on the detector of light emerging from different filters and to minimize the effect of stray light. For example, if the matrix is composed of 3×4 filters then there are 2 filters located at the interior of the matrix and 10 filters at the periphery of the matrix. The 2 filters at the interior can be selected to be those at the edges of the wavelength range. Without being bound by a particular theory the selected inner filters may experience the most spatial cross-talk but be the least sensitive to cross-talk spectrally.

The spectrometer system can comprise a detector 190. The detector can be sensitive to one or more of ultraviolet wavelengths of light, visible wavelengths of light, or infrared wavelengths of light.

In many cases, the principle of operation of compact spectrometer comprises one or more of the following attributes. Light impinges upon the diffuser. The light next impinges upon the filter matrix at a wide range of propagation angles and the spectrum of light passing through the sub-filters is angularly encoded. The angularly encoded light then passes through the lens array (e.g. Fourier transform focusing elements) which performs (approximately) a spatial Fourier transform of the angle-encoded light, transforming it into a spatially-encoded spectrum. Finally the light reaches the detector. The location of the detector element relative to the optical axis of a lens of the array corresponds to the wavelength of light, and the wavelength of light at a pixel location can be determined based on the location of the pixel relative to the optical axis of the lens of the array. The intensity of light recorded by the detector element such as a pixel as a function of position (e.g. pixel number or coordinate reference location) on the sensor corresponds to the resolved wavelengths of the light for that position.

In some cases, an additional filter can be placed in front of the compact spectrometer system in order to block light outside of the spectral range of interest (i.e. to prevent unwanted light from reaching the detector).

In instances in which the spectral range covered by the optical filters is insufficient, additional sub-filters with differing CWLs can be used.

In some cases, one or more shutters can allow for the inclusion or exclusion of light from part of the system. For example shutters can be used to exclude particular sub-filters. Shutters may also be used to exclude individual lens.

In some instances, the measurement of the sample can be performed using scattered ambient light.

In many instances, the spectrometer system can comprise a light source. The light source can be of any type (e.g. laser or light-emitting diode) known in the art appropriate for the spectral measurements to be made. In some cases the light source can emit light from 350 nm to 1100 nm. The wavelength(s) and intensity of the light source will depend on the particular use to which the spectrometer will be put. In some cases, the light source can emit light from 0.1 mW to 500 mW Because of its small size and low complexity, the compact spectrometer system herein disclosed can be integrated into a mobile communication device such as a cellular telephone. It can either be enclosed within the device itself, or mounted on the device and connected to it by wired or wireless means for providing power and a data link. By incorporating the spectrometer system into a mobile device, the spectra obtained can be uploaded to a remote location, analysis can be performed there, and the user notified of the results of the analysis. The spectrometer system can also be equipped with a GPS device and/or altimeter so that the location of the sample being measured can be reported. Further non-limiting examples of such components include a camera for recording the visual impression of the sample and sensors for measuring such environmental variables as temperature and humidity.

Because of its small size and low cost, the spectrometer system herein disclosed can also be integrated into kitchen appliances such as ovens (e.g. microwave ovens), food processors, toilets refrigerators etc. The user can then make a determination of the safety of the ingredients in real time during the course of food storage and preparation.

In many instances, the spectrometer can also include a power source (e.g. a battery or power supply). In some cases, the spectrometer can be powered by a power supply from a consumer hand held device (e.g. a cell phone). In some cases, the spectrometer can have an independent power supply. In some instances a power supply from the spectrometer can supply power to a consumer hand held device.

In many instances, the spectrometer can comprise a processing and control unit. In some cases, the spectrometer may not analyze the data collected, and the spectrometer can relay data to a remote processing and control unit, such as a back end server. Alternatively or in combination, the spectrometer may partially analyze the data prior to transmission to the remote processing and control unit. The remote processing and control unit can be coupled to the spectrometer with a consumer hand held device (e.g. a cell phone). The remote processing and control unit can be a cloud based system which can transmit analyzed data or results to a user. In some cases, a hand held device can be configured to receive analyzed data and can be associated with the spectrometer. The association can be through a physical connection or wireless communication, for example.

The spectrometers as described herein can be adapted, with proper choice of light source, detector, and associated optics, for a use with a wide variety of spectroscopic techniques. Non-limiting examples include Raman, fluorescence, and IR or UV-VIS reflectance and absorbance spectroscopies. Because, as described above, compact spectrometer system can separate a Raman signal from a fluorescence signal, in some cases, the same spectrometer can be used for both spectroscopies.

In some instances the spectrometer system can come equipped with a memory with a database of spectral data stored therein and a microprocessor with analysis software programmed with instructions. In some cases, the spectrometer system can be in communication with a computer memory having a database of spectral data stored therein and a microprocessor with analysis software programmed in. The memory can be volatile or non-volatile in order to store the user's own measurements in the memory. The database and/or all or part of the analysis software can stored remotely, and the spectrometer system can communicate with the remote memory via a network (e.g. a wireless network) by any appropriate method. Alternatively, the database of spectral data can be provided with a computer located near the spectrometer, for example in the same room.

In some instances in which the database is located remotely, the data base can be updated often at regular intervals, for example continuously. In these instances, each measurement made by a user of the spectrometer can increase the quality and reliability of future measurements made by any user.

Once a spectrum is then obtained it can be analyzed. In some cases, the analysis may not be contemporaneous. In some cases the analysis can occur in real time. The spectrum can be analyzed using any appropriate analysis method. Non-limiting examples of spectral analysis techniques that can be used include Principal Components Analysis, Partial Least Squares analysis, and the use of a neural network algorithm to determine the spectral components.

An analyzed spectrum can determine whether a complex mixture being investigated contains a spectrum associated with components. The components can be, e.g., a substance, mixture of substances, or microorganisms.

The intensity of these components in the spectrum can be used to determine whether a component is at a certain concentration, e.g. whether their concentration of an undesirable component is high enough to be of concern. Non-limiting examples of such substances include toxins, decomposition products, or harmful microorganisms. In some instances, if it is deemed likely that the sample is not fit for consumption, the user can be provided with a warning.

In some instances, the spectrometer can be connected to a communication network that allows users to share the information obtained in a particular measurement. An updatable database located in the "cloud" (i.e. the distributed network) constantly receives the results of measurements made by individual users and updates itself in real time, thus enabling each successive measurement to be made with greater accuracy and confidence as well as expanding the number of substances for which a spectral signature is available.

In various instances, the conversion of the raw intensity data to a spectrum may be performed either locally (with a processor and software supplied with the spectrometer system) or remotely. Heavier calculations for more complicated analyses for example can be performed remotely.

In instances that incorporate remote data analysis, the data transferred to the remote system may include one or more of raw detector data; pre-processed detector data or post-processed detector data in which the processing was performed locally; or the spectrum derived from the raw detector data.

In some cases, the spectrometer may not comprise a monochromator.

In some instances, the following signal processing scheme can be used. First, an image or a series of images can be captured by the image sensor in the spectrometer mentioned above. The images can be analyzed by a local processing unit. This stage of analysis may include any or all of image averaging, compensation for aberrations of the optical unit, reduction of detector noise by use of a noise reduction algorithm, or conversion of the image into a raw spectrum. The raw spectrum is then transmitted to a remote processing unit; in some cases, the transmission can be performed using wireless communication.

The raw spectrum can be analyzed remotely. Noise reduction can be performed remotely.

In instances in which a Raman spectrum is obtained, the Raman signal can be separated from any fluorescence signal. Both Raman and fluorescence spectra can be compared to existing calibration spectra. After a calibration is performed, the spectra can be analyzed using any appropriate algorithm for spectral decomposition; non-limiting examples of such algorithms include Principal Components Analysis, Partial Least-Squares analysis, and spectral analysis using a neural network algorithm. This analysis provides the information needed to characterize the sample that was tested using the spectrometer. The results of the analysis are then presented to the user.

Figure 2:
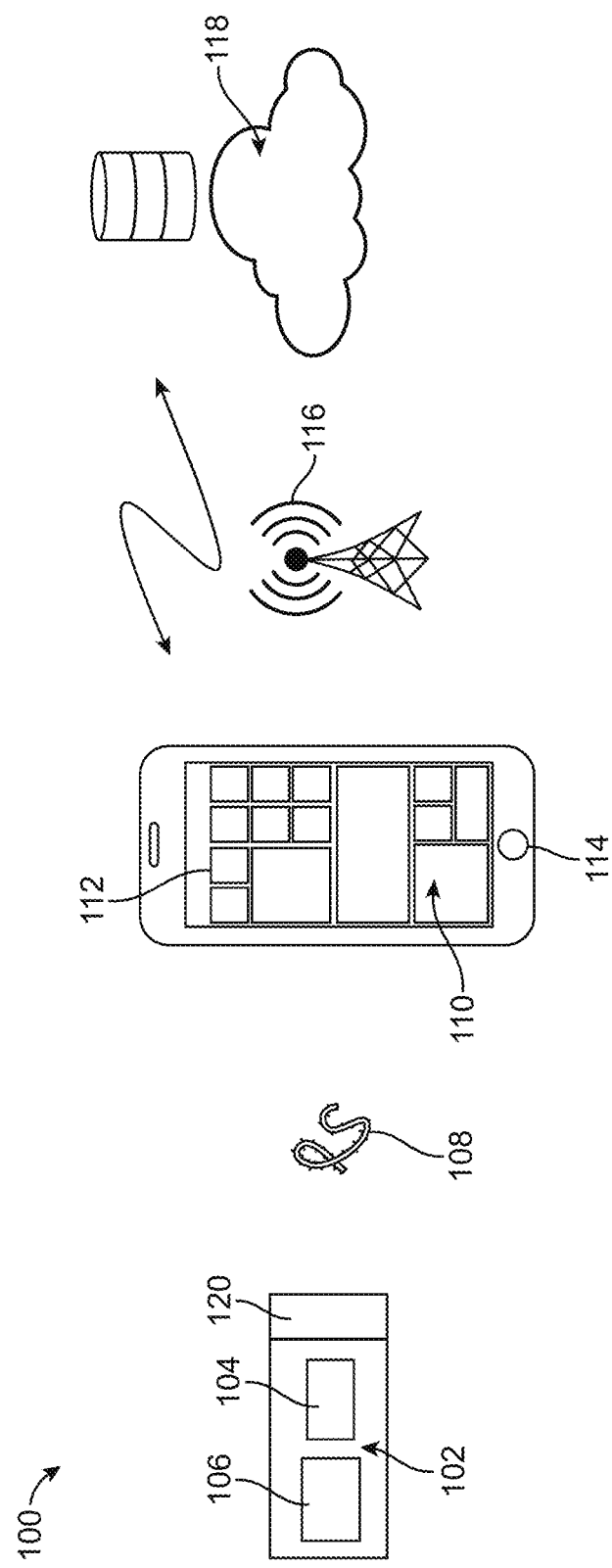
FIG. 2 shows a schematic diagram of a spectrometer system.

FIG. 2 shows a schematic diagram of a spectrometer system according to configurations. In many cases, the spectrometer system 100 can comprise a spectrometer 102 and a consumer hand held device 110 in wireless communication 116 with a cloud based storage system 118. The spectrometer 102 can acquire the data as described herein. The hand held spectrometer 102 may comprise a processor 106 and communication circuitry 104 coupled to spectrometer head 120 having spectrometer components as described herein. The spectrometer can transmit the data to the handheld device 110 with communication circuitry 104 with a communication link, such as a wireless serial communication link, for example Bluetooth™. The hand held device can receive the data from the spectrometer 102 and transmit the data to a back end server of the cloud based storage system 118.

The hand held device 110 may comprise one or more components of a smart phone, such as a display 112, an interface 114, a processor, a computer readable memory and communication circuitry. The device 110 may comprise a substantially stationary device when used, such as a wireless communication gateway, for example.

The processor 106 may comprise a tangible medium embodying instructions, such as a computer readable memory embodying instructions of a computer program. Alternatively or in combination the processor may comprise logic such as gate array logic in order to perform one or more logic steps.

Figure 3:
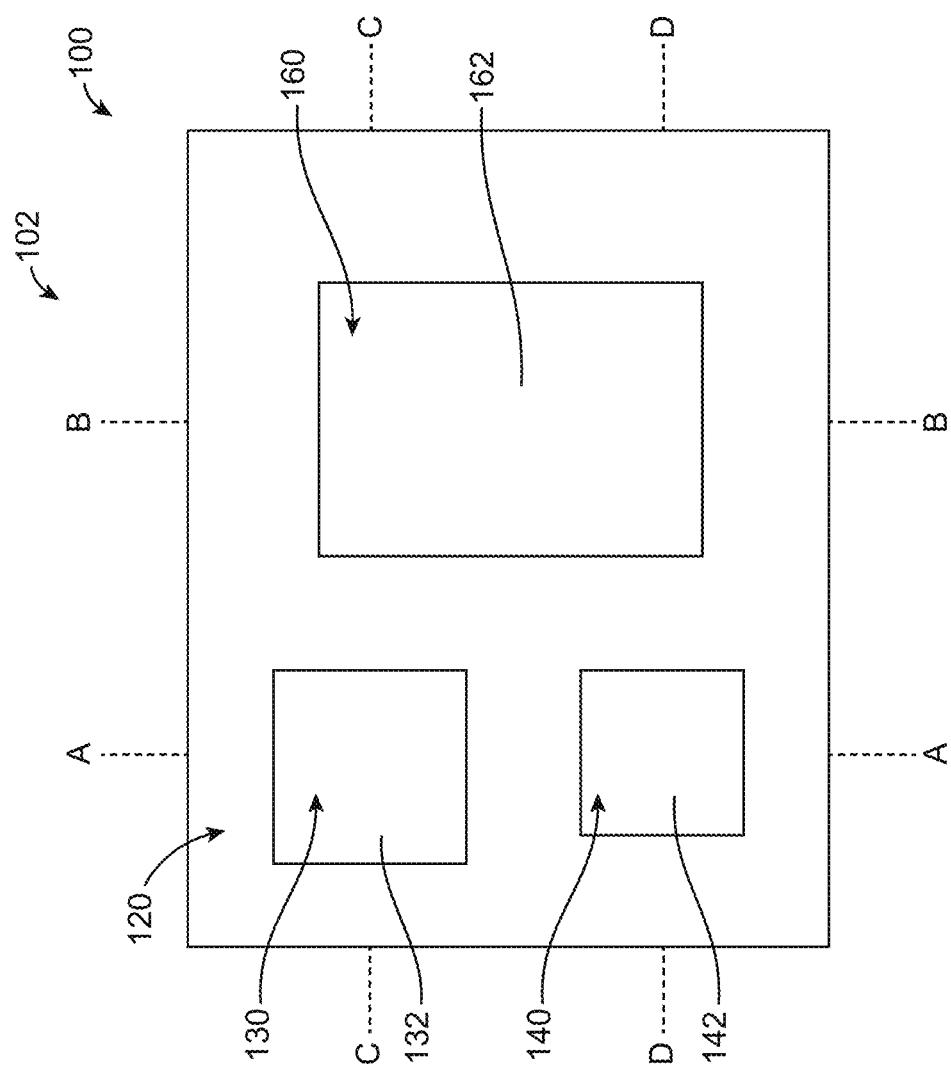
FIG. 3 shows a schematic diagram of a spectrometer head.

FIG. 3 shows a schematic diagram of spectrometer head in accordance with configurations. In many instances, the spectrometer 102 can comprise a spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a temperature sensor window 132, and the illumination module 140 can comprise an illumination window 142.

In many instances, the illumination module and the spectrometer module are configured to have overlapping fields of view at the sample. The overlapping fields of view can be provided in one or more of many ways. For example, the optical axes of the illumination source, the temperature sensor and the matrix array can extend in a substantially parallel configuration. Alternatively, one or more of the optical axes can be oriented toward another optical axis of another module.

Figure 4:
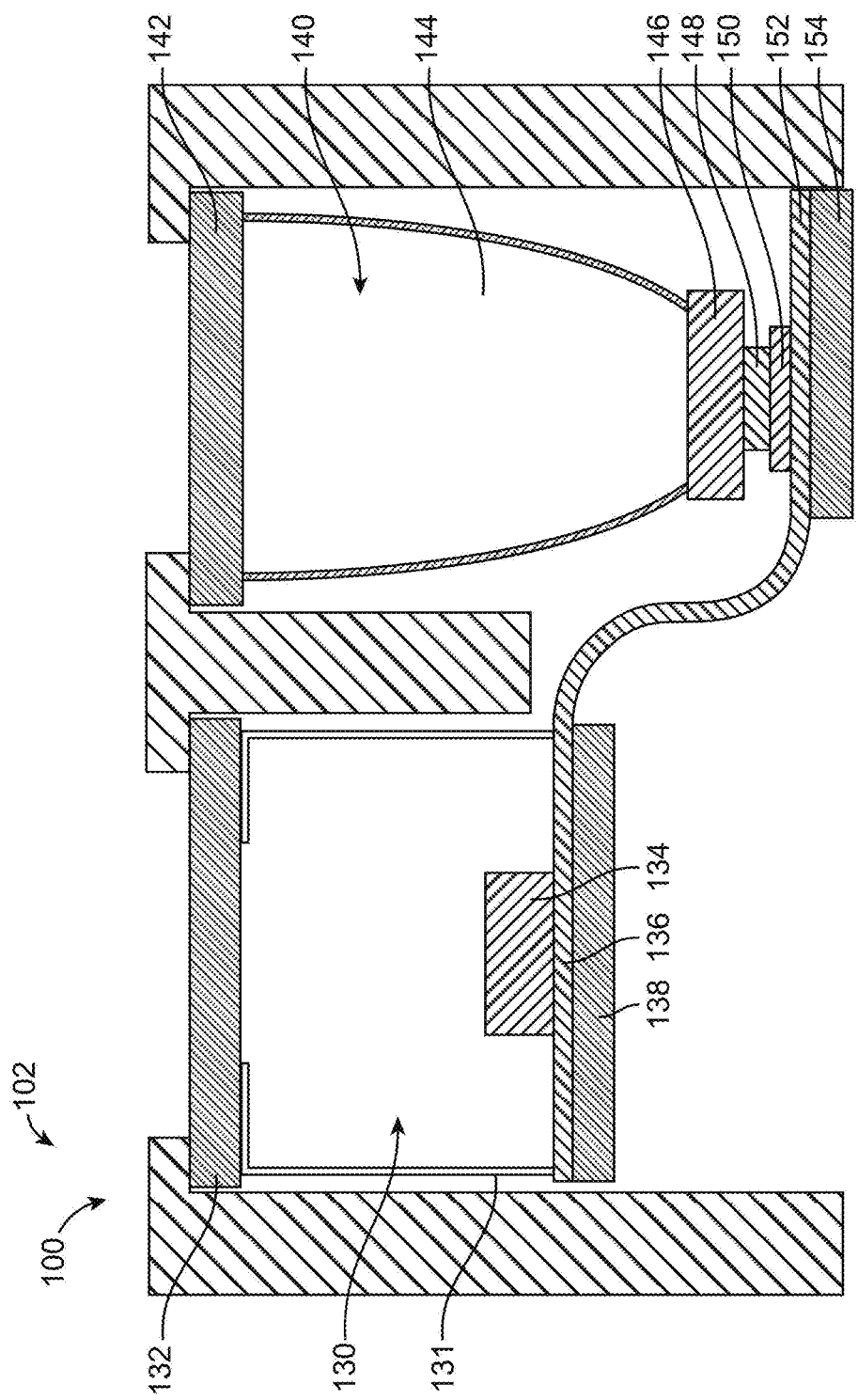
FIG. 4 shows a schematic diagram of cross-section A of the spectrometer head of FIG. 3.

FIG. 4 shows a schematic drawing of cross-section A of the spectrometer head of FIG. 3, in accordance with configurations. In order to lessen the noise and/or spectral shift produced from fluctuations in temperature, a spectrometer head 102 comprising temperature sensor module 130 can be used to measure and record the temperature during the measurement. In some instances, the temperature sensor element can measure the temperature of the sample in response to infrared radiation emitted from the sample, and transmit the temperature measurement to a processor. Accurate and/or precise temperature measurement can be used to standardize or modify the spectrum produced. For example, different spectra of a given sample can be measured based on the temperature at which the spectrum was taken. In some cases, a spectrum can be stored with metadata relating to the temperature at which the spectrum was measure. In many instances, the temperature sensor module 130 comprises a temperature sensor window 132. The temperature sensor can comprise a field of view (herein after "FoV") limiter. In many instances, the temperature sensor has a field of view oriented to overlap with a field of view of the detector and a field of view of an illuminator. For example, the field of view can be limited by an aperture formed in a material supporting the window 132 of temperature sensor module and the dimensions of the temperature sensor 134. In some cases, the temperature sensor module can have a limited field of view and comprise a heat conductive metal cage disposed on a flex printed circuit board (PCB) 136. The PCB 136 can be mounted on a stiffener 138 in order to inhibit movement relative to the other modules on the sensor head. In some cases, the flexible circuit board can be backed by stiffener 138 comprising a metal. The temperature sensor 134 can be a remote temperature sensor In many instances, the spectrometer head can comprise illumination module 140. The illumination module can illuminate a sample with light. In some cases, the illumination module can comprise an illumination window 142. The illumination window can seal the illumination module. The illumination window can be substantially transmissive to the light produced in the illumination module. For example, the illumination window can comprise glass. The illumination module can comprise a light source 148. In some cases, the light source can comprise one or more light emitting diodes (LED). In some cases, the light source can comprise a blue LED. In some instances, the light source comprises a red or green LED or an infrared LED.

The light source 148 can be mounted on a mounting fixture 150. In some cases, the mounting fixture comprises a ceramic package. For example, the light fixture can be a flip-chip LED die mounted on a ceramic package. The mounting fixture 150 can be attached to a flexible printed circuit board (PCB) 152 which can optionally be mounted on a stiffener 154 to reduce movement of the illumination module. The flex PCB of the illumination module and the PCT of temperature sensor modules may comprise different portions of the same flex PCB, which may also comprise portions of spectrometer PCB.

The wavelength of the light produced by the light source 148 can be shifted by a plate 146. Plate 146 can be a wavelength shifting plate. In some cases, plate 146 comprises phosphor embedded in glass. Alternatively or in combination, plate 146 can comprise a nano-crystal, a quantum dot, or combinations thereof. The plate can absorb light from the light source and release light having a frequency lower than the frequency of the absorbed light. In some instances, a light source can produce visible light, and plate 146 absorbs the light and emits near infrared light. In some cases, the light source can be in close proximity to or directly touches the plate 146.

The illumination module can further comprise a light concentrator such as a parabolic concentrator 144 or a condenser lens in order to concentrate the light. In some instances, the parabolic concentrator 144 is a reflector. In some instances, the parabolic concentrator 144 comprises stainless steel. In some cases, the parabolic concentrator 144 comprises gold-plated stainless steel. In some cases, the concentrator can concentrate light to a cone. For example, the light can be concentrated to a cone with a field of view of about 30-45, 25-50, or 20-55 degrees.

In some cases, the illumination module can be configured to transmit light and the spectrometer module can be configured to receive light along optical paths extending substantially perpendicular to an entrance face of the spectrometer head. In some instances, the modules can be configured to such that light can be transmitted from one module to an object (such as a sample 108) and reflected or scattered to another module which receives the light.

Figure 5:
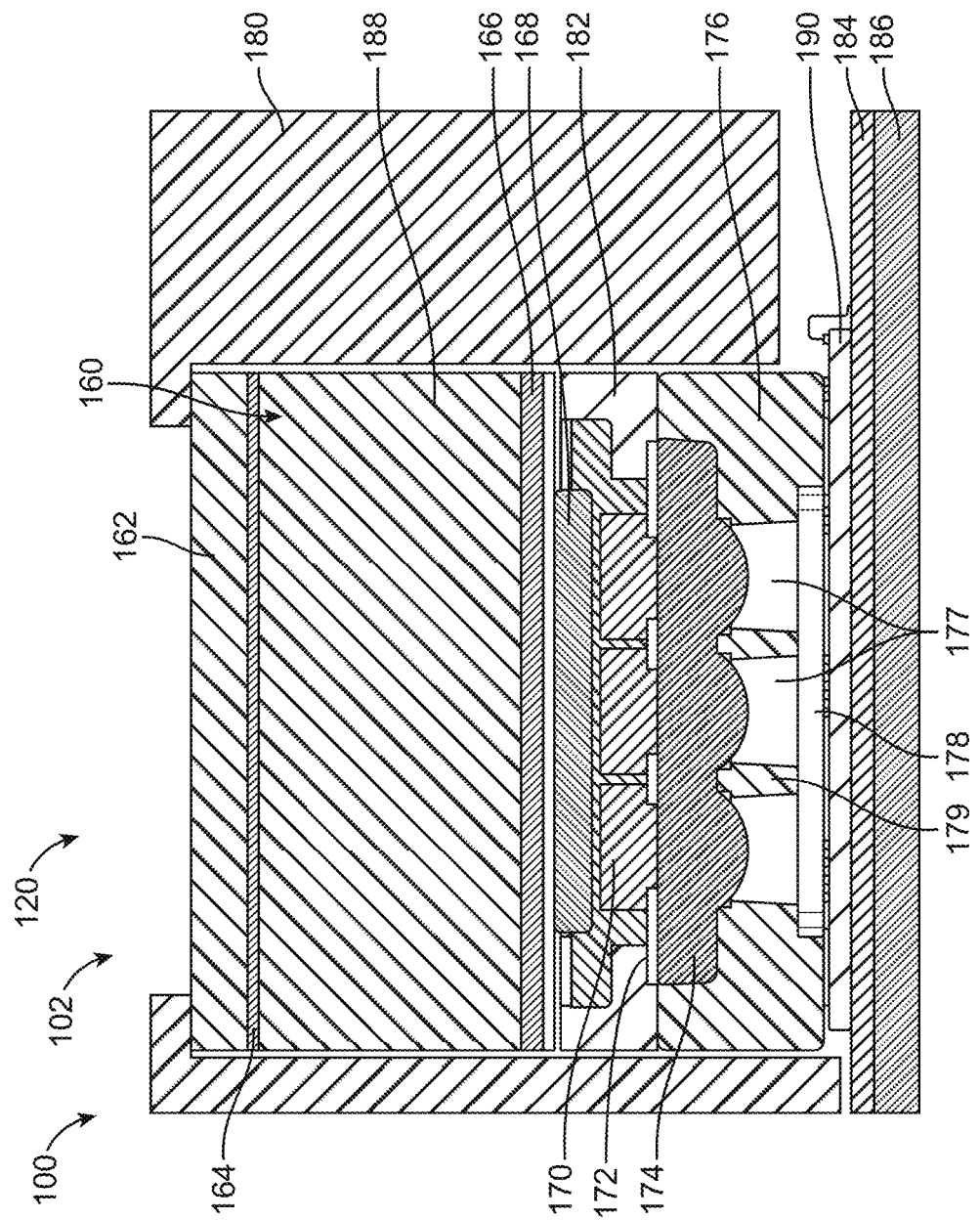
FIG. 5 shows a schematic diagram of cross-section B of the spectrometer head of FIG. 3.

In some instances, the optical axes of the illumination module and the spectrometer module can be configured to be non-parallel such that the optical axis representing the spectrometer module is at an offset angle to the optical axis of the illumination module. FIG. 5 shows a schematic drawing of cross-section B of the spectrometer head of FIGS. 3 and 4, in accordance with configurations. In many instances, the spectrometer head 102 can comprise a spectrometer module 160. The spectrometer module can be sealed by a spectrometer window 162. In some cases, the spectrometer window 162 can be selectively transmissive to light with respect to the wavelength in order to analyze the spectral sample. For example, spectrometer window 162 can be an IR-pass filter. In some cases, the window 162 can be glass. The spectrometer module can comprise one or more diffusers. For example, the spectrometer module can comprise a first diffuser 164 disposed below the spectrometer window 162. The first diffuser 164 can distribute the incoming light. For example, the first diffuser can be a cosine diffuser. Optionally, the spectrometer module comprises a light filter 188. Light filter 188 can be a thick IR-pass filter. For example, filter 188 can absorb light below a threshold wavelength. In some cases, filter 188 absorbs light with a wavelength below about 1000, 950, 900, 850, 800, 750, 700, 650, or 600 nm. In some instances, the spectrometer module can comprise a second diffuser 166. The second diffuser can generate Lambertian light distribution at the input of the filter matrix 170. The filter assembly can be sealed by a glass plate 168. Alternatively or in combination, the filter assembly can be further supported a filter frame 182, which can attach the filter assembly to the spectrometer housing 180. The spectrometer housing 180 can hold the spectrometer window 162 in place and further provide mechanical stability to the module.

The first filter and the second filter can be arranged in one or more of many ways to provide a substantially uniform light distribution to the filters. The substantially uniform light distribution can be uniform with respect to an average energy to within about 25%, for example to within about 10%, for example. In some cases, the first diffuser can distribute the incident light energy spatially on the second diffuser with a substantially uniform energy distribution profile. In some instances, the first diffuser can make the light substantially homogenous with respect to angular distribution. The second diffuser further diffuses the light energy of the substantially uniform energy distribution profile to a substantially uniform angular distribution profile, such that the light transmitted to each filter can be substantially homogenous both with respect to the spatial distribution profile and the angular distribution profile of the light energy incident on each filter. For example, the angular distribution profile of light energy onto each filter can be uniform to within about +/−25%, for example substantially uniform to within about +/−10%.

In many instances, the spectrometer module can comprise a filter matrix 170. The filter matrix can comprise one or more filters. In many instances, the filter matrix can comprise a plurality of filters. In some instances, each filter of the filter matrix 170 can be configured to transmit a range of wavelengths distributed about a central wavelength. The range of wavelengths can be defined as a full width half maximum (hereinafter "FWHM") of the distribution of transmitted wavelengths for a light beam transmitted substantially normal to the surface of the filter as will be understood by a person of ordinary skill in the art. A wavelength range can be defined by a central wavelength and by a spectral width. The central wavelength can be the mean wavelength of light transmitted through the filter, and the band spectral width of a filter can be the difference between the maximum and the minimum wavelength of light transmitted through the filter. For example, a filter can have a central wavelength of 300 nm and a wavelength range of 20 nm which would transmit light having a wavelength from 290 to 310 nm, and the filter would substantially not transmit light below 290 nm or above 310 nm. In some cases, each filter of the plurality of filters is configured to transmit a range of wavelengths different from other filters of the plurality. In some cases, the range of wavelengths can overlap with ranges of said other filters of the plurality and wherein said each filter comprises a central wavelength different from said other filters of the plurality.

In many instances, the filter array can comprise a substrate having a thickness and a first side and a second side, the first side can be oriented toward the diffuser, the second side can be oriented toward the lens array. In some cases, each filter of the filter array can comprise a substrate having a thickness and a first side and a second side, the first side oriented toward the diffuser, the second side oriented toward the lens array. The filter array can comprise one or more coatings on the first side, on the second side, or a combination thereof. Each filter of the filter array can comprise one or more coatings on the first side, on the second side, or a combination thereof. In some cases, each filter of the filter array can comprise one or more coatings on the second side, oriented toward the lens array. In some instances, each filter of the filter array can comprise one or more coatings on the second side, oriented toward the lens array and on the first side, oriented toward the diffuser. The one or more coatings on the second side can be an optical filter. For example, the one or more coatings can permit a wavelength range to selectively pass through the filter. Alternatively or in combination, the one or more coatings can be used to inhibit cross-talk among lenses of the array. In some instances, the plurality of coatings on the second side can comprise a plurality of interference filters, said each of the plurality of interference filters on the second side configured to transmit a central wavelength of light to one lens of the plurality of lenses. In some cases, the filter array can comprise one or more coatings on the first side of the filter array. The one or more coatings on the first side of the array can comprise a coating to balance mechanical stress. In some instances, the one or more coatings on the first side of the filter array can comprise an optical filter. For example, the optical filter on the first side of the filter array can comprise an IR pass filter to selectively pass infrared light. In many cases, the first side may not comprise a bandpass interference filter coating. In some cases, the first side may not comprise a coating.

In many instances, the array of filters may comprise a plurality of bandpass interference filters on the second side of the array. The placement of the fine frequency resolving filters on the second side oriented toward the lens array and apertures can inhibit cross-talk among the filters and related noise among the filters. In many cases, the array of filters can comprise a plurality of bandpass interference filters on the second side of the array, and may not comprise a bandpass interference filter on the first side of the array.

In many instances, each filter can defines an optical channel of the spectrometer. The optical channel can extend from the filer through an aperture and a lens of the array to a region of the sensor array. The plurality of parallel optical channels can provide increased resolution with decreased optical path length.

The spectrometer module can comprise an aperture array 172. The aperture array can prevent cross talk between the filters. The aperture array comprises a plurality of apertures formed in a non-optically transmissive material. In some cases, the plurality of apertures can be dimensioned to define a clear lens aperture of each lens of the array, wherein the clear lens aperture of each lens is limited to one filter of the array. In some cases, the clear lens aperture of each lens can be limited to one filter of the array.

In many instances the spectrometer module comprises a lens array 174. The lens array can comprise a plurality of lenses. The number of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

In many instances, each lens of the lens array comprises one or more aspheric surfaces, such that each lens of the lens array comprises an aspherical lens. In many cases, each lens of the lens array can comprise two aspheric surfaces. Alternatively or in combination, one or more individual lens of the lens array can have two curved optical surfaces wherein both optical surfaces are substantially convex. Alternatively or in combination, the lenses of the lens array may comprise one or more diffractive optical surfaces.

In many instances, the spectrometer module can comprise a support array 176. The support array 176 can comprise a plurality of channels 177 defined with a plurality of support structures 179 such as interconnecting annuli. The plurality of channels 177 may define optical channels of the spectrometer. The support structures 179 can comprises stiffness to add rigidity to the support array 176. The support array may comprise a stopper to limit movement and fix the position the lens array in relation to the sensor array. The support array 176 can be configured to support the lens array 174 and fix the distance from the lens array to the sensor array in order to fix the distance between the lens array and the sensor array at the focal length of the lenses of the lens array. In many cases, the lenses of the array can comprise substantially the same focal length such that the lens array and the sensor array are arranged in a substantially parallel configuration.

The support array 176 can extend between the lens array 174 and the stopper mounting 178. The support array 176 can serve one or more purposes, such as 1) providing the correct separation distance between each lens of lens array 170 and each region of the plurality of regions of the image sensor 190, and/or 2) preventing stray light from entering or exiting each channel, for example. In some cases, the height of each support in support array 176 can be calibrated to the focal length of the lens within lens array 174 that it supports. In some cases, the support array 176 can be constructed from a material that does not permit light to pass such as substantially opaque plastic. In some cases, support array 176 can be black, or comprises a black coating to further reduce cross talk between channels. The spectrometer module can further comprise a stopper mounting 178 to support the support array. In many instances, the support array can comprise an absorbing and/or diffusive material to reduce stray light, for example.

In many instances, the support array 176 can comprise a plurality of channels having the optical channels of the filters and lenses extending therethrough. In some cases, the support array comprise a single piece of material extending from the lens array to the detector (i.e. CCD or CMOS array).

In some cases, the spectrometer module can comprise an image sensor 190. The image sensor can be a light detector. For example, the image sensor can be a CCD or 2D CMOS or other sensor, for example. The detector can comprise a plurality of regions, each region of said plurality of regions comprising multiple sensors. For example, a detector can be made up of multiple regions, wherein each region is a set of pixels of a 2D CMOS. The detector, or image sensor 190, can be positioned such that each region of the plurality of regions is directly beneath a different channel of support array 176. In many instances, an isolated light path is established from a single of filter of filter array 170 to a single aperture of aperture array 172 to a single lens of lens array 174 to a single stopper channel of support array 176 to a single region of the plurality of regions of image sensor 190. Similarly, a parallel light path can be established for each filter of the filter array 170, such that there are an equal number of parallel (non-intersecting) light paths as there are filters in filter array 170.

The image sensor 190 can be mounted on a flexible printed circuit board (PCB) 184. The PCB 184 can be attached to a stiffener 186. In some cases, the stiffener can comprise a metal stiffener to prevent motion of the spectrometer module relative to the spectrometer head 120.

Figure 6:
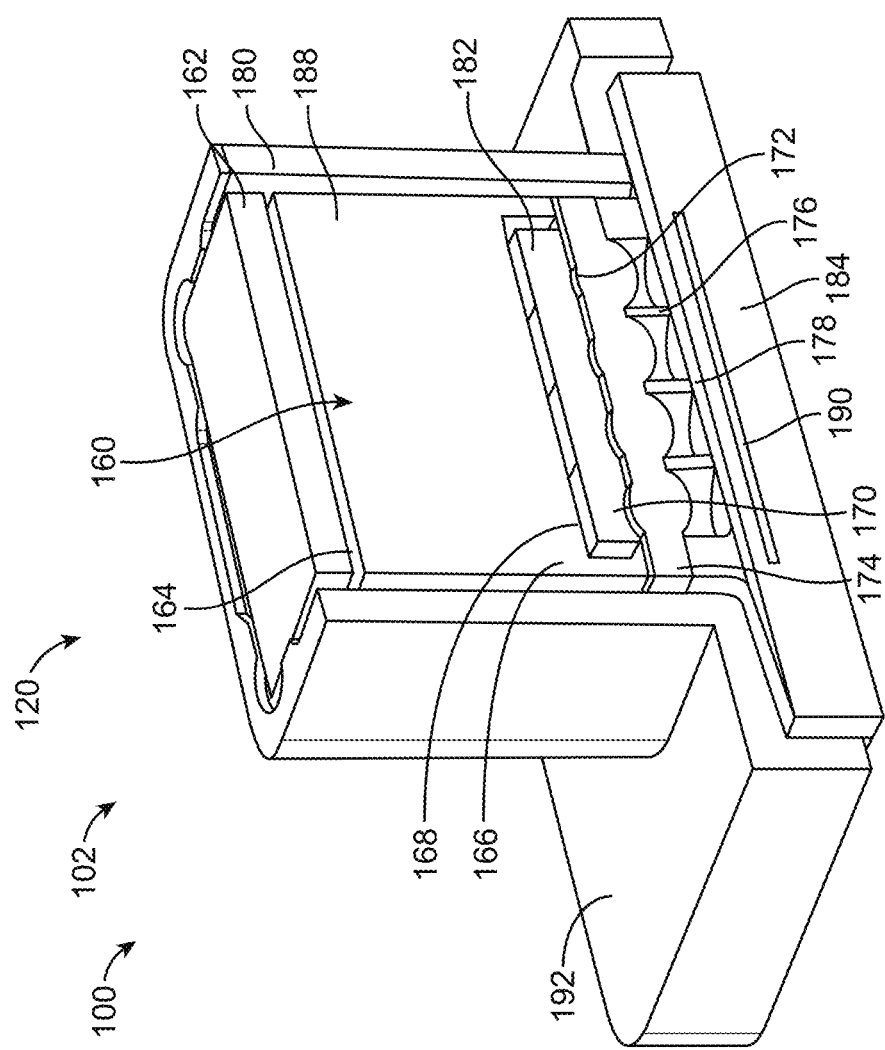
FIG. 6 shows a schematic diagram of a spectrometer module.

FIG. 6 shows an isometric view of a spectrometer module 160 in accordance with configurations. The spectrometer module 160 comprises many components as described herein. In many instances, the support array 176 can be positioned on a package on top of the sensor. In many instances, the support array can be positioned over the top of the bare die of the sensor array such that an air gap is present. The air gap can be less than 10, 9, 8, 7, 6, 5, 4, 3, 2 or 1 micrometer(s).

Figure 7:
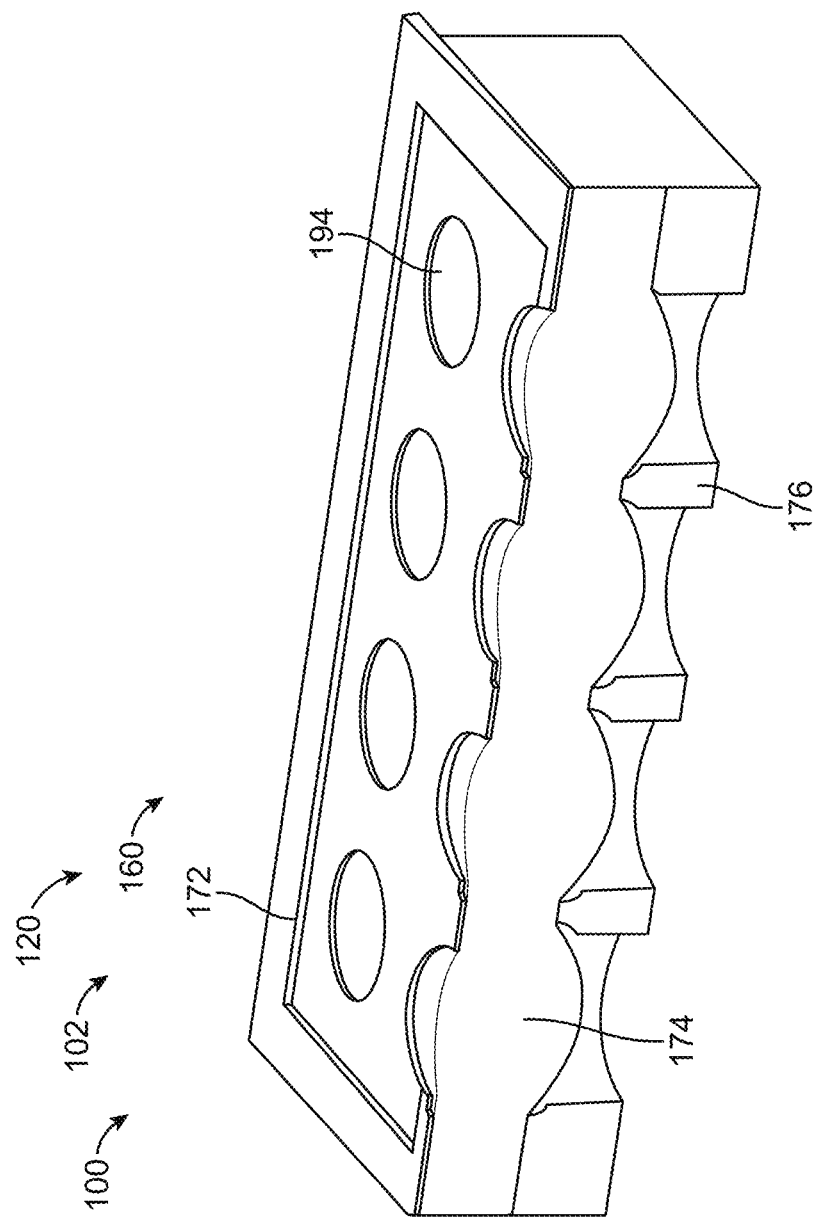
FIG. 7 shows a schematic diagram of apertures formed in a non-transmissive material and a lens array.

FIG. 7 shows the lens array 174 within the spectrometer module 160, in accordance with configurations. This isometric view shows the apertures 194 formed in a non-transmissive material of the aperture array 172 in accordance with configurations. In many cases, each channel of the support array 176 is aligned with a filter of the filter array 170, a lens of the lens array 174, and an aperture 194 of the aperture array in order to form a plurality of light paths with inhibited cross talk.

Figure 8:
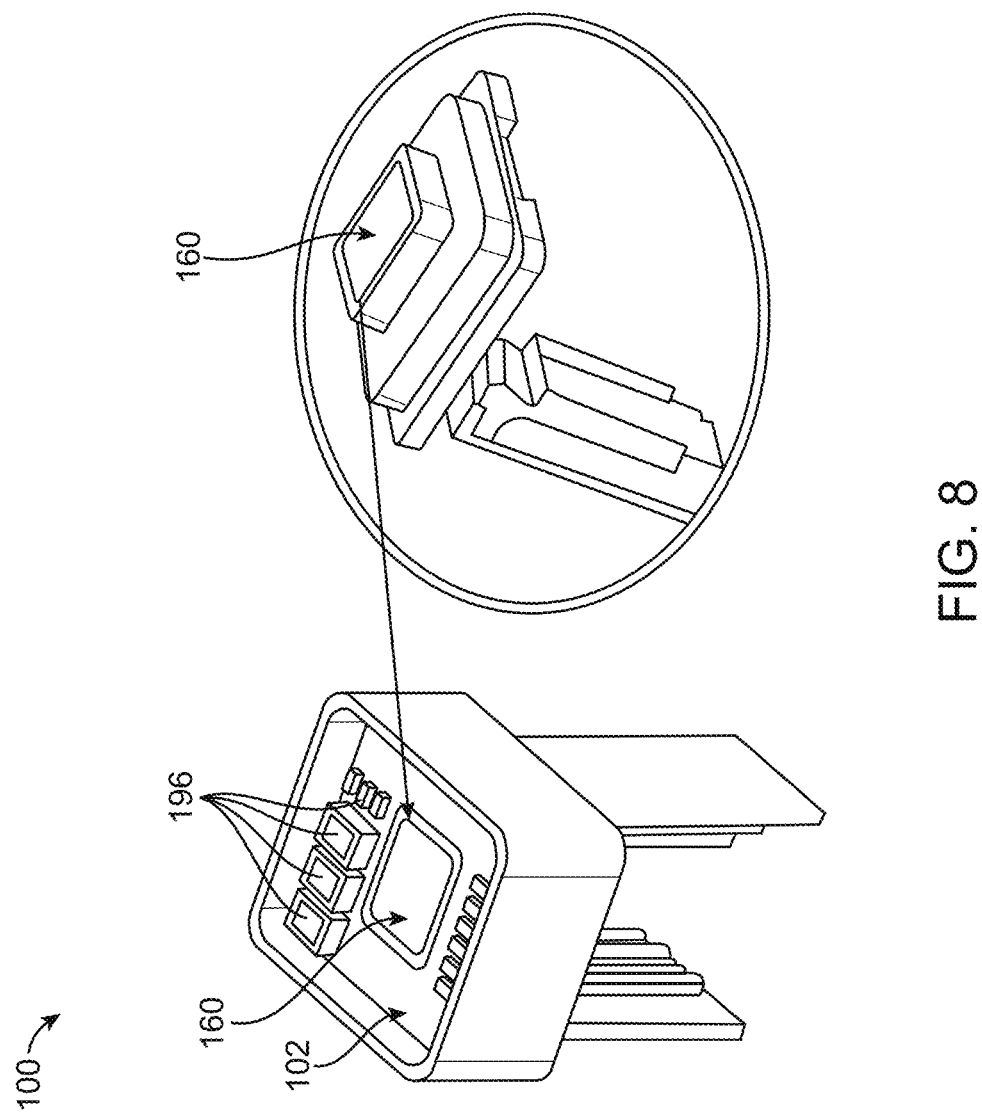
FIG. 8 shows a schematic diagram of a spectrometer.

FIG. 8 shows a spectrometer 102 in accordance with configurations. The spectrometer can comprise an optical head which can comprise a spectrometer module 160. The spectrometer can further comprise a temperature sensor module. In many cases, the spectrometer can comprise an illumination module. In many cases, the spectrometer can comprise light emitting diodes 196 distinct from an illumination module. The spectrometer can also comprise further components such as a Bluetooth™ module to communicate data to another device, a spectrometer processor 106, a power supply, or combinations thereof.

Figure 9A:
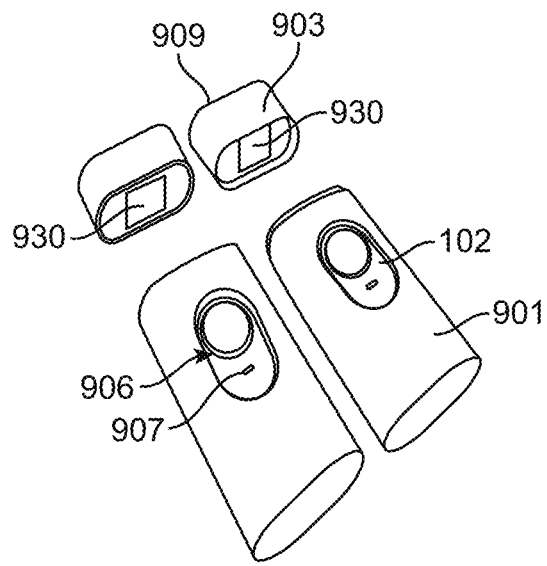
FIGS. 9A and 9B show perspective views of a spectrometer in a cover and a removable accessory container.
Figure 9B:
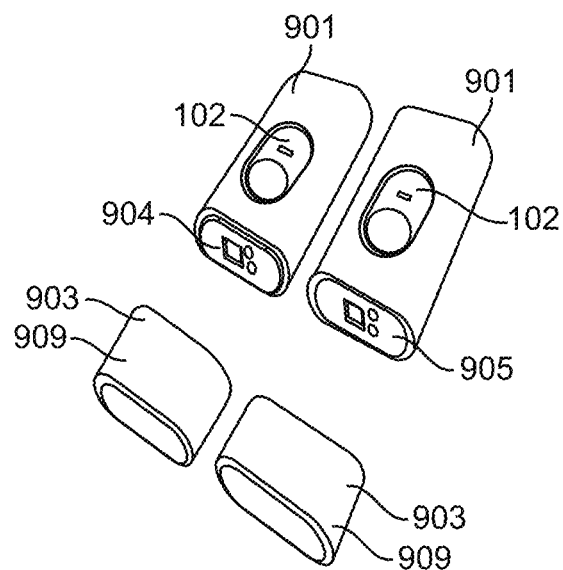

The spectrometer as described herein can be combined with a protective cover comprising a sheath. FIGS. 9A and 9B show perspective views of a spectrometer 102 as described herein placed in a protective sheath or cover 901 and coupled to a removable accessory 909 such as container 903, in accordance with configurations. In many cases, the cover 901 can comprise a protective sheath sized to receive the spectrometer. The cover can comprise a cover configured to fit over an end of the spectrometer or a cover configured to fit over more than an end of the spectrometer. The spectrometer can be removed from the sheath cover and placed in the sheath cover with an appropriate orientation to measure samples or calibrate the spectrometer. In many cases, the cover can have an open end and a closed end. In many instances, the spectrometer can comprise a protective housing sized to fit within the protective sheath. The spectrometer comprising the housing can be placed in the cover sheath with the optics of the spectrometer head directed toward the closed end of the cover sheath in order to calibrate the spectrometer. The cover may comprise a reflective calibration material to couple to the light source and the sensor array of the spectrometer, in order to reflect light from a calibration material to the sensor array in a repeatable manner. The reflective material may be a diffusive reflective material. The cover can be removable from the spectrometer. To measure a sample, the spectrometer can be placed in the cover 901 such that the spectrometer head faces the open end of the cover. In some cases, the cover can be configured to be removed and/or replaced by a user. The cover can provide a protective covering for the spectrometer during storage and use. In many instances, the cover can comprise a reference material for calibration of the spectrometer. The cover can additionally couple to an accessory 909 to provide a controlled measurement environment for conducting measurements of a sample.

FIG. 9C shows a schematic diagram of a spectrometer 102 placed within a cover 901 in a measurement configuration or orientation 910. The cover 901 may comprise a closed end 901a and an open end 901b. The spectrometer 102 may comprise a spectrometer head or optical module 120 as described herein. In the measurement configuration, the spectrometer may be placed in the cover such that the optical module is adjacent to the open end of the cover. In the measurement configuration, the spectrometer may be used to measure a sample 108 placed adjacent the optical module. The sample may be measured while the sample is placed at a measurement distance 912 between the optical head and the sample surface. In some configurations, the measurement distance 912 may be a predetermined measurement distance. For example, as described in further detail herein, the sample may be placed in a sample container configured to couple to the spectrometer and/or the cover such that the sample is placed at a predetermined measurement distance from the optical module of the spectrometer.

FIG. 9D shows a schematic diagram of a spectrometer 102 placed within a cover 901 in a calibration configuration or orientation 920. The cover 901 may comprise a closed end 901a and an open end 901b, wherein the cover 901 may comprise a reference material or calibration material 924 disposed near the closed end, as described in further detail elsewhere herein. In the calibration configuration, the spectrometer may be placed in the cover such that the optical module 120 of the spectrometer is adjacent to the closed end 901b of the cover, and facing the calibration material 924. In the calibration configuration, the spectrometer may be calibrated by measuring the calibration material. The calibration material may be placed at a predetermined calibration distance 922 between the optical module and the calibration material. For example, as described in further detail herein, the cover may comprise a base 926 configured to couple to the optical module of the spectrometer and place the optical module at a fixed calibration distance 922 from the calibration material.

In some cases, the spectrometer can be placed in a cover or sheath 901. The sheath can be made from a light weight material. The sheath can be made from a polymer, metal, or composite material. The cover or sheath can be sized and shaped such that the sheath does not add significant bulk to the volume of the spectrometer. The spectrometer can have a snug fit when placed in the spectrometer.

In many instances the accessory 909 may comprise a light source. The light source may be oriented such that a sample placed in the accessory is between the light source in the accessory and the optical head of the spectrometer. In some cases, the accessory may be configured to transmit light energy through a sample. The light energy that is transmitted through the sample may be detected by the optical head of the spectrometer. The light source in the accessory can be powered by a power source or power storage device in the accessory. In some cases, the light source in the accessory can be powered by a power source or power storage device in the spectrometer. The accessory can comprise one or more electrical contacts configured to contact one or more electrical contacts on the spectrometer. When the one or more electrical contacts on the accessory contact the one or more electrical contacts on the spectrometer, energy can be transferred from the power source or power storage device in the spectrometer to the light source in the accessory. In some instances the light source in the accessory can receive light from the light source in the spectrometer by a fiber optic transmission line. In some instances the accessory can further comprise a temperature sensor. The temperature sensor can measure temperature in the accessory and the measured temperature can be used in interpretation of spectrometer measurements of a sample placed in the accessory.

The accessory 909 can comprise a hollow region or cavity. The cavity can be a sample container 903. The sample container can be exposed to the spectrometer light source when the accessory is coupled to the spectrometer. Ambient light may not be permitted to enter the cavity when the accessory is coupled to the spectrometer. The sample container can comprise a non-optically transmissive material having a channel 930 formed therein to receive light energy from the spectrometer light source. The sample container can have walls that are coated with a material that does not reflect light energy. In some cases, the sample container can comprise at least one surface with a highly reflective coating. Alternatively or in combination, the sample container can have walls coated with a black coloring or coating. The black coloring or coating may not reflect light energy or may reflect a substantially small percentage of light energy.

At least one inner surface of the sample container 903 can be covered with or contain an optically reflective surface or entity. The optically reflective surface or entity can comprise a first reflective material having predetermined optical properties. The sample container can transmit reflected light, for example reflected light off the reflective surface or entity, or first reflective material, to the spectrometer sensor. The sample container can inhibit or prevent interference from ambient light. In many instances, ambient light can be light outside of the sample container. In some cases, the first reflective material can be a reflective material with a size and shape configured to fit within a recess formed in the sample container. The reflective material can have known optical properties. For example, an optical property that can be known for the reflective material can be reflectivity, absorptivity, and/or transmissivity. The known optical properties of the reflective material can be constant with respect to one or more environmental properties, for example, temperature, humidity, and/or pressure. The known optical properties of the reflective material can be constant with respect to the properties of light incident on the reflective material. In many instances, properties of the light incident on the reflective material can include wavelength, intensity, and/or frequency. In some cases, the sample container can comprise a second reflective material on an inner side wall of the channel to reflect light energy from the spectrometer light source toward the first reflective material, and from the first reflective material toward the spectrometer sensor array. The second reflective material can have a size and shape such that it is configured to fit along a side wall of the sample container channel. The second reflective material can have known optical properties.

The spectrometer can further comprise a support to engage the accessory 909 or the cover 901 and place the reflective material of the sample container 903 at a predetermined distance from the spectrometer light source and sensor array. The predetermined distance can be a fixed or variable distance. The accessory can comprise an engagement structure to engage the support on the spectrometer. The support can be shaped to receive, couple to, and/or mate with the engagement structure of the accessory. The engagement structure can be removably coupled to the support. The accessory can be attached to the spectrometer when the support and engagement structure are positively mated or coupled. The engagement structure can permit placement and removal of the accessory on the spectrometer. The engagement structure can couple the accessory to the spectrometer such that ambient light cannot enter the container. In some cases, the engagement structure can comprise one or more of a protrusion, a rim, a flange, a recess, or a magnet. The support can comprise one or more of a protrusion, a rim, a flange, a recess, or a magnet configured to engage a corresponding portion of the engagement structure. In some cases, a locking mechanism can further couple the spectrometer and the cover. A user can release the locking mechanism to remove the accessory from the spectrometer. In many instances, a locking mechanism can be a pin and tumbler locking mechanism.

Additionally, an accessory 909 comprising a sample container 903 can be coupled to the spectrometer 102 as described herein. In some cases, the sample container 903 and the cover 901 can couple to the spectrometer interchangeably. Alternatively, the sample container and the cover can couple to the spectrometer simultaneously. The spectrometer 102, the cover 901, and the sample container 903 are shown in FIGS. 9A and FIG. 9B. FIG. 9A shows the spectrometer 102 inside of the container of the cover 901, with a sample container 903. The sample container 903 can contain a material to be measured by the spectrometer. As shown in FIGS. 9A and 9B the spectrometer is placed in the cover with the spectrometer head facing outward. These configurations can be used to collect sample measurements. In alternate configurations, the spectrometer can be flipped such that the spectrometer head faces into the cover, wherein this configuration can be used during calibration.

In many cases, the container of the cover 901 comprises a sheath cover that can be configured to receive the spectrometer 102 contained within the housing as described herein. The cover 901 may comprise one or more openings 906 through which one or more structural features of the spectrometer can be accessed. In some cases, a protrusion 907 on the spectrometer 102 may be accessed through the one or more openings 906. The protrusion 907 can comprise a raised bump, raised line, a groove, a depression, a textured surface, a nub, and/or a raised structural feature that can be gripped by a user's hand and/or finger. A user may push the spectrometer 102 out of the container 902 by pushing and/or pulling on the protrusion 907 to apply a shear force to the spectrometer. The sheath cover may comprise an open end sized to receive the spectrometer and housing and a closed end opposite the open end. The spectrometer can be received in the sheath cover with the spectrometer optics head oriented toward the closed end, such that the spectrometer and sheath comprise a calibration configuration. Alternatively, the spectrometer can be received in the sheath cover with the spectrometer optics head oriented toward the open end, such that the spectrometer and sheath comprise a measurement configuration. The calibration material can be located closer to the closed end than the open end in order to calibrate the spectrometer.

The sheath or cover may comprise a structure having an open end, a closed end, and an interior sized to receive the spectrometer, and one or more engagement structures to receive the spectrometer in a first orientation with spectrometer optics oriented toward the closed end and a second orientation with the spectrometer optics oriented toward the open end.

The sample container 903 (e.g. accessory 909) can provide a controlled environment for measurement of a sample material by the spectrometer. The sample container can be removably attached to the spectrometer. In many cases, a user can measure properties of a sample material by placing the material in the sample container, attaching the sample container to the spectrometer and using the spectrometer to measure the material in the sample container. The sample container can place the material at a known distance from the spectrometer light source. When attached to the spectrometer, the sample container can inhibit noise signals from ambient light sources. Ambient light sources can be any light sources that do not originate from the light source of the spectrometer.

In many instances, the calibration material can be spaced apart from the optics head with a calibration distance in the calibration orientation and wherein the sample container is sized and shaped to place the sample spaced apart from the optics head with a measurement distance in the measurement orientation similar to the calibration distance to within about 100%.

In many cases, the sample container and the spectrometer can comprise mating or coupling attachment structural features. The sample container can be mounted on the optical head side of the spectrometer. In many cases, the coupling attachment structural features can be complementary structural features on the sample container and the spectrometer. The complimentary structural features can comprise one or more of a protrusion, a rim, a flange, a recess, or a magnet configured to couple the sample container to the spectrometer. FIG. 9B shows a sample container 903 configured to fit over a stepped protrusion 904 on a spectrometer 102. Alternatively, FIG. 9B also shows a sample container 903 configured to couple to a flush surface 905 of the spectrometer 102.

The sample container and/or the cover can comprise asymmetric mating structural features such that the sample container can connect to the spectrometer only in a preferred orientation. In many instances, asymmetric mating structural features can be grooves, channels, pins, or other shape factors provided on either or both of the container and/or cover and the spectrometer. The asymmetric mating structural features can prevent the sample container from connecting to the spectrometer in at least one orientation. The asymmetric structural features can force the sample container to be mounted on the spectrometer such that a sample in the sample container is in a known location relative to the spectrometer. The known location can be a known location relative to the light source in the spectrometer. In some instances, the known location relative to the light source in the spectrometer is a horizontal or vertical distance. In some cases, the known location relative to the light source in the spectrometer is an angular orientation in relation to the light source and the sensor array.

Figure 10:
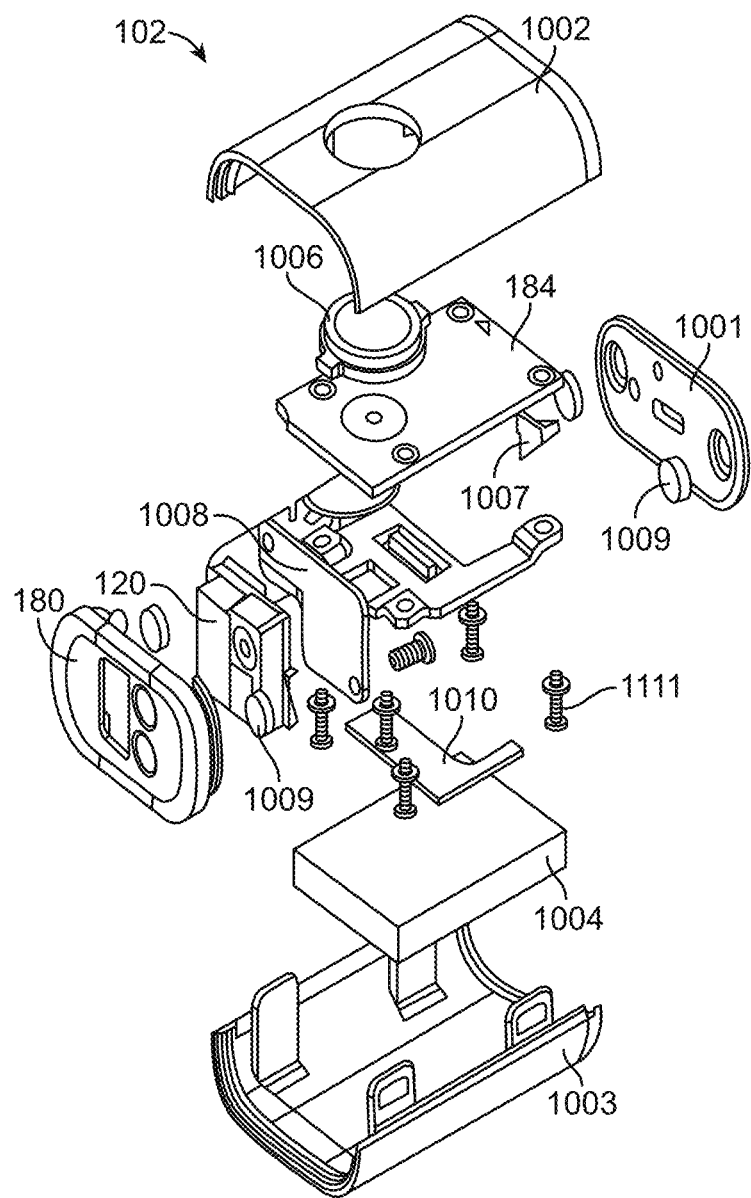
FIG. 10 shows an exploded assembly diagram of a spectrometer.

FIG. 10 shows and exploded view of the spectrometer 102. The spectrometer shown in FIG. 10 can be placed in the cover as described herein. The spectrometer can be enclosed by a set of housing pieces. The housing pieces can be connected by one or more screws or fasteners 1111. The housing pieces can include a head housing 180, a tail housing 1001, a top housing 1002, and a bottom housing 1003. The housing pieces can be removably connected. In some cases, the housing pieces can snap or slide open or apart to open and provide access to an interior region enclosed by the housing pieces. In some instances the housing pieces can be opened to provide access to a battery 1004. The battery can be a rechargeable or replaceable battery. In the case of a rechargeable battery, the battery can be removed from the housing for recharging or the spectrometer can comprise charging contact to charge the battery while the battery is in the device. The charging contact can provide an electrical connection between the battery and an exterior surface of the housing. The battery 1004 can be a power source for the spectrometer components, for example, the battery can power the light source can one or more processors on-board the spectrometer configured to perform measurements. The battery can be fixed in the housing by an adhesive, for example battery tape 1010. An operating button 1006 can allow a user to control battery power to one or more components in the spectrometer. In some cases, a user can power a spectrometer on and off by manipulating the operating button. An operating button can be a compressible button, switch, or touchscreen (e.g. capacitive screen). In many instances, a user can push the operating button 1006 to complete an electrical circuit such that the circuit is closed when a user pushes the button and the battery 1004 provides power to one or more components in the spectrometer. The user can push the button 1006 again to open the circuit and prevent the battery 1004 from providing power to one or more components in the spectrometer. In some cases, the operating button 1006 can be pressed in a predetermined sequence to program one or more features of the spectrometer. The button 1006 can be accessible through an opening on one or more of the housing pieces, for example, the button 1006 can be accessible through the top housing 1002. The battery 1004 can be connected to a battery indicator 1007. The battery indicator 1007 can be configured to sense the voltage of the battery 1004. The battery indicator can communicate the health (e.g. remaining charge) of the battery to a user. In many instances, the battery indicator 1007 can be an LED. The battery indicator can be visible by extruding through a housing piece or through a window on a housing piece. In many instances, the battery indicator can be visible through the tail housing 1001. In some cases the battery indicator can be an LED that is red and/or flashing when the battery has a low charge.

The battery 1004 can provide power to the spectrometer head 120 which can also be referred to as the optical module. The optical module 120 can be in communication with a PCB 184. The optical module 120 can be connected to a heat sink 1008. The heat sink 1008 can be a thermally conductive material configured to remove heat from either or both of the optical module 120 and the PCB 184. In some cases, the heat sink 1008 can comprise heating fins. The optical module can be covered by the head housing 180. The head housing can comprise one or more windows such that optical components of the optical module can be exposed to the exterior of the housing.

The spectrometer can comprise a measurement portion and a handle portion to direct the measurement portion toward a sample. The handle portion can be sized and configured for handling by a user with one hand. The spectrometer can comprise the support configured to couple to the engagement structure on the cover. The measurement portion can comprise the support. The handle portion can comprise a support sized and shaped to receive the cover. The cover can be coupled to either or both of the measurement portion or the handle portion. The support can comprise a housing to enclose the light source and the sensor array. The spectrometer can have a window to receive light from a sample. The support and the cover can be configured to place a reflective material at a predetermined distance from the window with a gap extending between the reflective material and the window.

The head and tail housing can comprise one or more magnets 1009. The magnets can be exposed to the outer surface of the housing or the magnets can be imbedded in the housing such that they are not exposed on the outer surface. The magnets can be configured to mate with, attract, or couple to magnets or magnetic materials provided on the cover and/or the sample container. The magnets can be the support on the spectrometer configured to couple to the engagement structure on the cover. The engagement structure can comprise a cover magnetic material configured to couple to the support magnetic material. In some cases, the engagement structure and the support can comprise corresponding asymmetric engagement structures to position the cover at a predetermined position and angular orientation with respect to the light source and the sensor array. In many cases, the polarity of the magnets can be an asymmetric engagements structure when the polarity is chosen such that some orientations of the cover and spectrometer are permitted while other configurations are prevented.

Figure 11:
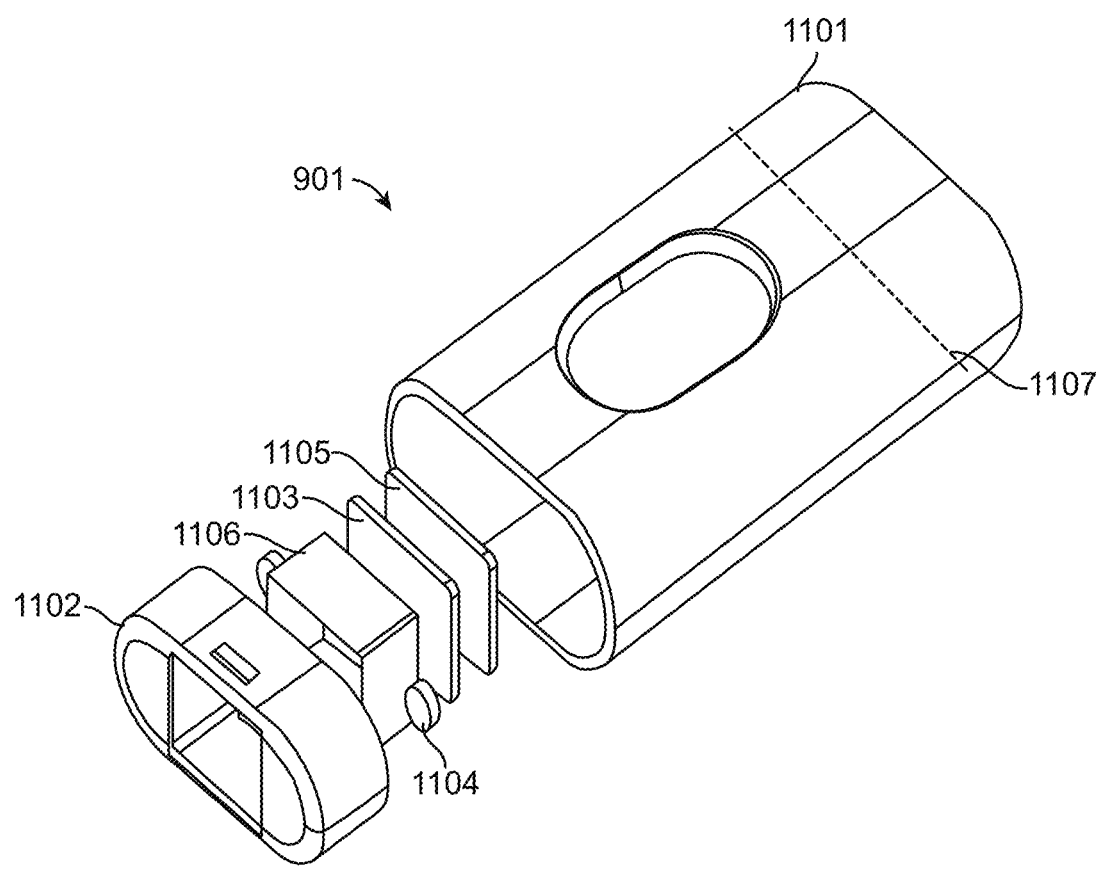
FIG. 11 shows an exploded assembly diagram of a cover.

FIG. 11 shows an exploded view of the cover 901. The cover can have a body 1101 and a base 1102. The base 1102 can house the reflective material 1103. In a full assembly (e.g. not exploded) the base 1102 can be placed into the body 1101. An approximate location of the base in the full assembly is shown by the dotted line 1107. The reflective material can be adhered to an inner surface of the cover with an adhesive 1105. The adhesive 1105 can be a compressible adhesive, for example, a foam. The base can house the reflective material 1103 in a reflector box 1106 embedded in the base. In some instances, the reflector box can have inner walls covered or coated with a reflective layer. The reflective layer material can be metallic, for example gold. The reflective layer can be a diffuse reflector. The reflective layer can be a specular reflector. The reflective layer coating the inner walls can act as a mirror such that the reflective material 1103 appears infinite to an incident light source. The infinite appearance of the reflective material 1103 can reduce or eliminate contamination from materials other than the reflective material 1103. The reflective material 1103 can have a substantially constant reflectivity. The substantially constant reflectivity can be known. The substantially constant reflectivity can be fixed to within about 1% for a constant wavelength light source. In some cases, the substantially constant reflectivity can be fixed to within about 1% for a range of wavelengths. The range of wavelengths can be a range of at least 400 nm. Alternatively, the substantially constant reflectivity can be variable for a range of wavelengths. The substantially constant reflectivity can vary no more than about 10% over a range of wavelengths of at least about 400 nm. The variability of the reflectivity as a function of wavelength can be known.

The base 1102 can further comprise one or more engagement structural features configured to couple or mate to a supports on the spectrometer. In many instances, the engagement structural features can be one or more magnets 1104. When inserted into the cover body 1101, the magnets 1009 on the spectrometer 100 can connect to the magnets 1104 on the base 1102.

The reflective material 1103 can be used to calibrate the spectrometer. The calibration can eliminate or correct for non-uniformities in the light source and/or the spectrometer. The spectrometer can further comprise a processor coupled to the sensor array. The processor can comprise a tangible medium embodying instruction to measure a calibration signal with the cover optically coupled to the sensor array. The processor can comprise instructions to adjust one or more calibration parameter in response to the calibration signal. The calibration parameters can be measurement signal properties. For example, the calibration parameters can be amplitude of a measurement signal comprising one or more a gain of the sensor array or an amount of light energy from the light source. The processor can comprise one or more substantially constant calibration parameters corresponding to the substantially constant reflective material. The processor can be in communication with a memory storage device on or off board the spectrometer that comprises expected or known properties of the constant reflective material. If the spectrometer measures a reflective property outside of the expected or known properties of the constant reflective material the processor can initiate a recalibration or adjustment of one or more calibration parameters. The processor can comprise instructions to adjust the one or more calibration parameters in response to the calibration signal and the one or more substantially constant calibration parameters.

The cover can be provided to calibrate the spectrometer. The calibration can be performed automatically by the spectrometer in response to a user instruction to perform the calibration. A user can instruct the spectrometer to perform the calibration by attaching the cover with the reflective material on the spectrometer, or by a physical user input (e.g. pushing a button or flipping a switch). In the case of automatic calibration, the spectrometer can be calibrated without an input signal from a user. The automatic calibration can be initiated by a processor on or off board the spectrometer. The processor can be configured to detect that the device requires calibration and initiate the calibration.

In many instances an automatic calibration algorithm can be initiated when a user turn the spectrometer on (e.g. presses the power button to complete a battery circuit to provide power to the spectrometer components). The processor can assume that the device is in the cover and aimed at the reflective material in the cover. The assumption can be confirmed by a sensor. For example, a sensor can be a switch indicating that the cover is mounted, or performing a quick reading with or without light source illumination to verify presence of the reflective material. Alternatively, the automatic calibration algorithm can be initiated when stored data in the cloud based storage system 118 for the calibration standard (e.g. reflective material) is older than a threshold age or below a threshold accuracy.

Calibration of the spectrometer can result in a more accurate measurement of a sample material. The cover can comprise a single piece of optically non-transmissive material for calibration. Measurements of the white reference material can be used to remove non-uniformities in the light source and/or the spectrometer when measuring sample materials. The cover can provide the white reference material in a controlled environment for calibration. In some cases, the cover can provide the white reference material in an environment substantially free from ambient light and with a constant and known distance between the sensor and the sample material (e.g. white reference). Other possible materials are glass coated sheets, sand-blasted aluminum and other metals.

Figure 12:
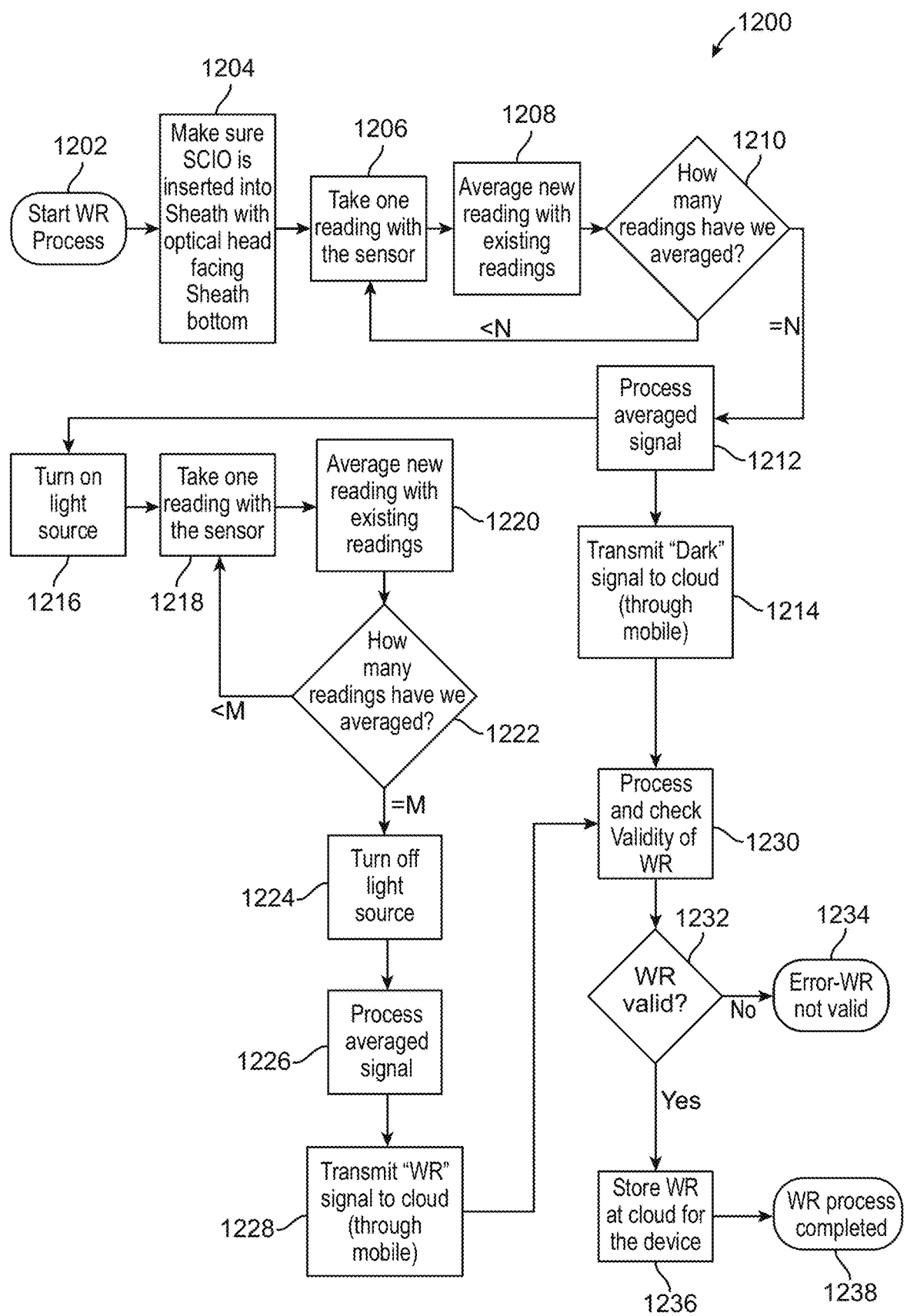
FIG. 12 shows a process flow diagram of a method of calibrating a spectrometer.

FIG. 12 shows a method 1200 that can be performed to automatically, semi-automatically, or manually, initiate and perform a calibration of the spectrometer. In a step 1202, the white reference process can initiate. In a step 1204, the spectrometer can detect that the cover is connected. The cover can comprise a reference reflective material as described herein. In a step 1204, it can be confirmed that the spectrometer is inserted into the cover or sheath and that the optical head of the spectrometer is correctly oriented toward the closed end of the cover. Correct orientation can be towards the bottom of the sheath. In a step 1206, a measurement or reading of the reference reflective material can be taken or collected. In a step 1208, the collected measurement can be averaged with previous measurements or subsequent measurements. In a step 1210, the total number of readings or measurements in the average can be considered. If the number of readings is below a value, N, where N is an integer greater than or equal to zero, step 1206 can be repeated. In a step 1212, which may occur when N is equal to a greater than a chosen threshold value, the average signal or measurement can be processed. In a step 1214, the measurement can be transmitted to a cloud based storage system 118. The signal can be transmitted through a mobile device. In step 1214, the measurement can be a dark measurement. In a step 1216, the light source can be tuned on. In a step 1218, a measurement or reading can be collected or taken with the spectrometer sensor. In a step 1220, the measurement or reading can be averaged with previous measurements or subsequent measurements. In a step 1222, the total number of readings or measurements in the average can be considered. If the number of readings is below a value, M, where M is an integer greater than or equal to zero, step 1218 can be repeated. In a step 1224, the light source can be turned off. In a step 1226, which may occur when N is equal to a greater than a chosen threshold value, the average signal or measurement can be processed. In a step 1228, the measurement can be transmitted to a cloud based storage system 118. The signal can be transmitted through a mobile device. In a step 1230, the dark measurement and the light measurement can be combined to check the validity of a measurement of the reference material (e.g. white reference). In a step 1232, a binary decision can be made regarding the validity of the measurement of the reference material. In a step 1234, an error can indicate that the decision is that the measurement is not valid. In a step 1236, the measurement can be valid and stored on the cloud device 118. In a step 1238, the calibration method can be determined to be complete.

FIG. 12 shows a method 1200 of calibrating a spectrometer. A person of ordinary skill in the art will recognize many variations, alterations and adaptations based on the disclosure provided herein. For example, the order of the steps of the method can be changed, some of the steps removed, some of the steps duplicated, and additional steps added as appropriate. Some of the steps may comprise sub-steps. Some of the steps may be automated and some of the steps can be manual. The processor as described herein may comprise one or more instructions to perform at least a portion of one or more steps of the method 1200.

In many instances, the accessory 909 may comprise structural features that are configured to orient the sample with a defined and repeatable position and orientation relative to the spectrometer light source and/or a spectrometer detector. The accessory can be configured to position and orient a liquid or solid sample. The accessory 909 can comprise a cavity with a structure such as a groove, indentation, dent, depression, hole, ridge, and/or any other physical structure configured to hold a sample with a predetermined orientation relative to the spectrometer. In some cases, the accessory can be configured to center the sample in the cavity. Samples with different shapes can orient in the structural feature in a similar way each time they are measured such that consistency between measurements on the same sample can be achieved. In some cases, the sample can be small relative to the spectrometer. In some cases the sample can be a pill (e.g., paramedical pill). A plurality of accessories can be provided in which each accessory comprises a structural recess sized and shaped to receive a specific object such as a specific pill formulation of a medication.

Figure 13:
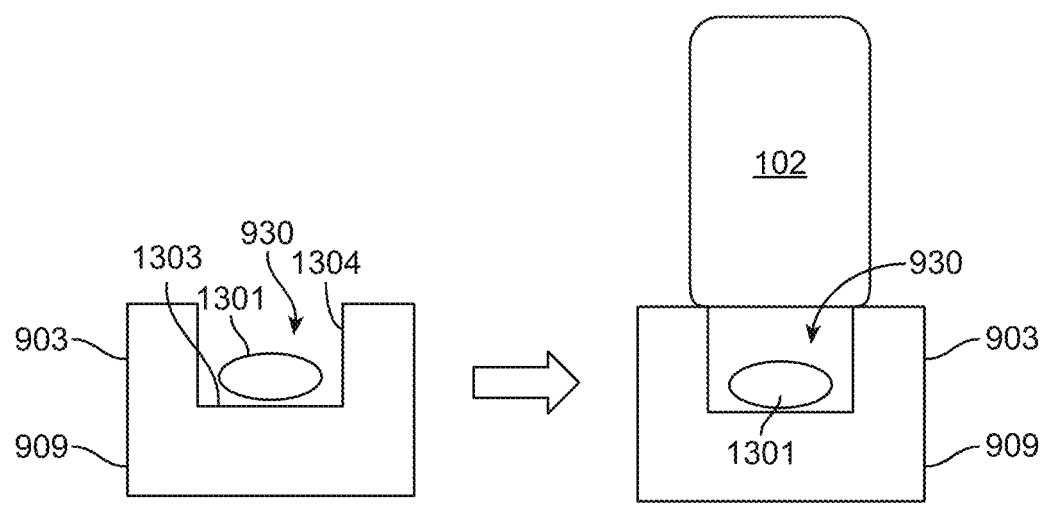
FIG. 13 shows a method of placing a sample in an accessory for measurement of the sample.

FIG. 13 shows a schematic diagram of a pill sample 1301 placed in a sample container 903 comprising an accessory 909. The sample 1301 can be placed in a structure 1303 configured to hold the sample in a predetermined orientation in the accessory relative to the spectrometer during a measurement. The inner walls 1304 of the structure 1303 can be coated with a reflective material. The inner walls of the structure 1303 can be coated with a metallic material. In some cases, at least one inner surface of the structure can be coated with a spectrally flat diffusive material (e.g., Spectralon™). The spectrally flat diffusive material can be behind the sample when the sample is placed in the structure. The inner walls of the structure 1303 can comprise the walls and/or surfaces of the structure 1303 that surround the sample. The accessory 909 can be sized and configured such that the accessory 909 can be placed on a surface while the sample is measured. The surface can comprise a stable surface such as a table or other smooth level surface. To measure the sample 1301 the spectrometer 102 can be fitted on the accessory 909. The spectrometer and the accessory can be connected by complementary magnets provided on the spectrometer and the accessory. When the spectrometer 102 is placed on the accessory 909 the sample 1301 can be enclosed between the spectrometer and the accessory such that ambient light cannot reach the sample. In many instances, the spectrometer is sized and shaped to fit onto the accessory container.

Figure 14A:
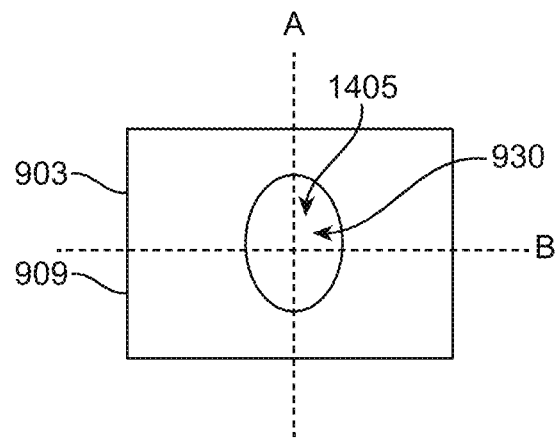
FIG. 14A shows a top view of a structure that can be provided on an accessory configured to orient a sample.
Figure 14B:
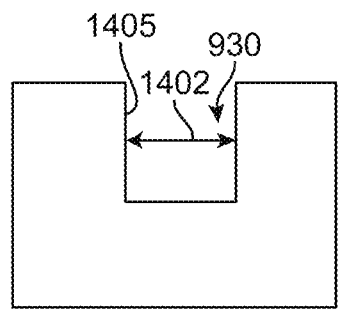
FIG. 14B shows a first cross section view of a structure that can be provided on an accessory configured to orient a sample.
Figure 14C:
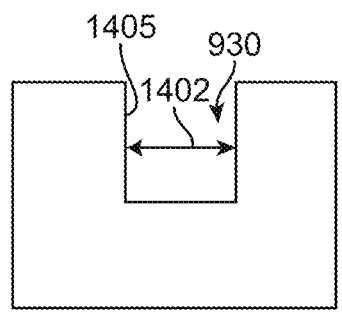
FIG. 14C shows a second cross section view of a structure that can be provided on an accessory configured to orient a sample.
Figure 15A:
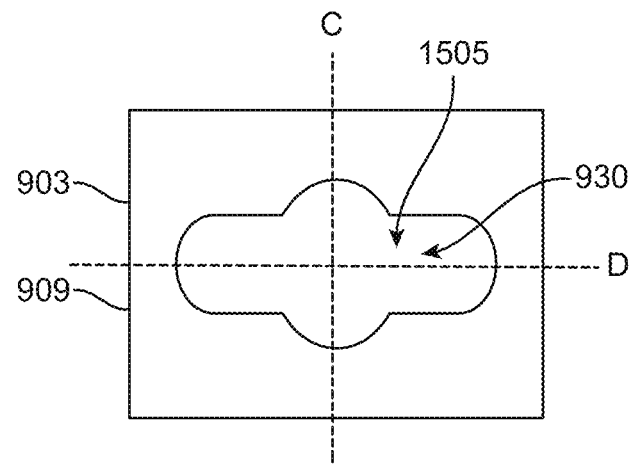
FIG. 15A shows a top view of a structure that can be provided on an accessory configured to orient a sample.
Figure 15B:
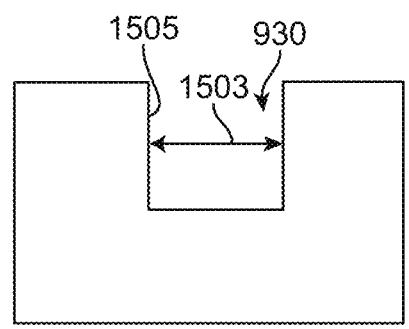
FIG. 15B shows a cross section view of a structure as in FIG. 15A that can be provided on an accessory configured to orient a sample.
Figure 15C:
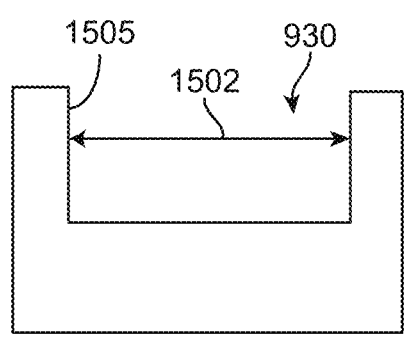
FIG. 15C shows a top view of a structure as in FIGS. 15A and 15B that can be provided on an accessory configured to orient a sample.

FIG. 14A shows a top view of an accessory 909 comprising sample container 903 with structures that can be sized and shaped hold a solid object. In a first case the accessory comprises a first structure with a circular depression 1405 comprising a channel 930. The circular depression can have a diameter 1402 of at least about 1 mm, 5 mm, 10 mm, 15 mm, 20 mm, 25 mm, 30 mm, 35 mm, 40 mm, 45 mm, or 50 mm, for example. The circular depression is shown a in a top view of the accessory. A cross section along line A (shown in FIG. 14B) and a cross section along line B (shown in FIG. 14C) can be identical. The accessory shown in FIG. 14A can be configured to hold a sample with a circular or spherical shape. The accessory shown with FIG. 14A can be configured to hold a circular or spherical pill, for example. In a second case shown in FIG. 15A, the accessory 909 comprising sample container 903 can have a second structure with an irregular depression 1505, comprising a channel 930. The irregular depression can generally be described as a circle laid over an oblong shape. The irregular depression is shown a in a top view in FIG. 15A of the accessory 903. In the second case a cross section along line C (shown in FIG. 15B) and a cross section along line D (shown in FIG. 14C) can have different widths such that one of the depressions shown in the two cross sections is longer than the other. The accessory shown and described by the second case can be configured to hold a sample with a circular, spherical, or oblong shape. The accessory shown and described by the first case can be configured to hold a circular, spherical, or oblong pill.

Figure 16:
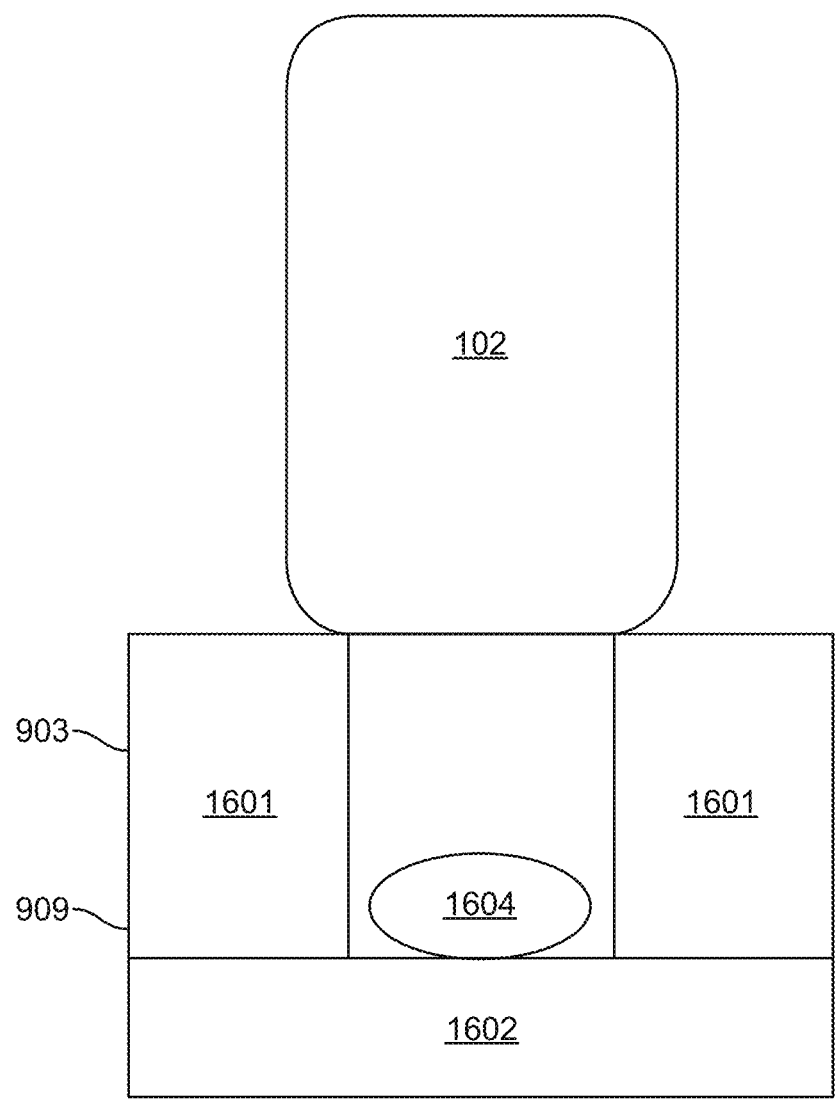
FIG. 16 shows an accessory comprising a plurality of connectable parts.

In some instances, the accessory can comprise a plurality of parts. The parts can be mechanically connected to form the accessory. In some cases the parts can be connected by a magnetic connection to form the accessory 909 comprising container 903. FIG. 16 shows a schematic of an accessory 909 comprising a plurality of connectable parts. In some cases the accessory can comprise more than two connectable parts. In the instances shown in FIG. 16, a first part 1601 can connect to a second part 1602. The first part 1601 and the second part 1602 can be connected by a mechanical fit or a magnetic connection. Additionally, the spectrometer 100 can be fitted on the first part 1601 for measuring of a sample inside the accessory container 903. The spectrometer 102 can be fitted on the first part 1601 with a magnetic connection. The magnetic connection between the spectrometer 102 and the first part 1601 can be stronger than the magnetic connection between the first part 1601 and the second part 1602. In some cases, the sample 1604 can be placed on the second part 1602 before the first part 1601 and the second part 1602 are connected. Placing the sample 1604 on the second part 1602 before the first part 1601 is connected may permit a user to achieve a desired orientation of the sample 1604 on the second part 1602 without being obstructed by the first part 1601.

Figure 17:
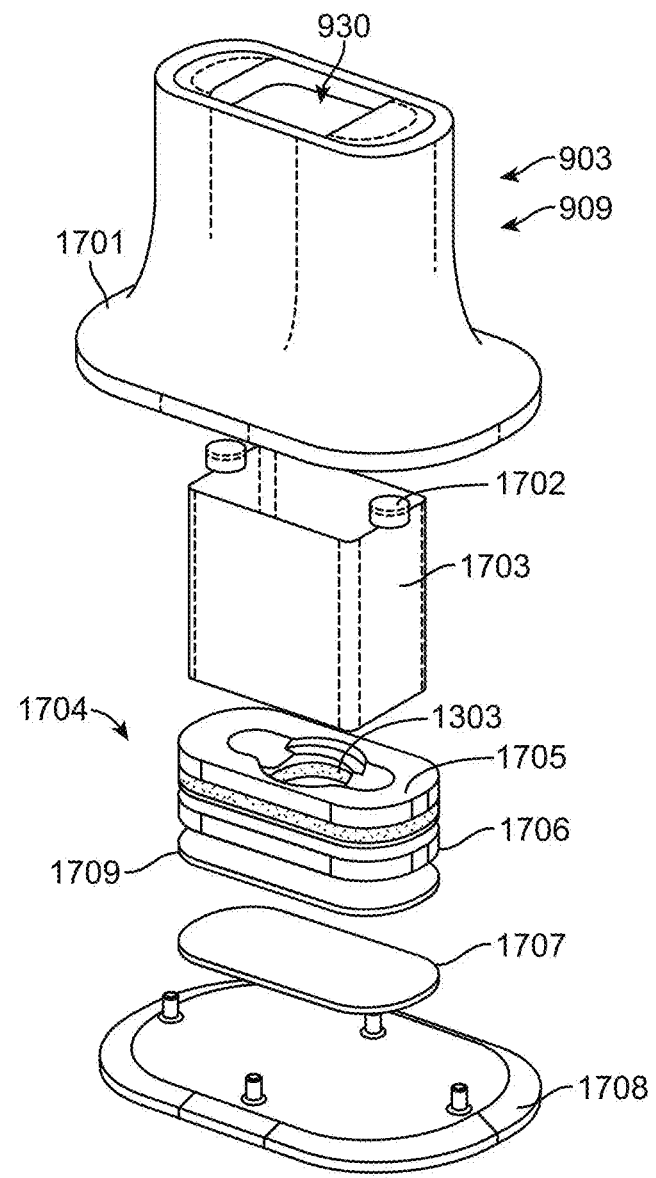

FIG. 17 shows a detailed exploded view of an accessory 909 comprising sample container 903. The accessory can comprise a body 1701 having a channel 930. The body can be a housing for one or more components of the accessory to fit inside of the body 1701. The body can comprise two or more magnets 1702. The two or more magnets can be configured to connect with two or more magnets on a spectrometer or a magnetic surface of the spectrometer when the accessory container 903 is connected to the spectrometer. At least a fraction of the inside of the housing can be coated with or coupled to a reflective box comprising a reflective material 1703. The reflective material 1703 can be a metallic material. When the sample is being measured, the reflective material can reflect at least a fraction of the light emitted by a light source of the spectrometer. The spectrometer housing can comprise an insert 1704 comprising the structure 1303 configured to hold the sample in a predetermined position and orientation.

The insert 1704 can comprise a top surface 1705. The top surface can be a surface that faces the spectrometer during measurement of the sample. The top surface 1705 can be coated with a diffusive and/or spectrally flat coating. Similarly, the bottom surface 1706 of the insert 1704 can comprise a diffusive and/or spectrally flat coating. The bottom surface can be a surface that is behind the sample when the sample is measured by the spectrometer. The insert 1704 can be connected to a base 1708 of the accessory with an adhesive 1707. The base 1708 can connect to the body 1701 of the accessory 903 to fully enclose the components in the accessory 903. A reflective foil 1709 can be placed adjacent to a surface of the structure. The reflective foil can prevent stray ambient light from entering the structure 1303 of the insert 1704. In some cases, a foam (not shown) can be placed between the foil 1709 and the adhesive 1707. The foam can be chosen such that a desired spacing can be provided between the sample and the light source. A thinner foam can be used to increase the distance between the light source and the sample while a relatively thicker foam can be used to decrease the distance between the light source and the sample.

Figure 18A:
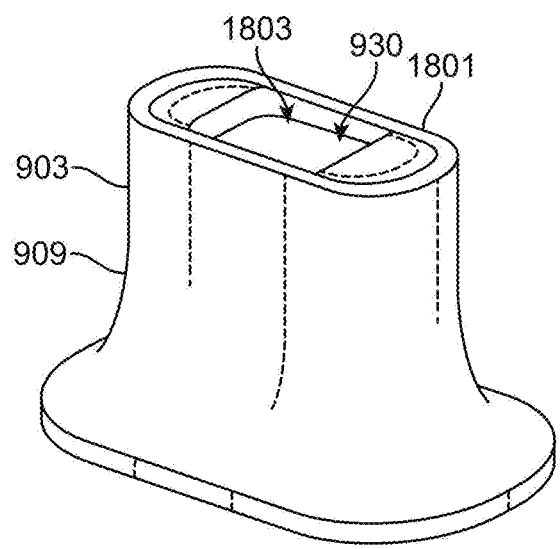
FIGS. 18A and 18B show perspective and a cross sectional diagrams, respectively, of an accessory.
Figure 18B:
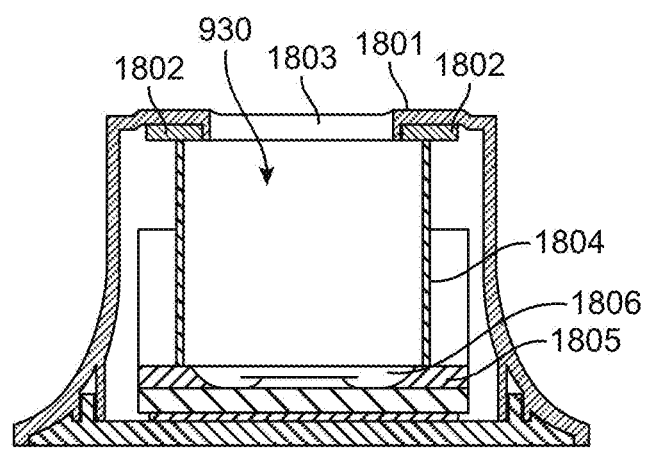

FIG. 18A shows a perspective view of an assembled accessory 909 comprising sample container 903. FIG. 18B shows a cross sectional view of the accessory 909 comprising the container 903. The accessory can have a first end 1801 configured to connect to the spectrometer. The first end can comprise two or more magnets 1802 configured to connect to two or more magnets or a magnetic surface of the spectrometer. The first end 1801 can comprise an opening 1803 through which a sample can be loaded into a channel 930 of the accessory. The inner walls 1804 of the accessory can comprise a reflective coating. A bottom surface 1805 of the accessory can comprise a depression 1806 configured to hold a sample.

In some instances an accessory can be configured to permit measurement of a liquid sample. The liquid sample can comprise a clear or opaque liquid. The liquid sample can comprise a solution, a slurry, a Newtonian fluid, a non-Newtonian fluid, a homogenous mixture, or an inhomogeneous mixture. In some cases the liquid sample can comprise gas bubbles. The liquid sample can comprise a liquid that can be consumed by an animal (e.g., milk, water, carbonated beverage, alcoholic beverage, or juice). The liquid sample can comprise motor oil. The liquid sample can comprise urine. The liquid sample can comprise blood.

The accessory can be formed from a material that is safe for use with food and/or drink. The accessory can be formed from a material that will not contaminate food and/or drink with a chemical that is toxic for consumption by an animal. In some cases, the accessory can be formed from a material that can be washed by hand or in a dishwasher without melting, degrading, and/or breaking. In some instances, the accessory can be formed from a material that is disposable. The disposable material can comprise laminated paper or cardboard.

The inner walls of the channel formed in an accessory or sample container as described herein may comprise a substantially light-absorbing material, such that when the spectrometer is coupled to the accessory, light from the illumination module that hits the inner walls is absorbed by the inner walls rather than reflected back into the channel. For example, the inner walls may be coated with a substantially light-absorbing material, or the inner walls may be formed from a substantially light-absorbing material.

FIG. 19A shows a cross section view of a spectrometer 102 coupled to an accessory 909 comprising a sample container 903 configured to permit measurement of a liquid sample. The accessory 909 can comprise a protective cover 1901. The spectrometer 102 can be fitted in the protective cover 1901 when the spectrometer is connected to the accessory. The spectrometer and the protective cover 1901 can form a liquid tight seal. The spectrometer and the protective cover 1901 can form an air tight seal. When the spectrometer is fitted and connected to the accessory liquid may not be able to permeate a boundary between the spectrometer and the protective cover. The protective cover can prevent liquid from contacting the spectrometer. The protective cover can prevent liquid from damaging the spectrometer. The seal formed between the spectrometer can the protective cover can comprise a gasket, o-ring, or other mechanical seal, for example. The seal formed between the spectrometer and the protective cover can comprise a rubber, Teflon, plastic, or metal seal, for example.

When the spectrometer 102 is coupled to the accessory 909, the spectrometer head 120 can be adjacent to a window 1902 of the accessory. The window can comprise a single window. The window can comprise two or more windows arranged in a single plane. The window can comprise two or more windows arranged on the same surface. The window can be formed from glass, plastic, or any other material configured to permit transmission of light. The window can be configured to permit transmission of light within a predetermined range of wavelengths. In cases where two or more windows are provided on the window, two or more of the windows can be configured to permitted transmission of light in different wavelength ranges, for example.

FIG. 19B shows a surface of a window 1902 that can be provided on the accessory 909. The window can have a convex shape such that any gas bubbles that exist on the window will roll off by buoyancy when the spectrometer is oriented with an elongate axis of the spectrometer extending vertically. Reducing and/or eliminating gas bubbles on the window 1902 can ensure an accurate spectroscopy measurement of the liquid. In some cases one or more channels can be provided on the window to reduce or eliminate gas bubbles.

The window shown in FIG. 19B can comprise a first window 1903 configured to permit illumination light from the spectrometer to enter a liquid sample contained in the accessory 903. The window 1902 may comprise a second window 1904 and a third window 1905. Each of the first window, the second window and the third window can be optically isolated from each other in order to inhibit interference of signals. An opaque material 1913 can extend between the windows in order to inhibit cross-talk and light traveling from one window to the other windows. The windows may comprise energy transmission channels to transmit light to or from the sample. For example, the each window may comprise an energy transmission channel. Each of the channels can be optically isolated from each other. Alternatively or in combination, each of the energy transmission channels may comprise a material to transfer energy in addition to or alternatively to light energy. For example, one or more of the energy transmission channels may comprise a metal to relay heat energy from the sample to the metal and from the metal to an infrared temperature sensor.

The first window 1903 can be arranged adjacent to the illumination window 142 (shown in FIG. 3) of the spectrometer 102 when the spectrometer is fitted in or coupled to the accessory. The first window 1903 can be arranged adjacent to the illumination window 142 of the spectrometer 102 when the spectrometer is fitted in the accessory such that edges of the first window 1903 are aligned with edges of the illumination window 142 of the spectrometer 102. The first window 1903 can be arranged adjacent to the illumination window 142 of the spectrometer 102 when the spectrometer is fitted in the accessory such that a perimeter of the first window 1903 is aligned with a perimeter of the illumination window 142 of the spectrometer 102. The first window 1903 can be arranged adjacent to the illumination window 142 of the spectrometer 102 when the spectrometer is fitted in the accessory such the first window 1903 is aligned with the illumination window 142 of the spectrometer 102. The first window 1903 can be arranged adjacent to the illumination window 142 of the spectrometer 102 when the spectrometer is fitted in the accessory such the first window 1903 is coaxial with the illumination window 142 of the spectrometer 102.

The window 1902 can further comprise second window 1904 configured to permit light to travel from the sample to the spectrometer. The second window 1904 can be arranged adjacent to the spectrometer window 162 (shown in FIG. 3) of the spectrometer 102 when the spectrometer is fitted in or coupled to the accessory. The second window 1904 can be arranged adjacent to the spectrometer window 162 of the spectrometer 102 when the spectrometer is fitted in the accessory such that edges of the second window 1904 are aligned with edges of spectrometer window 162 of the spectrometer 102. The second window 1904 can be arranged adjacent to the spectrometer window 162 of the spectrometer 102 when the spectrometer is fitted in the accessory such that a perimeter of the second window 1904 is aligned with a perimeter of the spectrometer window 162 of the spectrometer 102. The second window 1904 can be arranged adjacent to the spectrometer window 162 of the spectrometer 102 when the spectrometer is fitted in the accessory such the second window 1904 is aligned with the spectrometer window 162 of the spectrometer 102. The second window 1904 can be arranged adjacent to the spectrometer window 162 of the spectrometer 102 when the spectrometer is fitted in the accessory such the second window 1904 is coaxial with the spectrometer window 162 of the spectrometer 102.

The window 1902 can further comprise third window 1905 configured to permit measurement of a temperature of the liquid sample contained in the accessory 909. The third window 1905 can be arranged adjacent to the temperature sensor window 132 of the spectrometer 102 when the spectrometer is fitted in or coupled to the accessory. The third window 1905 can be arranged adjacent to the temperature sensor window 132 (shown in FIG. 3) of the spectrometer 102 when the spectrometer is fitted in the accessory such that edges of the third window 1905 are aligned with edges of temperature sensor window 132 of the spectrometer 102. The third window 1905 can be arranged adjacent to the temperature sensor window 132 of the spectrometer 102 when the spectrometer is fitted in the accessory such that a perimeter of the third window 1905 is aligned with a perimeter of the temperature sensor window 132 of the spectrometer 102. The third window 1905 can be arranged adjacent to the temperature sensor window 132 of the spectrometer 102 when the spectrometer is fitted in the accessory such the third window 1905 is aligned with the temperature sensor window 132 of the spectrometer 102. The third window 1905 can be arranged adjacent to the temperature sensor window 132 of the spectrometer 102 when the spectrometer is fitted in the accessory such the third window 1905 is coaxial with the temperature sensor window 132 of the spectrometer 102.

The third window 1905 can be configured to permit transmission of an optical temperature measurement signal. The optical temperature measurement signal can comprise light with a wavelength in a range of about 1 µm to about 100 µm. The optical temperature measurement signal can comprise light with a wavelength in a range of about 1 µm to about 50 µm. The optical temperature measurement signal can comprise light with a wavelength in a range of about 5

μinto about 25 μm. The optical temperature measurement signal can comprise light with a wavelength in a range of about 4 μm to about 8 μm. The third window 1905 can comprise a germanium window, for example. The third window can be transmissive to light with a wavelength within the range of the optical temperature measurement signal wavelength range.

During measurement of a liquid sample, the spectrometer 102 fitted in the accessory 909 can be dipped into a liquid. Dipping the spectrometer into the liquid can reduce specular reflection of illumination light from a liquid surface. In some cases, specular reflections of illumination light from a liquid surface can confuse or inhibit acquisition of an accurate spectrometry measurement. In some cases, if the spectrometer is not dipped into the liquid transition of illumination from the liquid to air between the spectrometer and a surface of the liquid can cause light refraction. Light refraction can confuse or inhibit acquisition of an accurate spectrometry measurement. Dipping the spectrometer in the liquid can avoid the issues of specular reflections and/or light refraction that can occur as a result of illumination off of the surface of the liquid. When a user dips the attachment coupled to the spectrometer in a liquid the user can perform one or more steps to decrease formation of gas bubbles between the accessory window 1902 and the liquid for sampling. In some cases, a user can decrease formation of gas bubbles between the accessory window 1902 and the liquid for sampling by first dipping the accessory in with an elongate axis of the spectrometer at an angle less than 90° relative to the surface of the liquid.

When the spectrometer 102 fitted in the accessory 909 is dipped in a liquid for measurement of the liquid, a volume of liquid can fill a space 1906 that forms between the window 1902 and the reflective element 1907. In some cases, the space 1906 can be fully enclosed by opaque walls to prevent ambient light from interfering with a spectroscopy measurement. The walls may comprise one or more openings, for example a plurality of openings, to allow liquid to enter the space and gas to exit the space 1906 defined by the walls of the measurement chamber. The inside of a wall can be a side that contacts the liquid volume enclosed by the walls. The inside of a wall can be coated with a reflective coating. Alternatively the inside of a wall can be coated with a material that absorbs light. The inside of a wall can be coated with a material that does not reflect light. At least one of the walls can be opened and/or removed prior to a measurement to permit liquid to enter the space. At least one of the walls can be opened by a hinge connection. In some instances, at least one of the walls can comprise one or more openings configured to permit liquid to enter the space 1906. In some cases, the space 1906 can be open on at least one side to permit easy flow of liquid into the space for sampling. The space 1906 can be free of walls, in some cases, posts can connect the accessory to the platform. The posts will be described in detail elsewhere herein.

The reflective element 1907 can comprise a material that is a diffuse reflector. The diffuse reflector can be embedded in a platform 1912, for example placed in a recess of platform 1912. The reflective element 1907 can comprise a material that is a specular reflector. The reflective element can comprise a material that is both a specular and diffuse reflector. The reflective element can comprise a smooth coating (e.g., polished gold coating) to permit specular reflection. A protective layer 1909 can be provided over the reflective element to protect the reflective element from the liquid. A protective layer 1909 can be provided over the reflective element to prevent the reflective element from contacting the liquid. A protective layer 1909 can be provided over the reflective element to prevent the reflective element from getting wet. The protective layer 1909 can be transparent. The protective layer 1909 can be glass. The protective layer 1909 can be plastic. The protective layer 1909 can be a cured transparent resin. In some cases, the reflective material can be formed from a material that is resistant to liquids. The reflective material can be formed from a material that can be exposed to a liquid without breaking, eroding, reacting, or becoming unusable, for example. In some cases, the reflective element can be formed from opal glass or sand blasted metal (e.g., aluminum, steel, copper, brass, or iron). In cases where the reflective element is resistant to liquids the protective layer can be omitted. In some cases, the reflective element can comprise a diffuser placed over a reflecting substrate.

In some configurations, the reflective element 1907 may comprise a diffuser placed over a light-blocking and light-absorbing material (such as an anodized aluminum foil or plate). A diffuser placed over a light-absorbing substrate may produce a reflectance spectral response with better flatness and stability than a diffuser placed over a reflecting substrate. If the diffuser is thick enough, there may be no need for a separate substrate as the forward transmitted light may be weak enough, and the backscattering strong enough.

Illumination from the illumination module can illuminate a volume of liquid contained in the space 1906 that fills with the volume of liquid when the spectrometer fitted in the accessory is dipped in a liquid. The reflective layer can increase the amount of light reflected towards the spectrometer. The reflective layer can increase the intensity of light that is reflected towards the spectrometer. The reflective layer can increase accuracy by increasing signal from liquids that are transparent (e.g., transparent to light in the IR range). The reflective layer can increase accuracy by increasing signal from liquids with low scattering characteristics.

The reflecting element 1907 may be particularly helpful for the measurement of spectra of essentially clear or lucid liquids (e.g., measurement of the percentage of alcohol in Vodka), and may be of relatively lesser importance for the measurement of highly diffusive liquids (e.g., measurement of the percentage of fat in milk). The use of a reflecting element or base for the measurement of clear liquids can be important both for minimizing the reflection of light from background objects (such as the base of the liquid sample container) and for increasing the intensity of light passing from the illumination module through the liquid and into the spectrometer.

A distance 1910 between the window 1902 and the reflective element 1907 can influence the accuracy of a spectroscopy measurement. The distance 1910 can define the volume of the liquid contained in the space 1906. In some cases, the distance 1910 can be adjustable. Two or more posts 1911 can connect the window 1902 of the accessory and the reflective element. The posts can be permanently or removable attached to either or both of the accessory and a platform 1912 comprising the reflective element. In some cases, a first set of posts can be disconnected from the platform and the accessory and replaced with a second set of posts with a longer or shorter length relative to the first set of posts.

Figure 20:
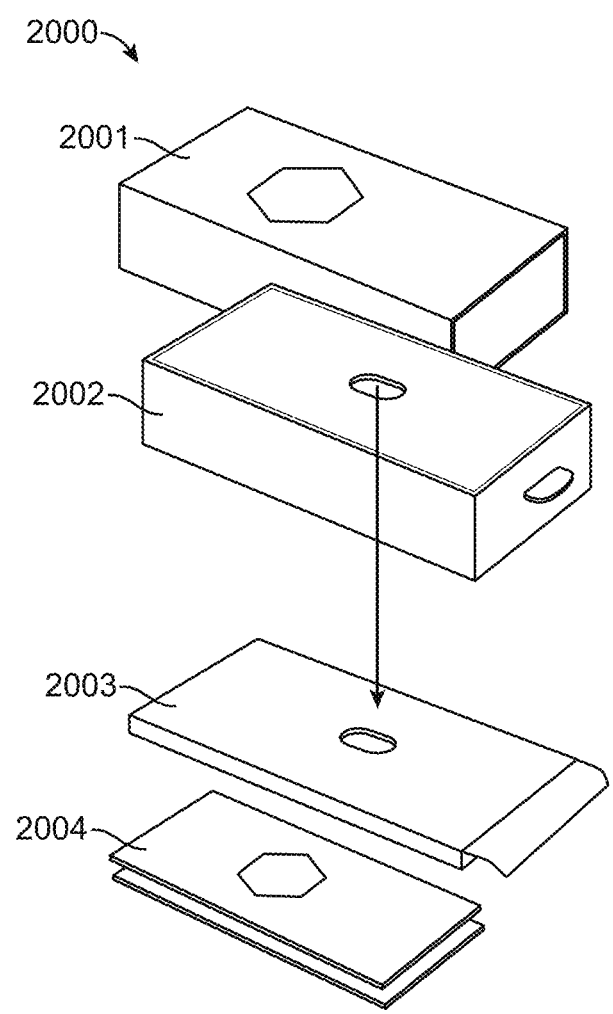
FIG. 20 shows a package in which a spectrometer kit can be housed.

The spectrometer 102 can be packed for sale and/or delivery. The package can comprise the spectrometer. The package can comprise one or more accessories 909 for use with the spectrometer. FIG. 20 shows a package that can house a kit comprising the spectrometer and one or more accessories. The accessories can comprise any of the accessories described herein. The accessories can comprise accessories for measuring of liquids, measuring of solids, measuring of pills, and/or calibration of the spectrometer.

The package 2000 can comprise an outer box 2001. An inner box 2002 can slide into the outer box 2001. An inner box 2002 can be size and shaped such that it fits into the outer box 2001. A tray 2003 can additionally be fitted in the outer box. Alternatively the tray can be fitted in the inner box. The spectrometer and one or more accessories can be contained in the inner box 2002. Instructions for use 2004 can be fitted in the tray.

Figure 21:
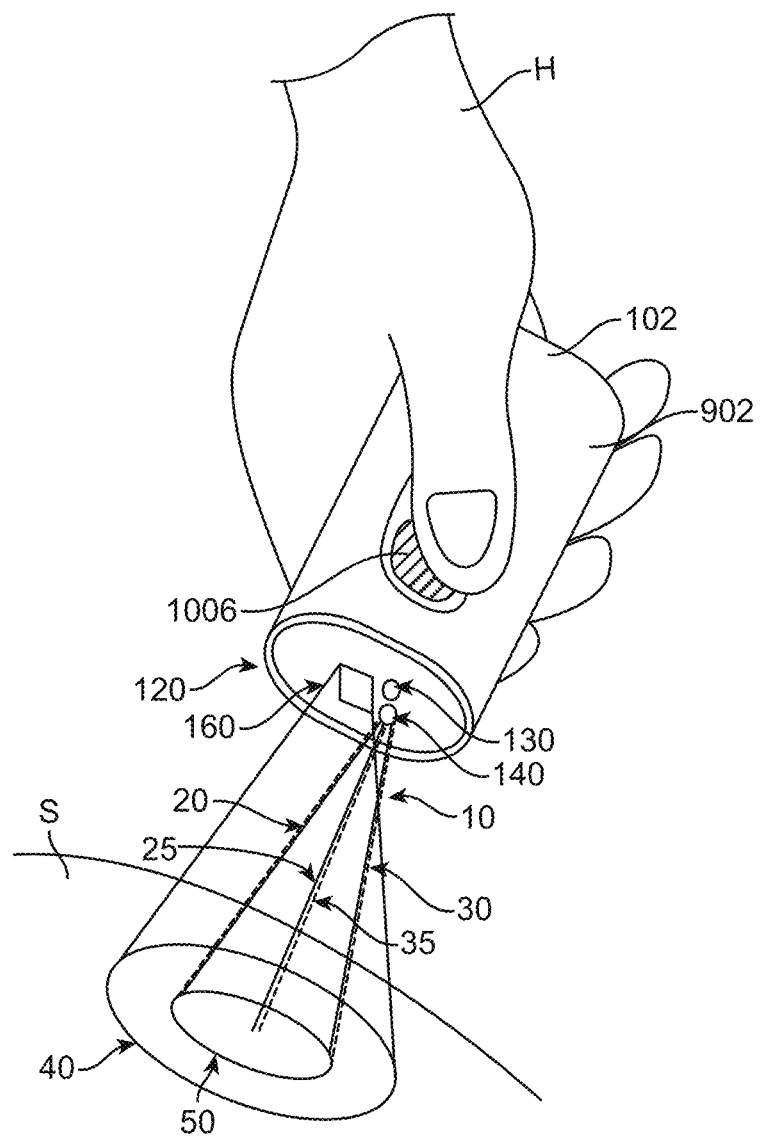
FIG. 21 shows an isometric view of a compact hand held spectrometer.

Referring now to FIG. 21, a user may initiate a measurement of a sample material S using the spectrometer 102 by interacting with a user input supported with a container 902 of the spectrometer. Although the spectrometer is shown without an accessory covering the measurement end of the spectrometer, one or more accessories as described herein can be placed on the measurement end and the spectrometer used similarly. The user input may, for example, comprise an operating button 1006. The container 902 may be sized to fit within a hand H of a user, allowing the user to hold and aim the spectrometer at the sample material, and manipulate the user input with the same hand H to initiate measurement of the sample material. The container 902 can house the different parts of the spectrometer such as the spectrometer module 160, illumination module 140, and sensor module 130. The spectrometer module may comprise a detector or sensor to measure the spectra of the sample material within a field of view 40 of the detector or sensor. The detector may be configured to have a wide field of view. The illumination module may comprise a light source configured to direct an optical beam 10 to the sample material S within the field of view 40. The light source may be configured to emit electromagnetic energy, comprising one or more of ultraviolet, visible, near infrared, or infrared light energy. The light source may comprise one or more component light sources. The field of view 40 can define the portion of the sample material S from which the spectral data is collected by the spectrometer 102. The illumination module may further comprise one or more optics coupled to the light source to direct the optical beam 10 toward the sample material S. The one or more optics may comprise one or more of a mirror, a beam splitter, a lens, a curved reflector, or a parabolic reflector, as described in further detail herein. The spectrometer 102 may further comprise circuitry coupled to the detector and the light source, wherein the circuitry is configured to transmit the optical beam 10 in response to user interactions with the user input using hand H holding the spectrometer. When a user initiates a measurement of a sample material S using the spectrometer 102, for example by pressing the operating button 1006 with hand H, the spectrometer emits an optical beam 10 toward the sample material within the field of view 40. When the optical beam 10 hits the sample material S, the light may be partially absorbed and/or partially reflected by the sample material; alternatively or in combination, optical beam 10 may cause the sample material to emit light in response. The sample emission, which may comprise at least a portion of the optical beam 10 reflected back by the sample and/or light emitted by the sample in response to the optical beam 10, is sensed by the detector or sensor of the spectrometer module 160. The spectrometer module 160 consequently generates the spectral data of the sample material as described in further detail herein.

The spectrometer 102 may be configured to begin measurement of a sample material S with just ambient light, without the optical beam 10. After completing the measurement with ambient light only, the illumination module 140 of the spectrometer 102 can generate the optical beam 10, and the spectrometer module 160 can begin measurement of the sample material with the optical beam 10. In this case, there may be a brief time lapse between the initiation of a measurement, for example by a user pressing the operating button 1006, and the generation of the optical beam 10 and the visible portions thereof. The ambient light-only measurement can be used to reduce or eliminate the contribution of ambient light in the spectral data of the sample material S. For example, the measurement made with ambient light only can be subtracted from the measurement made with the optical beam 10.

A portion of the optical beam 10 that is reflected from the sample material S may be visible to the user; this visible, reflected portion of optical beam 10 may define the measurement area 50 of the sample material S. The measurement area 50 of the sample may at least partially overlap with and fall within the field of view 40 of the detector of the spectrometer. The area covered by the field of view 40 may be larger than the visible area of the sample illuminated by the optical beam 10, or the measurement area 50 defined by the visible portion of the optical beam 10. Alternatively, the field of view may be smaller than the optical beam, for example. In many configurations, the field of view 40 of the detector of the spectrometer module is larger than the area illuminated by the optical beam 10, and hence the measurement area 50 is defined by the optical beam 10 rather than by the field of view 40 of the detector.

The visible portion of optical beam 10 may comprise one or more wavelengths corresponding to one or more colors visible to the user.

The light output of the visible portion of optical beam 10 may vary depending on the type of light source. In some cases, the visible light output of optical beam 10 may vary due to the different luminous efficacies of different types of light source. For example, blue light-emitting diode (LED) may have an efficacy of about 40 lumens/W, a red LED may have an efficacy of about 70 lumens/W, and a green LED may have an efficacy of about 90 lumens/W. Accordingly, the visible light output of optical beam 10 may vary depending on the color or wavelength range of the light source.

The light output of the visible portion of optical beam 10 may also vary due to the nature of interactions between the different components of a light source. For example, the light source may comprise a light source combined with an optical element configured to shift the wavelength of the light produced by the first light source, as described in further detail herein. In this instance, the visible light output of the visible portion of optical beam 10 may vary depending on the amount of the light produced by the light source that is configured to pass through the optical element without being absorbed or wavelength-shifted, as described in further detail herein.

The optical beam 10 may comprise a visible aiming beam 20. The aiming beam 20 may comprise one or more wavelengths corresponding to one or more colors visible to the user, such as red, orange, yellow, blue, green, indigo, or violet. Alternatively or in combination, the optical beam 10 may comprise a measurement beam 30, configured to measure the spectra of the sample material. The measurement beam 30 may be visible, such that the measurement beam 30 comprises and functions as a visible aiming beam. The optical beam 10 may comprise a visible measurement beam 30 that comprises a visible aiming beam. The measurement beam 30 may comprise light in the visible spectrum, non-visible spectrum, or a combination thereof. The aiming beam 20 and the measurement beam 30 may be produced by the same light source or by different light sources within the illumination module 140, and can be arranged to illuminate the sample material S within the field of view 40 of the detector or sensor of the spectrometer 102. The visible aiming beam 20 and the optical beam 30 may be partially or completely overlapping, aligned, and/or coaxial.

The visible aiming beam 20 may comprise light in the visible spectrum, for example in a range from about 390 nm to about 800 nm, which the user can see reflected on a portion of the sample material S. The aiming beam 20 can provide basic visual verification that the spectrometer 102 is operational, and can provide visual indication to the user that a measurement is in progress. The aiming beam 20 can help the user visualize the area of the sample material being measured, and thereby provide guidance the user in adjusting the position and/or angle of the spectrometer 102 to position the measurement area over the desired area of the sample material S. The aiming beam 20 may be configured with circuitry to be emitted throughout the duration of a measurement, and automatically turn off when the measurement of the sample material S is complete; in this case, the aiming beam 20 can also provide visual indication to the user of how long the user should hold the spectrometer 102 pointed at the sample material S.

The visible aiming beam 20 and the measurement beam 30 may be produced by the same light source, wherein the visible aiming beam 20 comprises a portion of the measurement beam 30. Alternatively, the aiming beam 20 may be produced by a first light source, and the measurement beam 30 may be produced by a second light source. For example, the measurement beam 30 may comprise an infrared beam and the aiming beam 20 may comprise a visible light beam.

The measurement beam 30 may be configured to illuminate the measurement area of the sample S, and the aiming beam 20 may be configured to illuminate an area of the sample overlapping with the measurement area, thereby displaying the measurement area to the user. One or more optics of the illumination module, such as a lens or a parabolic reflector, may be arranged to receive the aiming beam 20 and the measurement beam 30 and direct the aiming beam and measurement beam toward the sample material S, with the aiming beam and measurement beam overlapping on the sample. The aiming beam 20 may be arranged to be directed along an aiming beam axis 25, while the measurement beam 30 may be arranged to be directed along a measurement beam axis 35. The aiming beam axis 25 may be co-axial with measurement beam axis 35.

The sensor or detector of the spectrometer module 160 may comprise one or more filters configured to transmit the measurement beam 30 but inhibit transmission of the aiming beam 20. In many configurations, the spectrometer module comprises one filter configured to inhibit transmission of visible light, thereby inhibiting transmission of portions of the aiming beam 20 and measurement beam 30 reflected from the sample that comprise visible light. In some configurations, the spectrometer module 160 may comprise a plurality of optical filters configured to inhibit transmission of a portion of the aiming beam 20 reflected the sample material S, and to transmit a portion of the measurement beam 30 reflected from the sample. In configurations of the spectrometer module comprising a plurality of optical channels, the spectrometer module may comprise a plurality of filters wherein each optical filter corresponds to an optical channel. Each filter may be configured to inhibit transmission of light within a specific range and/or within a specific angle of incidence, wherein the filtered specific range or specific angle of incidence may be specific to the corresponding channel. In some configurations, each optical channel of the spectrometer module may comprise a field of view. The field of view 40 of the spectrometer module may hence comprise a plurality of overlapping fields of view of a plurality of optical channels. The aiming beam and the measurement beam may overlap with the plurality of overlapping fields of view on the sample S. In some configurations, a diffuser may be disposed between the plurality of optical filters and the incident light from the sample, wherein each optical filter corresponds to an optical channel. In such configurations, the plurality of optical channels may comprise similar fields of view, each field of view at least partially overlapping with the fields of view of other optical channels, wherein the spectrometer substantially comprises a field of view of ±1-90°.

Optionally, the visible aiming beam 20 may be produced by a light source separate from the illumination module 140. In this case, the separate light source may be configured to produce the aiming beam such that the aiming beam illuminates a portion of the sample material that overlaps with the measurement area of the sample.

Figure 22:
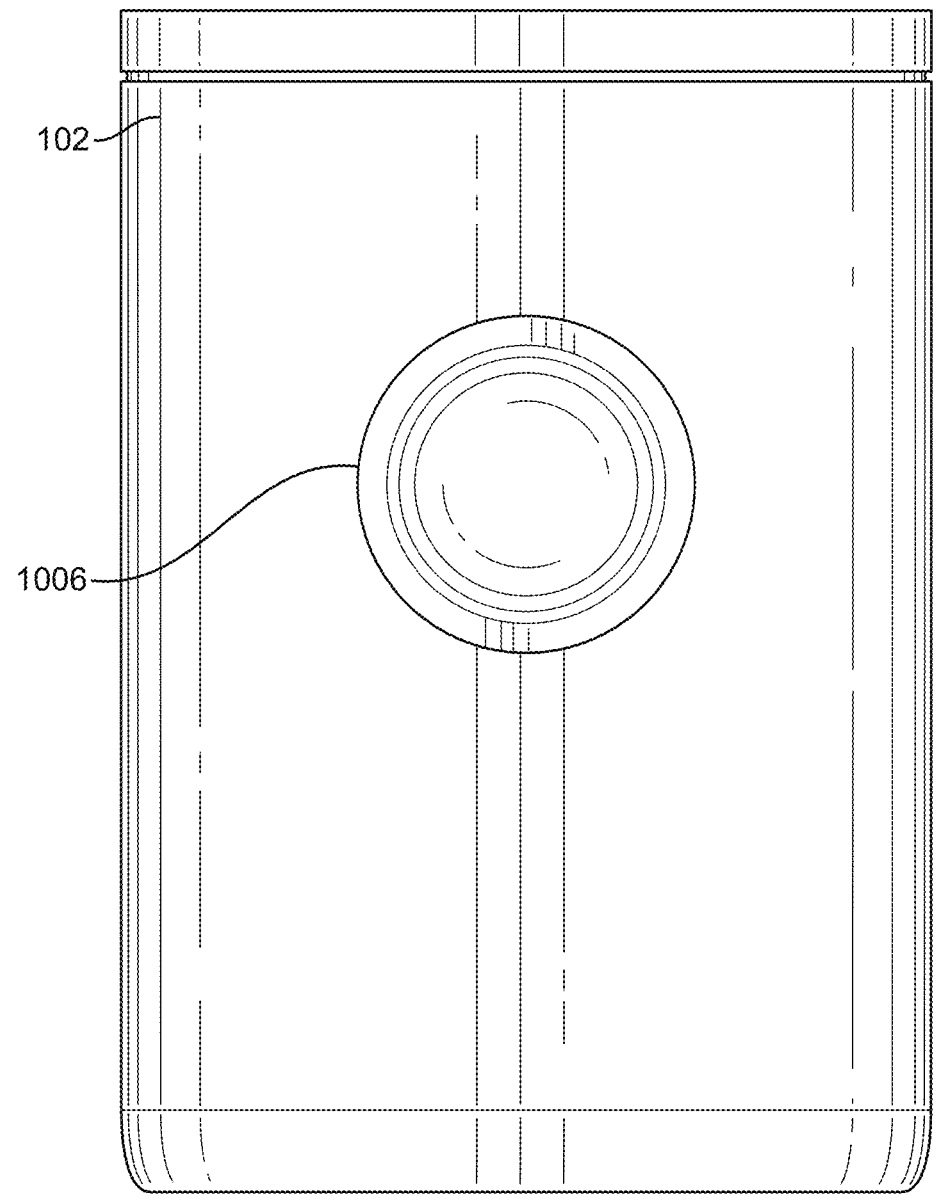
FIG. 22 shows a top view of a spectrometer showing an operation button.

FIG. 22 shows a top view spectrometer 102. The spectrometer can comprise an operating button 1006. An operating button 1006 can allow a user to control battery power to one or more components in the spectrometer. In some cases, a user can power a spectrometer on and off by manipulating the operating button. An operating button can be a compressible button, switch, or touchscreen (e.g. capacitive screen).

Figure 23:
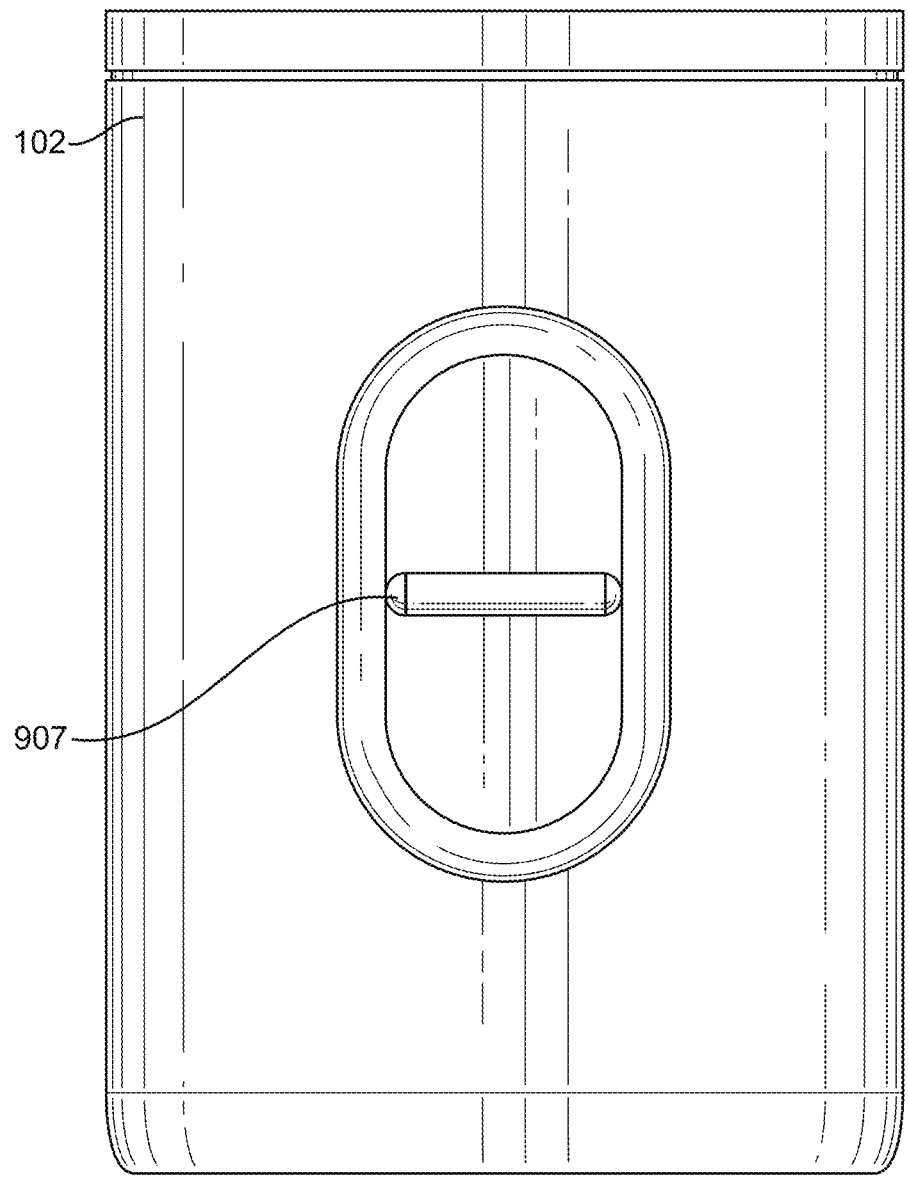
FIG. 23 shows a bottom view of a spectrometer showing a protrusion.

FIG. 23 shows a bottom view of a spectrometer 102 opposed a side of a spectrometer comprising an operating button. The spectrometer can comprise a protrusion 907 on the spectrometer. When the spectrometer is fitted in a cover or sheath the protrusion may be accessed through the one or more openings in the sheath. The protrusion 907 can comprise a raised bump, raised line, a groove, a depression, a textured surface, a nub, and/or a raised structural feature that can be gripped by a user's hand and/or finger. A user may push the spectrometer 100 out of the container when the sheath is placed in the container by pushing and/or pulling on the protrusion 907 to apply a shear force to the spectrometer. In some cases, the protrusion can be recessed in a surface of the spectrometer such that the protrusion does not interfere with the sheath (e.g., container) when the spectrometer is pushed into or pulled out of the container. The protrusion can be on a side of the spectrometer that comprises the button 1006. The protrusion can be on a side of the spectrometer that does not comprise the protrusion. The protrusion can be on a side of the spectrometer opposite the side of the spectrometer that comprises the button.

Figure 24:
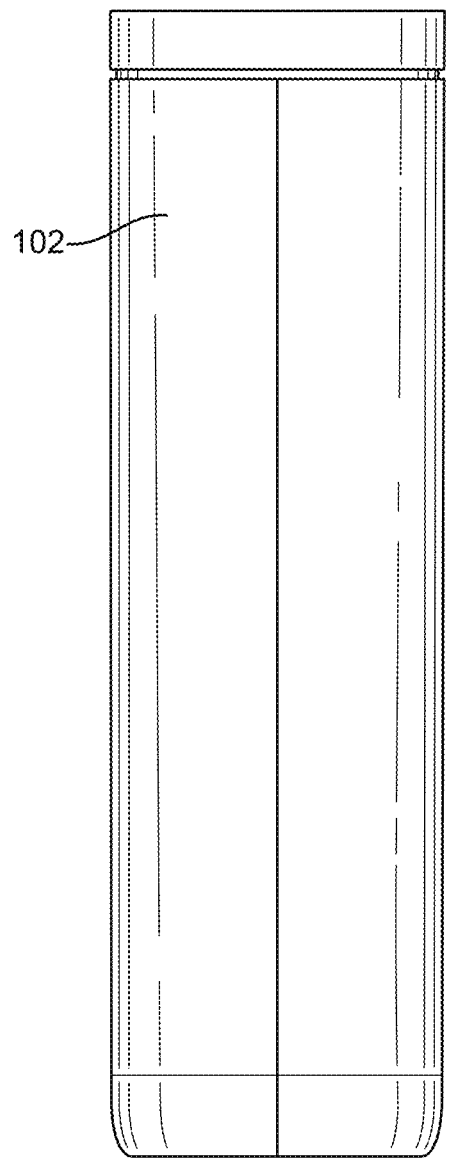
FIG. 24 shows a side view of a spectrometer.

FIG. 24 shows a side view of the spectrometer 102.

Figure 25:
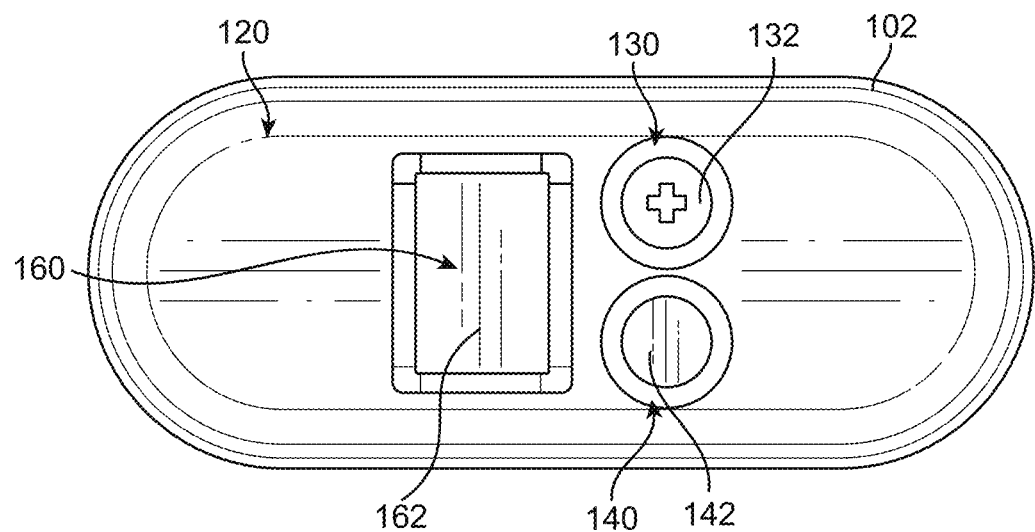
FIG. 25 shows an end view of spectrometer head.

FIG. 25 shows an end view of the spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a temperature sensor window 132, and the illumination module 140 can comprise an illumination window 142.

Figure 26:
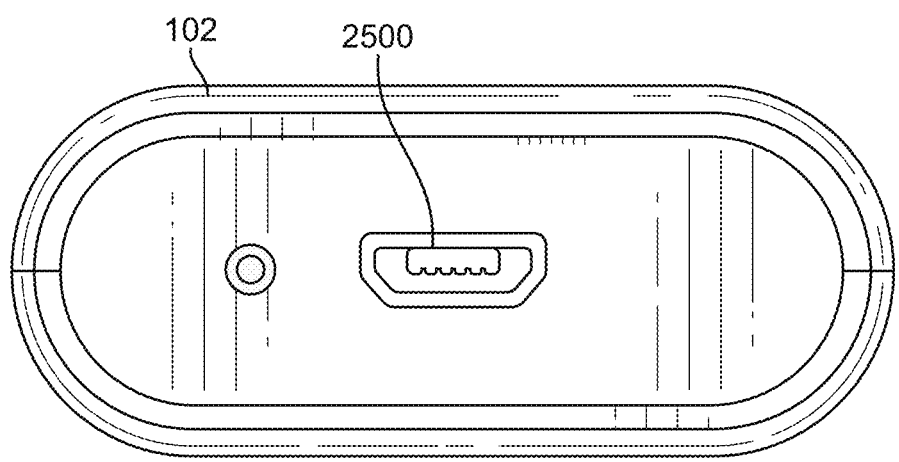
FIG. 26 shows an end of a spectrometer comprising a charging contact.

FIG. 26 shows an end of the spectrometer 102 comprising a charging port 2500. The charging port can provide an electrical connection between an energy storage device (e.g., battery) housed in the spectrometer and an energy source configured to provided energy to the energy storage device. In some cases, the charging port can be a USB charging port. In some cases, the charging port can comprise a pin electrical connection. The electrical connection can be configured to be fitted on a charging cradle. In some cases, the charging port 2500 can be provided on a side of the spectrometer opposite a side of the spectrometer comprising the spectrometer head.

Figure 27:
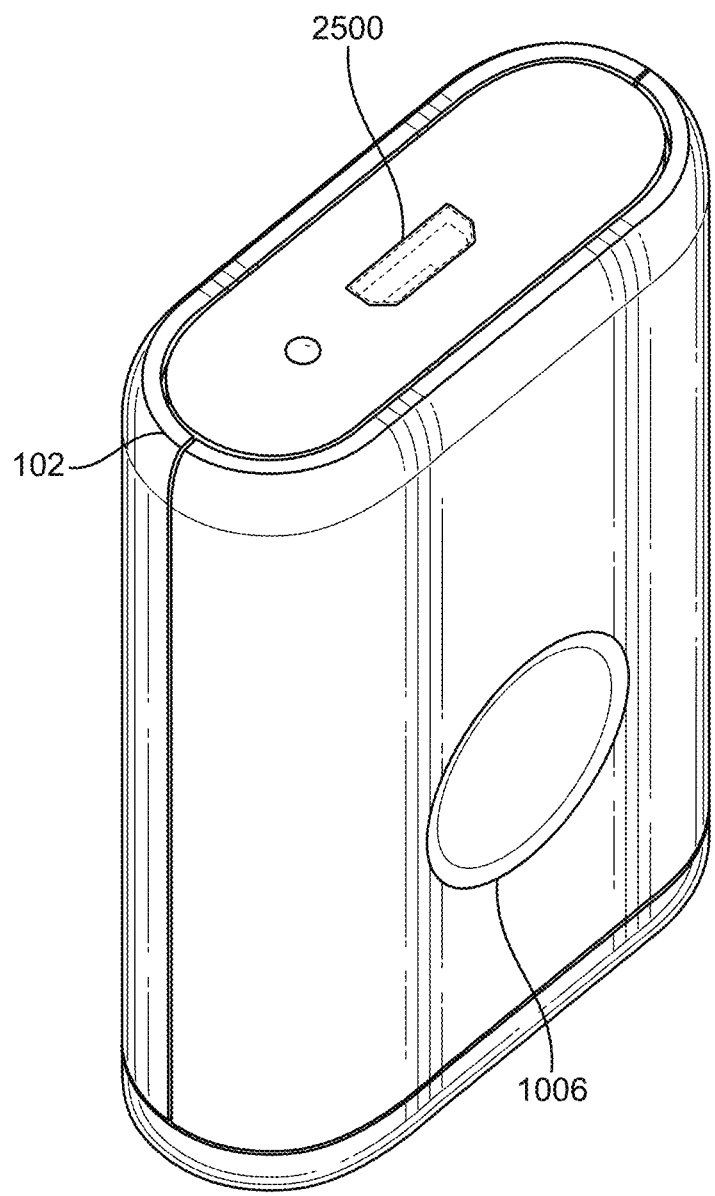
FIG. 27 shows an isometric view of a spectrometer with a side comprising a charge contact facing up.

FIG. 27 shows an isometric view of the spectrometer 102.

Figure 28:
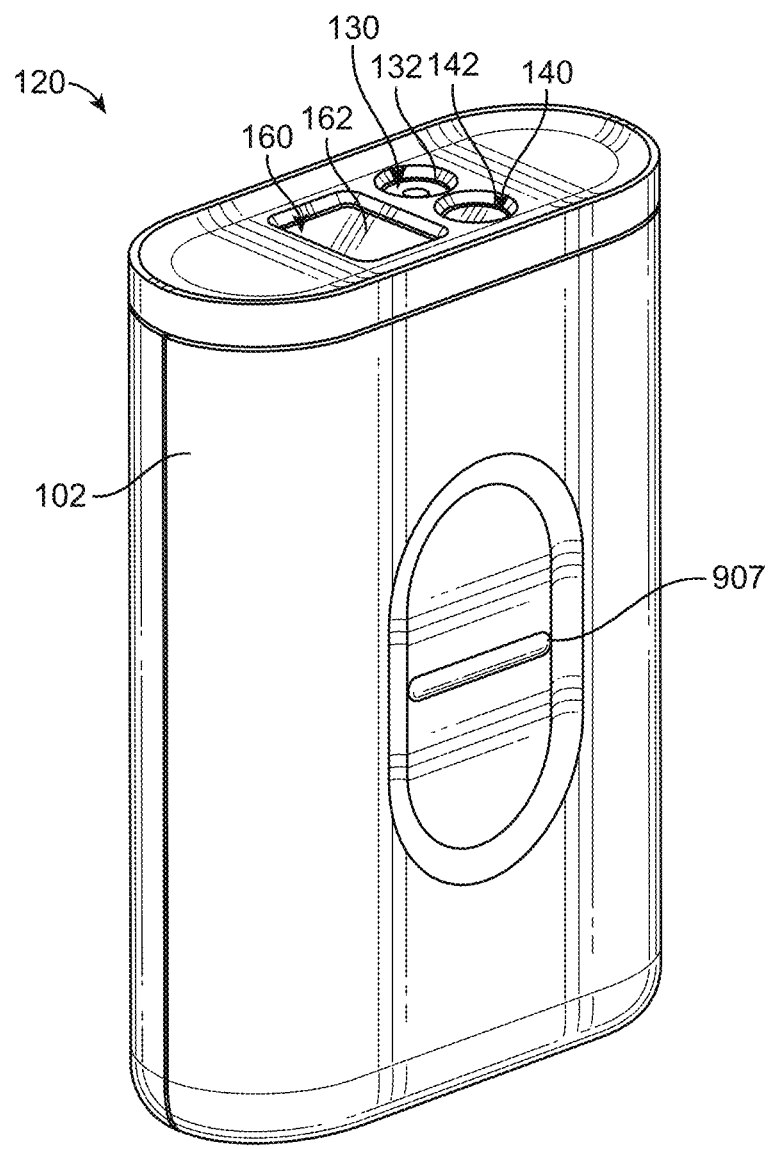
FIG. 28 shows an isometric view of a spectrometer with a side comprising a spectrometer head facing up.

FIG. 28 shows another isometric view of the spectrometer showing the spectrometer head 120 and the protrusion 907.

Figure 29:
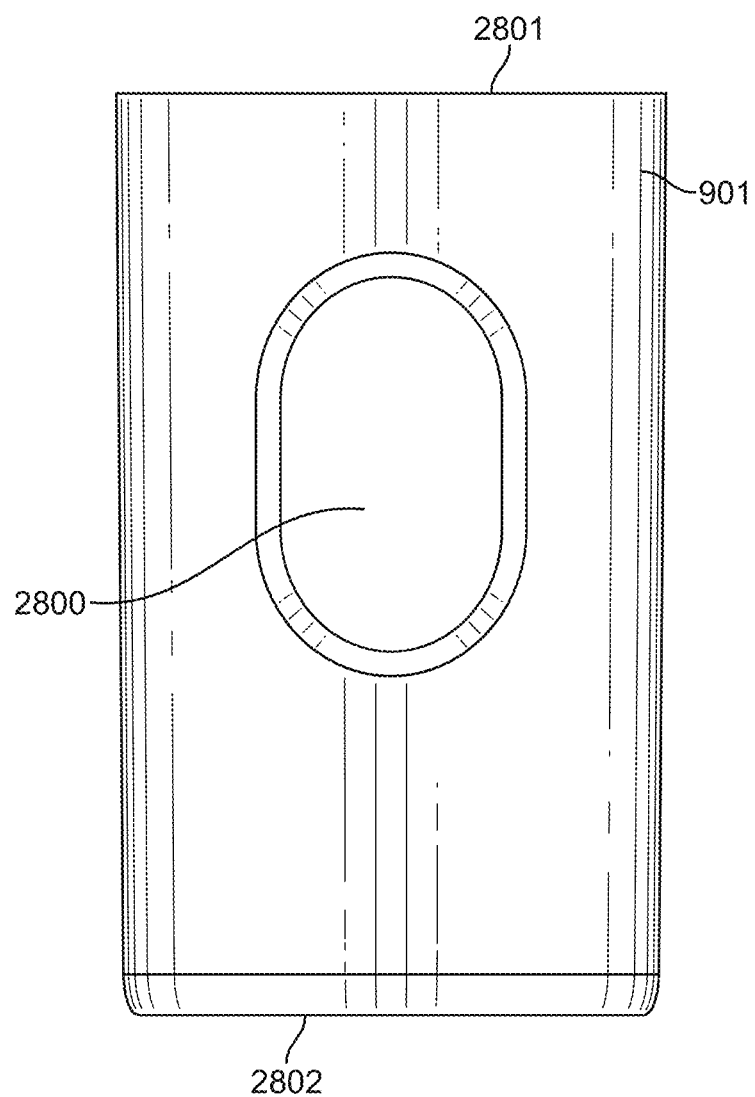
FIG. 29 shows a top view of a cover showing a hole.

FIG. 29 shows a top view of cover 901 configured to house the spectrometer. The spectrometer appears similarly in bottom view and can be symmetrical, for example. The cover can be a protective cover for the spectrometer. The cover can provide a controlled environment for measuring of one or more samples with the spectrometer. The cover can provide a controlled environment for calibration the spectrometer. The cover 901 can comprise one or more holes 2800 through which the spectrometer can be accessed when the spectrometer is fitted in the cover. The button of the spectrometer can be accessed through the hole. The protrusion of the spectrometer can be accessed through the hole. The cover can have an open end 2801 through which the spectrometer can enter and exit the cover. The cover can have a closed end 2802 opposite the open end.

Figure 30:
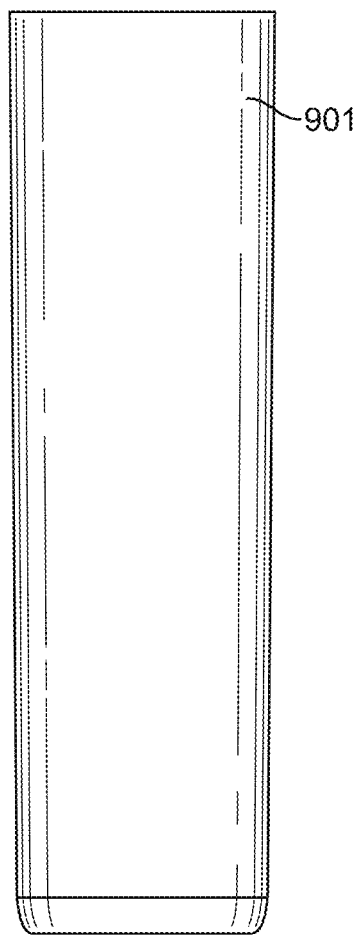
FIG. 30 shows a side view of a cover.

FIG. 30 shows a side view of the cover 901.

Figure 31:
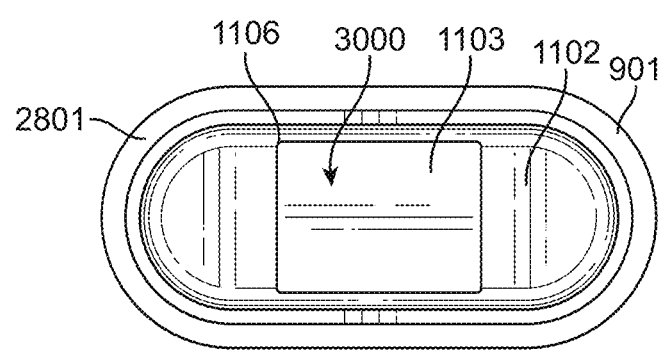
FIG. 31 shows an end view of an open side of a cover.

FIG. 31 shows an end view of the open end 2801 of the cover 901. When looking into the open end the interior surfaces of the cover can be seen. A bottom interior surface (e.g., base) 1102 of the cover can comprise a cavity 3000. The base 1102 can house the reflective material 1103. The reflective material can be adhered to an inner surface of the cover with an adhesive. The base can house the reflective material 1103 in a reflector box 1106 embedded in the base.

Figure 32:
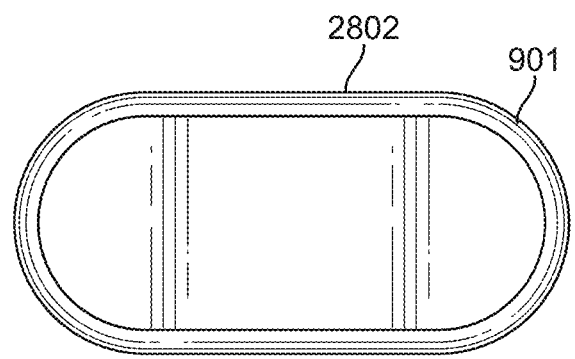
FIG. 32 shows an end view of a closed side of a cover.

FIG. 32 shows an end view of the closed end of the cover 901. The closed end of the cover can comprise a flat surface. The closed end of the cover can comprise a solid surface. The closed end of the cover can comprise a closed surface.

FIG. 32 shows an isometric view of the cover 901.

Figure 33:
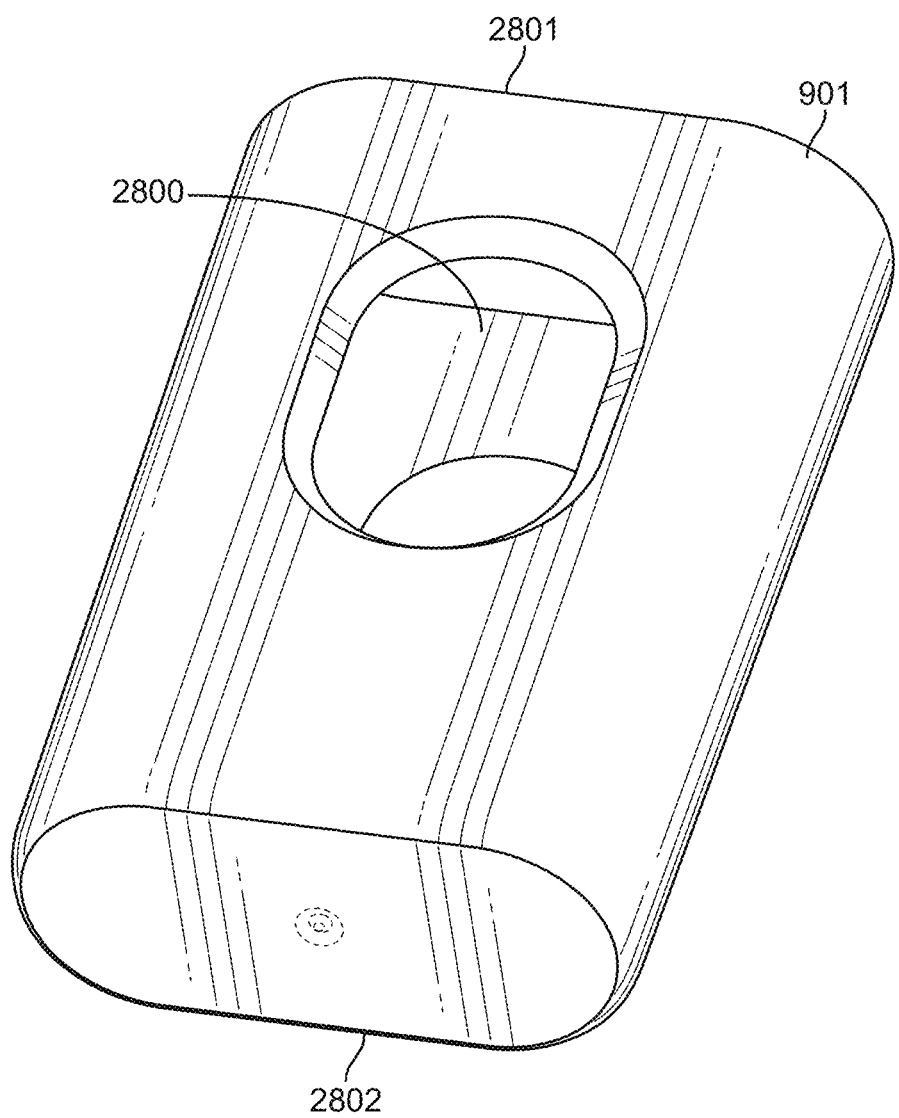
FIG. 33 shows an isometric view of a cover with a closed side of the cover facing a front of the view.
Figure 34:
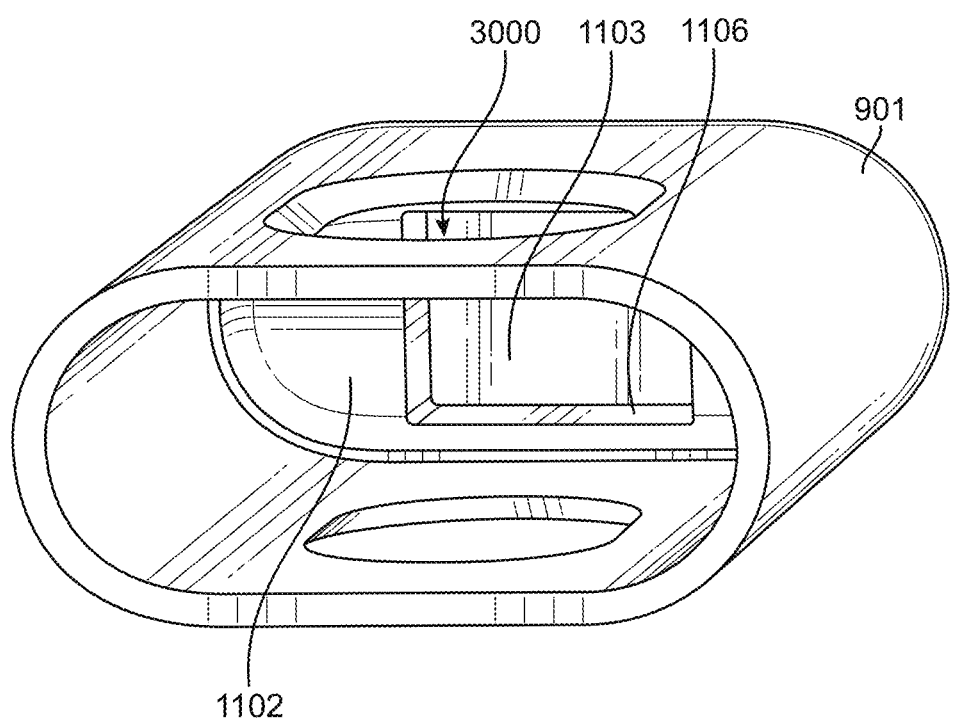
FIG. 34 shows an isometric view of the cover showing a base of the cover.

FIG. 33 shows an isometric view of the cover 901 that shows the interior of the cover including the base 1102.

Figure 35:
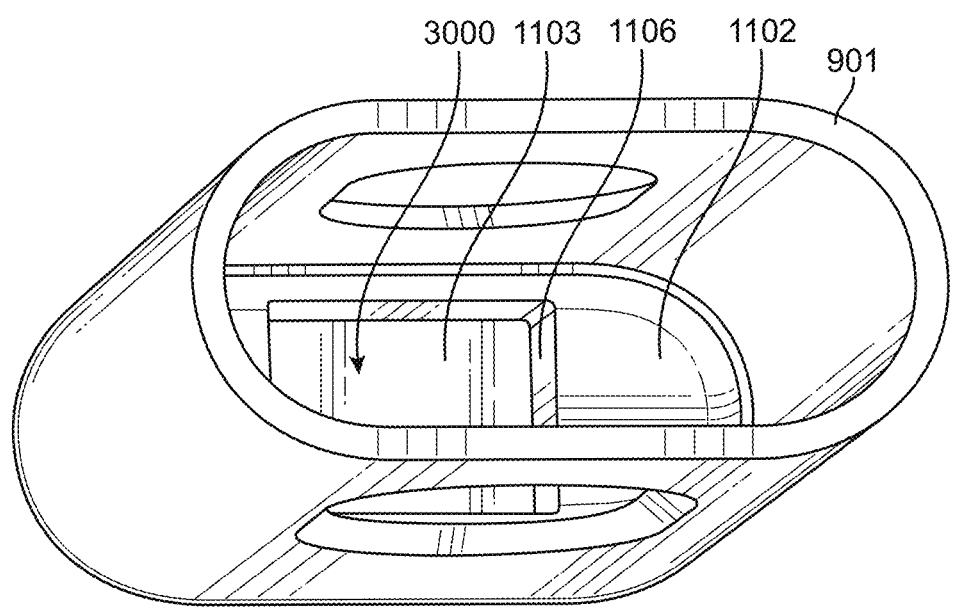
FIG. 35 shows an isometric view of the cover showing a base of the cover with a top right corner of the base visible.

FIG. 35 shows an isometric view of the cover 901 that shows the interior of the cover including the base 1102.

Figure 36:
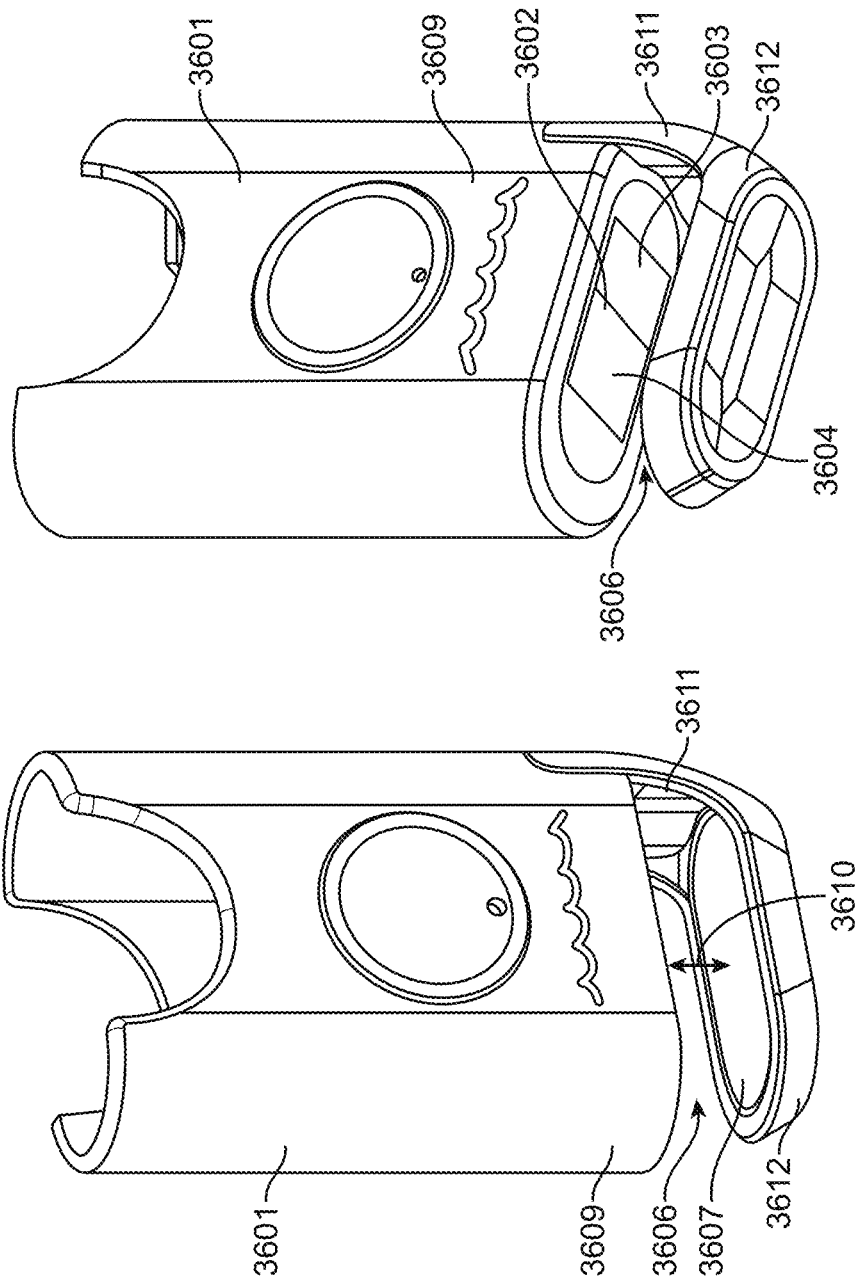
FIGS. 36A and 36B are perspective views of an exemplary accessory configured to facilitate measurement of a liquid sample.

FIGS. 36A and 36B are perspective views of an exemplary liquid measurement accessory 3609 configured to facilitate measurement of a liquid sample. The accessory 3609 comprises a protective cover 3601, wherein the spectrometer may be placed within the protective cover when the accessory is coupled to the spectrometer. The accessory 3609 can comprise a window 3602, similar to window 1902 describe in reference to FIGS. 19A-19B. The window 3602 can be configured to permit transmission of light energy from the illumination module of the spectrometer head. In embodiments wherein the window comprises a material different from the protective cover, the window may be configured to form a liquid-tight seal against the material of the protective cover, such that liquid may be prevented from reaching the spectrometer placed within the protective cover. The window 3602 may comprise a first window 3603 and a second window 3604, wherein the first window and the second window may be optically isolated from each other in order to inhibit interference of signals. The first window 3603 may be arranged adjacent to the illumination window 142 (as shown in FIG. 3) of the spectrometer when the spectrometer is coupled to the accessory, such that light from the illumination module can be transmitted through the illumination window and the first window 3603 to the liquid sample. The second window 3604 may be arranged adjacent to the spectrometer window 162 (as shown in FIG. 3) of the spectrometer when the spectrometer is coupled to the accessory, such that light from the liquid sample can be transmitted through the second window 3604 and the spectrometer window to the detector of the spectrometer. Many aspects of the window 3602, first window 3603, and second window 3604 may be similar to aspects of the window 1902, first window 1903, second window 1904, or third window 1905 described in reference to FIGS. 19A-19B.

The accessory 3609 can further comprise a platform or base 3612 coupled to the protective cover 3601, wherein the base supports a reflective element 3607. The reflective element 3607 may be similar in many aspects to reflective element 1907 described in reference to FIGS. 19A-19B. For example, the reflective element 3607 may comprise a material that is a diffuse reflector, and may be embedded in the base 3612 with or without a protective layer provided over the reflective element. The base may be coupled to the protective cover with an arm or post 3611 configured to place the reflective element at a predetermined measurement distance 3610 from the window 3602. Alternatively, the base may be coupled to the protective cover with two or more arms or posts. When the spectrometer coupled to the accessory is partially dipped or immersed in a liquid sample for measurement of the sample, the liquid sample can fill a space 3606 between the end of the protective cover 3601 comprising the window 3602 and the reflective element 3607. Illumination from the illumination module can illuminate the volume of the liquid sample filling the space 3606. The reflective element can increase the amount and/or intensity of light reflected back towards the spectrometer, thereby helping to increase the accuracy of measurement. The distance 3610 can be configured to be similar in many aspects to the distance 1910 described in reference to FIGS. 19B.

The protective cover 3601 of the accessory 3609 may further comprise a liquid level indicator 3614. The liquid level indicator may be configured to indicate an ideal liquid height on the protective cover as the handheld spectrometer coupled to the liquid measurement accessory is dipped or immersed in the liquid sample. As a user begins to immerse the spectrometer/liquid accessory assembly into the liquid sample and the liquid level on the protective cover rises, the user may use the liquid level indicator as a visual guide for determining when to stop lowering the spectrometer assembly further down in the liquid sample.

The protective cover 3601 may further comprise a movable portion 3616, configured to allow access to an operation mechanism of the handheld spectrometer (e.g., operating button 1006 shown in FIG. 10) when the handheld spectrometer is placed within the protective cover. The movable portion may be positioned so as to be aligned with the operation mechanism of the spectrometer when the spectrometer is placed within the protective cover. The movable portion may, for example, comprise a soft, flexible material that can deform in response to pressure, to allow operation of the operation mechanism positioned beneath the movable portion. The movable portion is preferably configured to form a liquid-tight seal against the protective cover about the periphery of the movable portion, to prevent liquid from permeating the boundary of the movable portion and thereby prevent liquid from directly contacting the handheld spectrometer.

The accuracy of measurements by a spectrometer as described herein may be affected by various elements of the spectrometer, such as the illumination source, light guiding elements, reflective elements, or detecting elements, or by various accessories of the spectrometer used for sample measurement. Even relatively small differences between spectrometer systems can be important, particularly when spectral data generated by a plurality of similar spectrometer systems are compared. To reduce the variations in measured sample spectra due to differences in various spectrometer system components, each spectrometer and/or each accessory of the spectrometer may be calibrated during production of the devices. Also, each spectrometer and/or each accessory may be assigned a corresponding identification, such as a unique identifier, at the production site. The calibration spectra of each device may be digitally associated with the unique identifier of the device and stored in a database, such as a database stored on a computing device configured to analyze sample measurement data. When a user measures a sample material, the user may also take one or more calibration measurements of one or more accessories of the spectrometer system. The calibration data for each accessory and the unique identifier of the accessory may be transmitted to a processing unit along with the sample measurement data and the unique identifier of the spectrometer. The processing unit may then generate the sample spectra in response to the sample measurement data, the unique identifier of the spectrometer, the calibration data, and the unique identifier of the accessory. Such a calibration process can account for variations among spectrometer system components, thus generating more accurate and consistent sample spectra.

Figure 37:
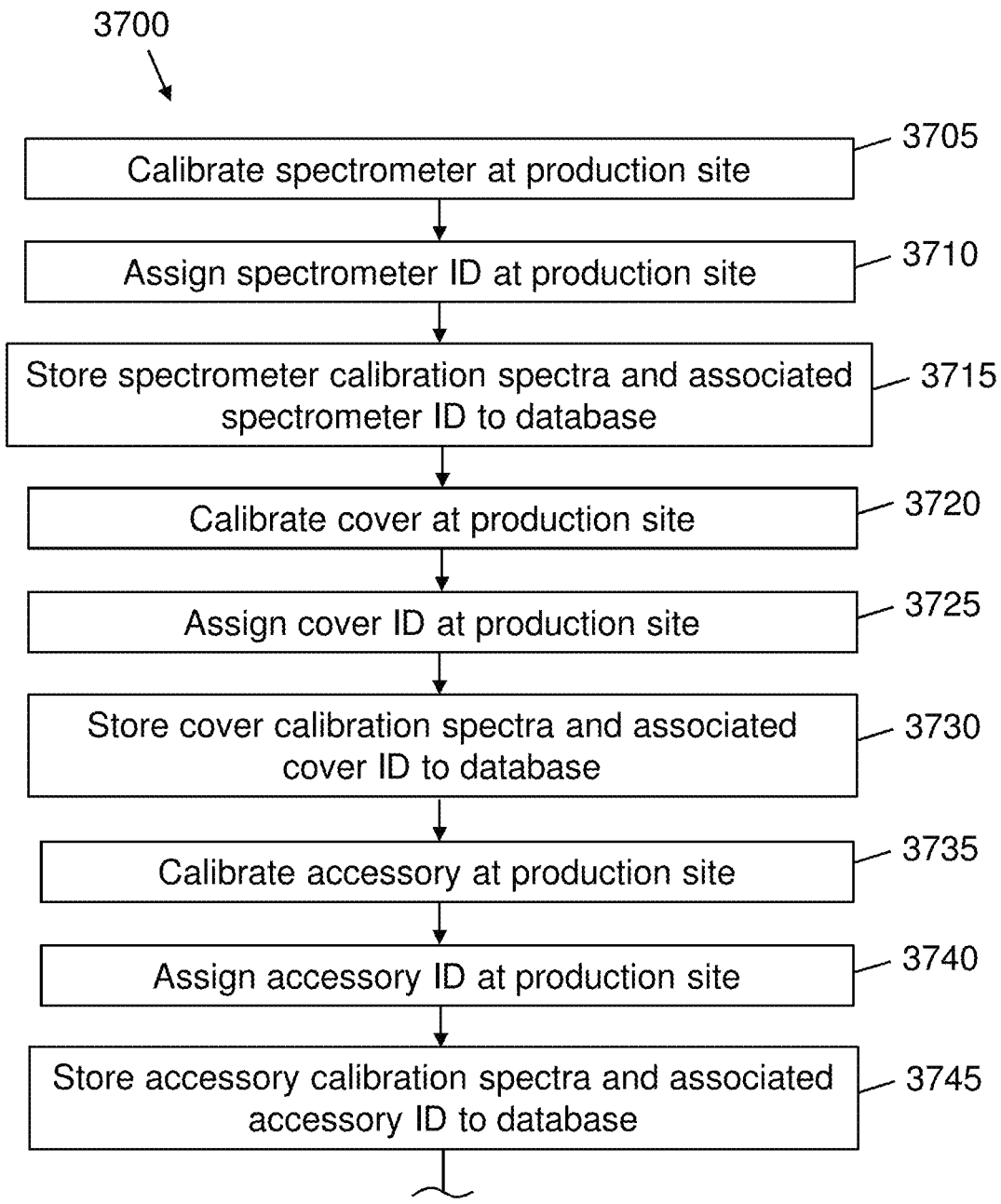
FIG. 37 shows a method for a calibration procedure to improve the accuracy of sample measurements taken with a spectrometer system as described herein.
Figure 37:
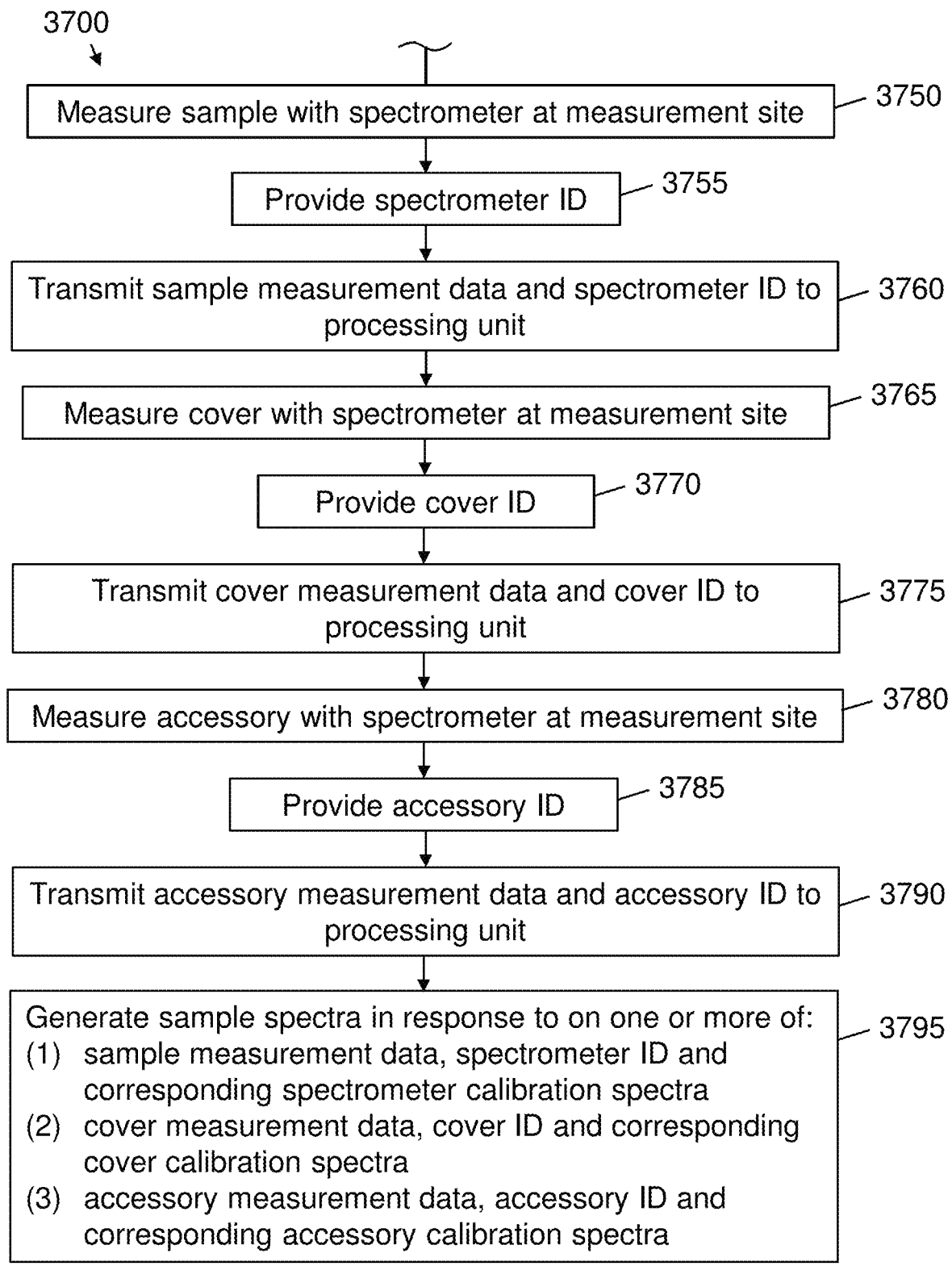

FIG. 37 shows a method 3700 for a calibration procedure to improve the accuracy of sample measurements taken with a spectrometer system as described herein.

In step 3705, a handheld spectrometer may be calibrated at a production site. For example, one or more reference materials with known spectral responses at one or more given wavelengths may be measured with the handheld spectrometer to generate spectrometer calibration spectra.

In step 3710, a spectrometer identifier (ID) may be assigned to the handheld spectrometer at the production site. The spectrometer ID may comprise a unique identifier such as an alphanumeric serial code, a barcode, a Quick Response (QR) code, a 2D code, magnetic code, or any other type of unique identifier capable of identifying the handheld spectrometer. The spectrometer ID may be physically displayed on the spectrometer (e.g., printed, engraved, embossed, debossed, labeled, etc. on the housing or body of the spectrometer), and/or may be integrated into the spectrometer (e.g., magnetically embedded in the housing or body of the spectrometer, electronically embedded in a processing unit of the spectrometer, etc.).

In step 3715, the spectrometer calibration spectra of a given handheld spectrometer and the spectrometer ID of said handheld spectrometer may be stored to a database. The spectrometer calibration spectra may be digitally coupled to the corresponding spectrometer ID, such that each spectrometer calibration spectrum stored in the database is correlated to a spectrometer ID. The database may be stored in a local or remote processing unit configured to perform analysis of spectral data produced by the handheld spectrometer. For example, as described herein in reference to FIG. 2, a spectrometer 102 and/or a handheld computing device 110 may be in wireless communication 116 with a cloud-based storage system or server 118, and the cover spectral response may be stored in a database stored on the server 118. Alternatively or in combination, the database may be stored on a processor 106 of the spectrometer 102 or on a processor of the handheld computing device 110.

In step 3720, a cover of a handheld spectrometer may be calibrated at a production site. For example, a reference material provided with the cover may be measured with a reference spectrometer to generate the cover calibration spectra.

In step 3725, a cover ID may be assigned to cover at the production site. The cover ID may comprise any unique identifier as described in reference to the spectrometer ID. The cover ID may be physically displayed on the cover (e.g., printed, engraved, embossed, debossed, labeled, etc.), and/or may be integrated into the cover (e.g., magnetically embedded, electronically embedded, etc.). The cover ID may comprise the same or a different type of unique identifier as the spectrometer ID.

In step 3730, the cover calibration spectra of a given cover and the cover ID of said cover may be stored to a database, which may be the same database as described in reference to step 3715, or a similar database. The cover calibration spectra may be digitally coupled to the corresponding cover ID, such that each cover calibration spectrum stored in the database is correlated to a cover ID.

In step 3735, an accessory of a handheld spectrometer may be calibrated at a production site. For example, a reference material provided with the accessory may be measured with a reference spectrometer to generate the accessory calibration spectra.

In step 3740, an accessory ID may be assigned to accessory at the production site. The accessory ID may comprise any unique identifier as described in reference to the spectrometer ID. The accessory ID may be physically displayed on the cover (e.g., printed, engraved, embossed, debossed, labeled, etc.), and/or may be integrated into the cover (e.g., magnetically embedded, electronically embedded, etc.). The accessory ID may comprise the same or a different type of unique identifier as the spectrometer ID or the cover ID.

In step 3745, the accessory calibration spectra of a given accessory and the accessory ID of said accessory may be stored to a database, which may be the same database as described in reference to step 3715, or a similar database. The accessory calibration spectra may be digitally coupled to the corresponding accessory ID, such that each accessory calibration spectrum stored in the database is correlated to an accessory ID.

In step 3750, a sample may be measured with the handheld spectrometer at a measurement site to generate sample measurement data. For example, the spectrometer may be placed in a cover in the measurement orientation and used to measure a sample surface, the spectrometer may be coupled to a sample container and used to measure a sample received within the sample container, or the spectrometer may be coupled to a liquid measurement accessory and used to measure a liquid sample while partially immersed in the liquid sample.

In step 3755, the spectrometer ID of the handheld spectrometer used in step 3750 may be provided to a local processing unit in communication with the handheld spectrometer. For example, the spectrometer ID may be embedded in a chip in or on the spectrometer, and read through electrical contacts (e.g., I$^2$C or SPI communication) or through wireless communication systems (e.g., near-field communication, radio frequency identification, Bluetooth, WiFi, etc.). Alternatively or in combination, the user may provide the spectrometer ID to the local processing unit, for example by manually entering the ID comprising a serial number, scanning a barcode or QR code with an optical scanner, etc.

In step 3760, the sample measurement data generated in step 3750 and the spectrometer ID obtained in step 3755 may be transmitted to a processing unit configured to generate the sample spectra. The processing unit may comprise a local or a remote processing unit, and data may be transmitted to said processing unit via a wired or wireless connection.

In step 3765, a cover may be measured with the handheld spectrometer at a measurement site to generate cover measurement data. For example, the spectrometer may be placed in the cover in the calibration orientation, and used to measure the calibration material provided near the closed end of the cover. In many instances, this calibration measurement is made shortly before or after the sample measurement, in order to ensure temporal proximity of the calibration measurement to the sample measurement and thereby account for variations of the spectrometer system over time.

In step 3770, the cover ID of the cover measured in step 3765 may be provided to a local processing unit in communication with the handheld spectrometer, in any of the ways described in reference to step 3755 for providing the spectrometer ID.

In step 3775, the cover measurement data generated in step 3765 and the cover ID obtained in step 3770 may be transmitted to a processing unit configured to generate the sample spectra, as described in reference to step 3760.

In step 3780, an accessory may be measured with the handheld spectrometer at a measurement site to generate accessory measurement data. For example, the spectrometer may be coupled to a sample container or a liquid measurement accessory as described herein, and the spectrometer may be used to measure a reference material provided in or on the accessory. In many instances, this calibration measurement is made shortly before or after the sample measurement, in order to ensure temporal proximity of the calibration measurement to the sample measurement and thereby account for variations of the spectrometer system over time.

In step 3785, the accessory ID of the accessory measured in step 3780 may be provided to a local processing unit in communication with the handheld spectrometer, in any of the ways described in reference to step 3755 for providing the spectrometer ID.

In step 3790, the accessory measurement data generated in step 3780 and the accessory ID obtained in step 3785 may be transmitted to a processing unit configured to generate the sample spectra, as described in reference to step 3760.

In step 3795, the processing unit may generate the sample spectra in response to one or more of: (1) the sample measurement data, spectrometer ID, and the corresponding spectrometer calibration spectra stored on the database; (2) the cover measurement data, cover ID, and the corresponding cover calibration spectra stored on the database; and (3) the accessory measurement data, the accessory ID, and the corresponding accessory calibration spectra stored on the database. Generation of the sample spectra can thus take into account the spectral response of the specific cover or accessory used to calibrate the spectrometer and the spectral response of the spectrometer system at the time of measurement of the sample, thereby compensating for the variation among the spectral response of different spectrometer system components, and improving the accuracy and reliability of the generated sample spectra.

The steps of method 3700 are provided as an example of improving the accuracy of sample measurements by a spectrometer using a calibration procedure. A person of ordinary skill in the art will recognize many variations and modifications of method 3700 based on the disclosure provided herein. For example, some steps may be added or removed. Some of the steps may comprise sub-steps. Many of the steps may be repeated as many times as appropriate or necessary. One or more steps may be performed in a different order than as illustrated in FIG. 37.

In some embodiments the spectrometer may be coupled to a sample container, for example a tube or a pipette (e.g., a disposable pipette), or any other type of advanced liquid measurement accessory as described herein to measure the reflectance or trans-reflectance spectrum of liquids. The advanced liquid accessory, may be mounted possibly but not exclusively as an add-on on the spectrometer, eliminating the direct contact between the measured liquid and the spectrometer. As a result there is no need to clean the spectrometer between consecutive measurements.

The advanced liquid measurement accessory can be configured to be inserted into a container configured to hold the sample. The container can have larger dimensions, such as a barrel. The advanced liquid measurement accessory can enable swift and convenient access to the container content (e.g. sample liquid). The advanced liquid measurement accessory can be configured to be inserted into the container to retrieve liquid sample from the container and to retain the liquid sample therewithin, and to be coupled to the spectrometer to allow measurement of the liquid sample by the spectrometer while retaining the liquid sample within the advanced liquid measurement accessory.

Figure 38A:
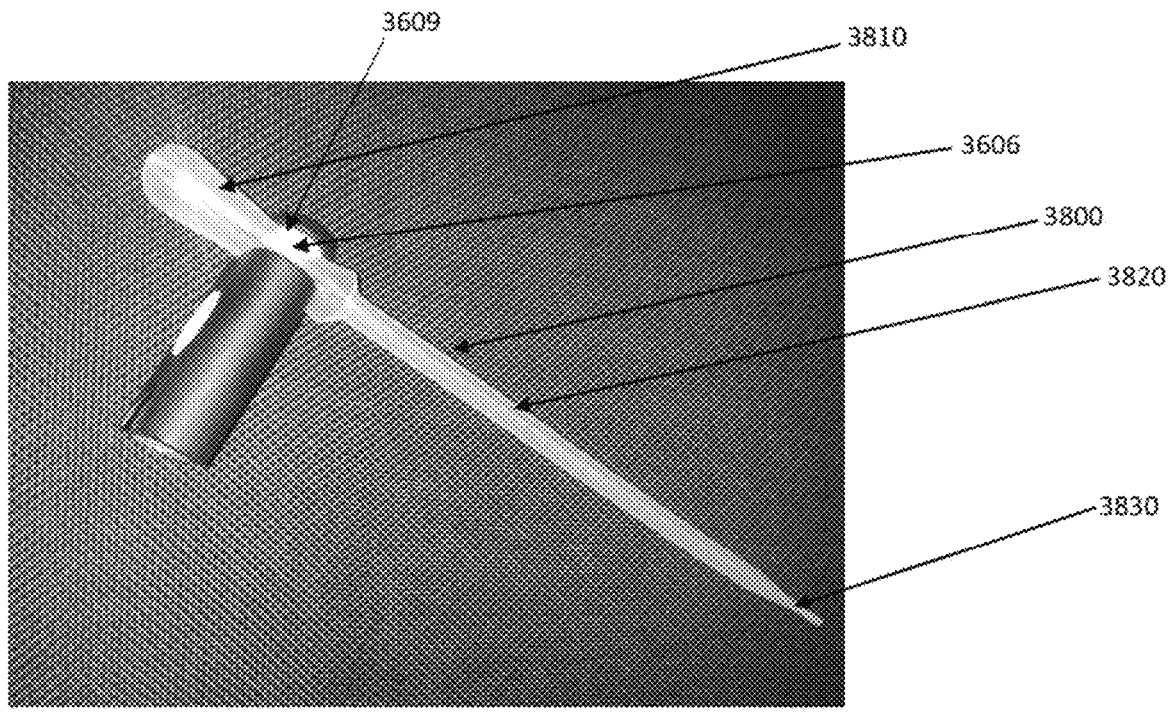
FIGS. 38A-38C shows an advanced accessory and an extension device.
Figure 38B:
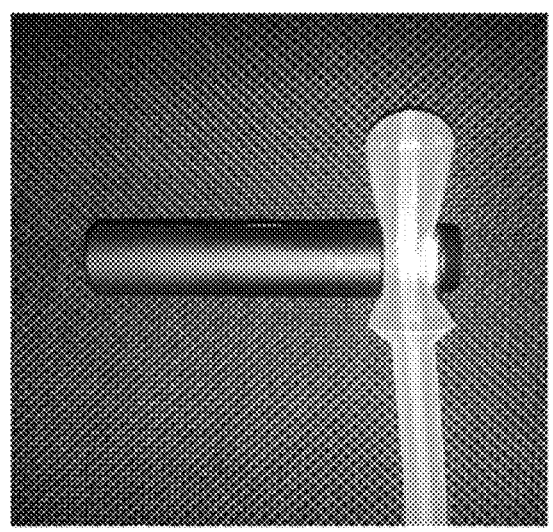
Figure 38C:

FIGS. 38A-38C show a perspective views of advanced liquid accessory in the form of a disposable pipette 3800 coupled to the accessory 3609. A portion of the disposable pipette 3800 containing a sample can be positioned in the space 3606 to couple the disposable pipette 3800 to the accessory 3609 such that the disposable pipette 3800 can be positioned relative to a spectrometer coupled to the accessory 3609 to enable measurement of liquid sample retained within the disposable pipette 3800. The disposable pipette 3800 can comprise a bulb portion 3810, a stem portion 3820 extending from the bulb portion 3810 and a tip 3830 at an end of the bulb portion 3810 distal from the bulb portion 3810. A liquid sample can be pulled into the disposable pipette 3800 via the tip 3830 such that the liquid sample can be transported through the stem portion 3820 and into the bulb portion 3810. At least a portion of the bulb portion 3810 can be positioned in the space 3606 such that the liquid sample retained within the bulb portion 3810 can be analyzed by a spectrometer coupled to the accessory 3609. The liquid sample within the bulb portion 3810 can be positioned relative to the accessory 3609 such that the liquid sample can be illuminated by the illumination module of the spectrometer and reflectance and/or trans-reflectance from the liquid sample can be measured by the spectrometer module. In some cases the bulb portion 3810 of the pipette 3800 may be squeezed in the space 3606 of the accessory 3609. Squeezing the bulb portion 3810 in the space 3609 can reduce or eliminate the interference of reflections from the pipette walls to the spectrum measurement.

In some cases, the illumination module and spectrometer modules of the spectrometer are separated by an opaque separation, preferably a black wall, in order to reduce or eliminate the amount of light from the illumination module to enter the spectrometer module without passing through the fluid in the disposable pipette 3800.

Figure 44A:
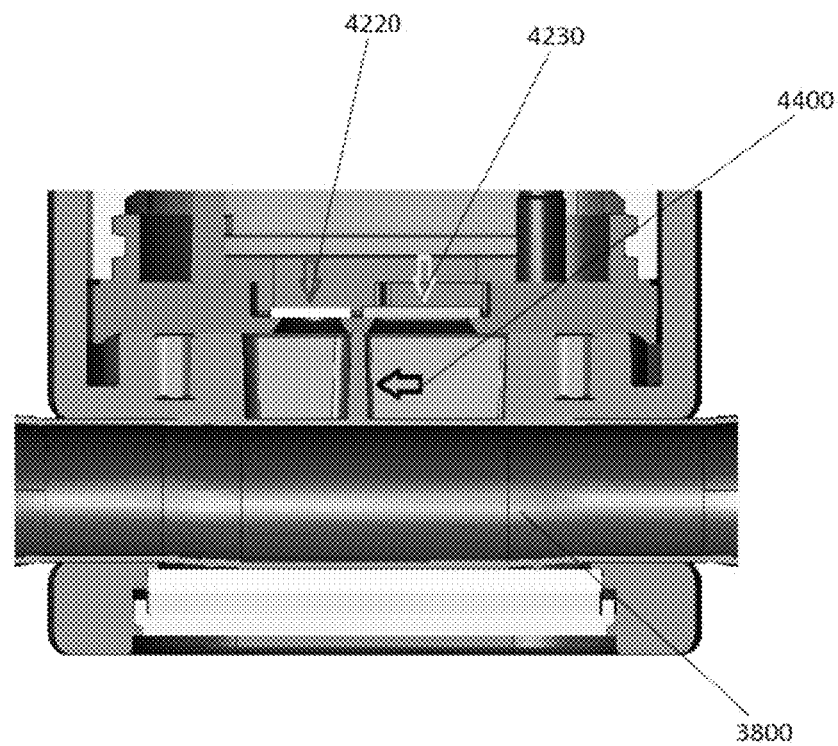
FIG. 44A shows a first cross section view of a spectrometer comprising a disposable pipette as described with reference to FIGS. 38A-38C.
Figure 44B:
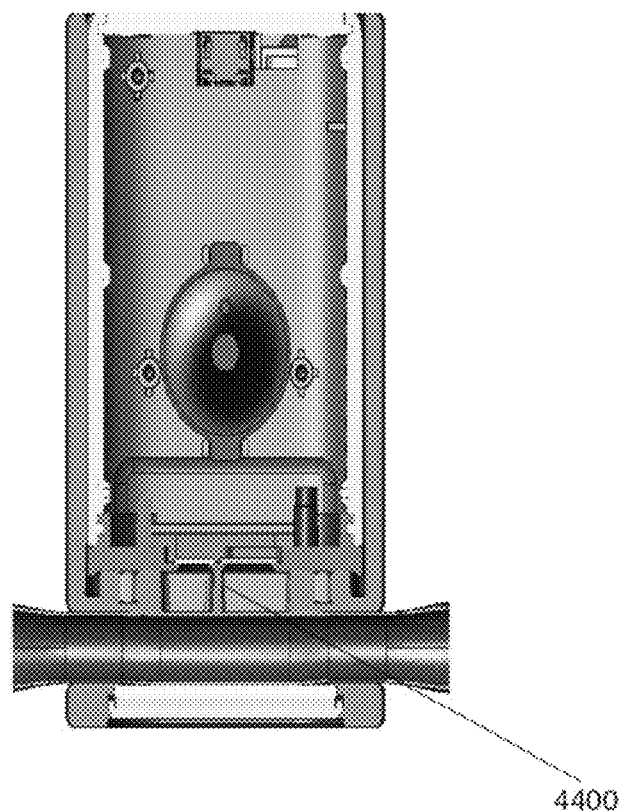
FIG. 44B shows a second cross section view of a spectrometer comprising a disposable pipette as described with reference to FIGS. 38A-38C.

FIGS. 44A and 44B are cross section views of a spectrometer comprising the disposable pipette 3800 as described with reference to FIGS. 38A-38C in accordance with embodiments. The spectrometer comprises a black wall 4400 configured and enabled to separate between the illumination exiting for example from the illumination module 4220 and the spectrometer module 4230. According to some configuration the black wall may be made of plastic or other opaque material configured to reduce or eliminate the amount of light from the illumination module to enter the spectrometer module.

Figure 39:
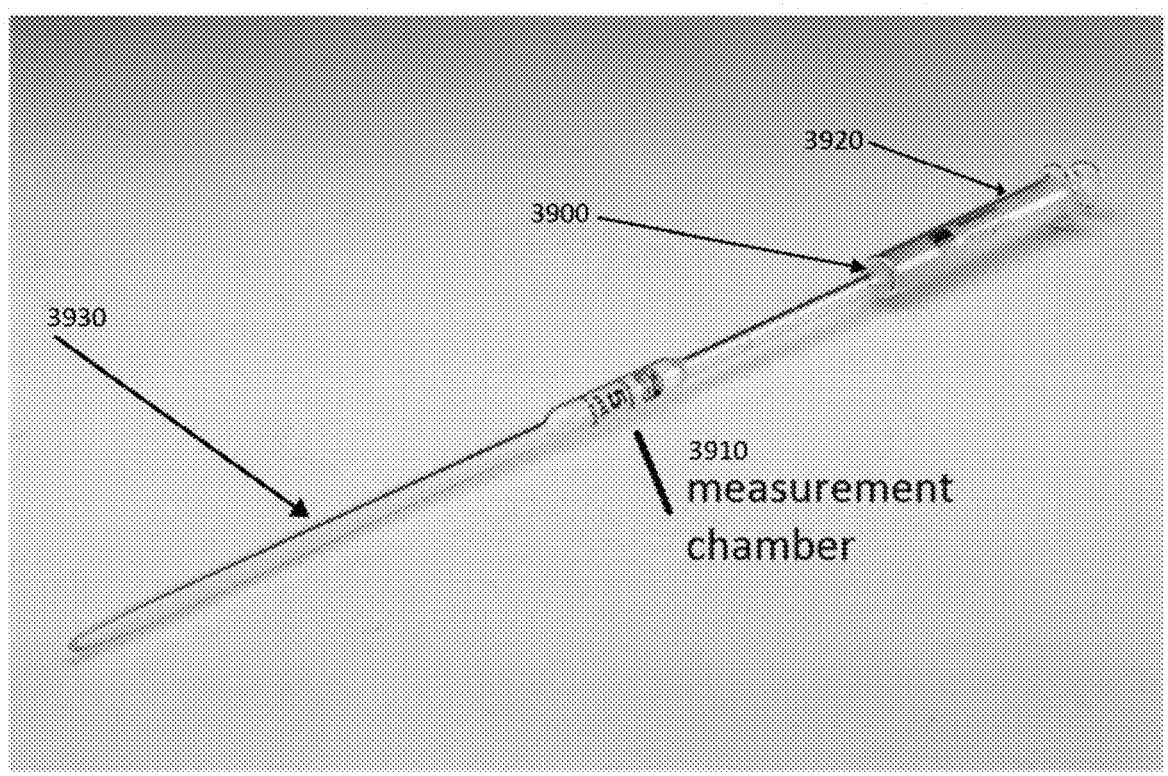

FIG. 39 shows an advanced liquid accessory 3900 comprising an injection unit for example a syringe or a cylinder or piston mechanism 3920 at the top end of the pipette 3930 to enable convenient suction of liquid into a measurement chamber part 3910.

In some cases, the spectrometer module and/or the illumination module of the spectrometer may be positioned relative to the measurement chamber part 3910 located for example at the center of pipette 3930 to enable measurement of liquid sample within the measurement chamber part 3910. For example, the measurement chamber 3910 may be coupled to a spectrometer such that an illumination module and a spectrometer module of the spectrometer can be in optical communication with the measurement chamber 3910 to allow measurement of a liquid sample within the measurement sample 3910.

In some cases, at least a portion of the liquid accessory 3900 can be positioned in the space 3606 of the accessory 3609 to facilitate measurement of the liquid sample within the liquid accessory 3900 by a spectrometer coupled to the accessory 3609. For example, at least a portion of the measurement chamber part 3910 may be positioned in the space 3606 of the accessory 3609 such that the illumination module and spectrometer module of the spectrometer coupled to the accessory 3609 can be in optical communication with the liquid within the measurement chamber part 3910.

According to some embodiments the syringe may be made of a material such as plastics.

In some embodiments, the syringe and/or the pipette may be disposable.

In some embodiments the syringe and/or the pipette may be recycled and configured for multiple use by a user.

Figure 40:
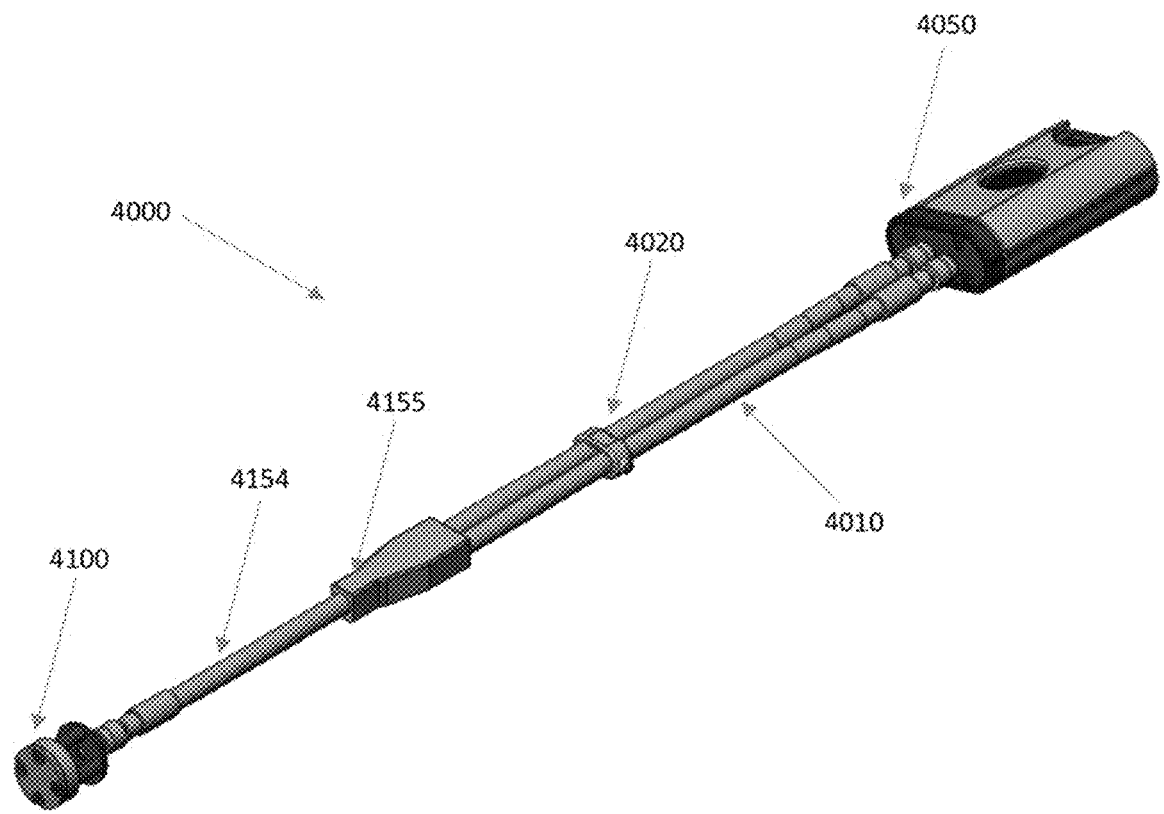

FIG. 40 shows an extension device 4000 configured to be attached to a spectrometer 4050, in accordance with embodiments. The extension device 4000 may be used in cases where the liquid is not easily accessible but cleaning is permitted. The extension device 4000 may comprise or may be attached at one end to the spectrometer 4050 and at a second end to a measurement element such as a measurement container or measurement cup 4100. The measurement cup 4100 can be positioned at least partially into a liquid sample to allow measurement of the liquid sample by the spectrometer 4050. The measurement cup 4100 is configured with a plurality of units for sensing liquid and may be easily inserted into the liquid. The spectrometer 4050 may comprise one or more features of the spectrometers as described herein, such as the spectrometer of FIG. 1-15. Using the extension device 4000 can advantageously allow positioning of the spectrometer outside of a liquid container while measurement of the liquid is performed. The extension device 4000 may further include one or more optical fiber bundles, for example a first bundle 4010 and a second bundle 4020 connected at one end to the measurement cup 4100. The extension device 4050 may include a combiner 4155 to combine the first and second bundles 4010, 4020 to a single optical fiber element 4154 before the single optical element 4154 is delivered into the measurement cup 4100. The optical fiber bundles 4010, 4020 can be configured to provide optical communication between the spectrometer module and the illumination module of the spectrometer 4050, and the liquid sample into which the measurement cup 4100 is positioned. For example, the first optical bundle 4010 can couple the spectrometer module to the measurement cup 4100 while the second optical bundle 4020 can couple the illumination module to the measurement cup 4100. At least a portion of the optical fiber bundles 4010, 4020 can be optically isolated from one another such that light transmitted within the respective portions of the optical fiber bundles 4010, 4020 do not cross-communicate. In some cases, at least a portion of each of the first optical fiber bundle 4010 the second optical fiber bundle 4020 and the single optical fiber 4154 can be housed within respective opaque housing members to facilitate reduced or eliminate cross-communication between light transmitted by the optical fiber bundles 4010, 4020 or the single optical fiber element 4154.

In some embodiment, a single or more than two optical fibers (or fiber bundles) may be used.

In some embodiments the first fiber 4010 may be optically coupled to the illumination module of the spectrometer 4050 on one end and to the measurement cup 4100 on the other end. The second fiber 4020 may be optically coupled to the spectrometer module of the spectrometer 4050 on one end and to the measurement cup 4200 on the other end.

According to other embodiments the extension device may include a bifurcated fiber bundle. One end of it may be connected to the measurement cup 4100. The fiber bundle may be divided to at least two bundles, where a first bundle is optically coupled to the illumination module of spectrometer and the other is optically coupled to the spectrometer module.

Figure 41:
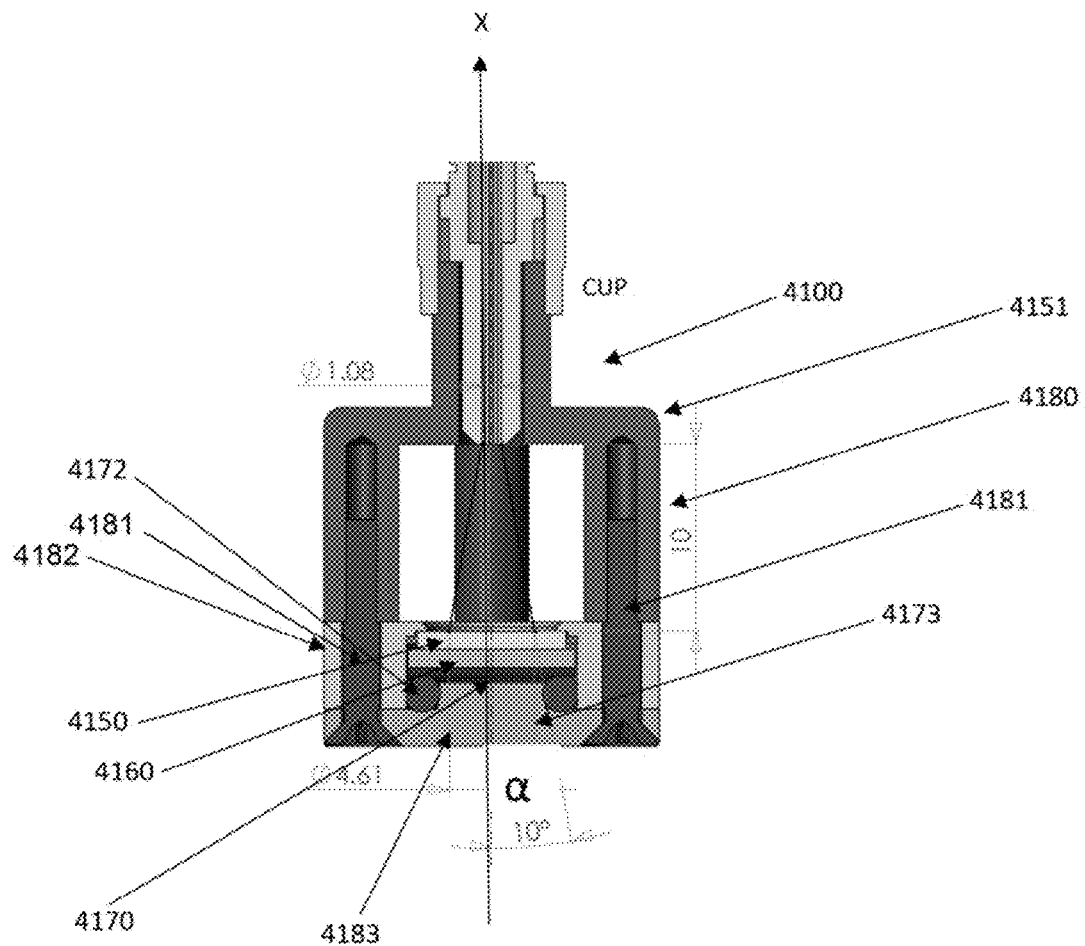

FIG. 41 shows the measurement cup 4100 units as described with reference to FIG. 40 in accordance with embodiments. The cup comprises a window 4150 placed on a reflector 4160. The reflector is placed on an opaque element 4170. As described herein, the measurement cup 4100 is configured with a plurality of units for sensing liquid and may be easily inserted into the liquid.

According to some embodiments the cup 4100 comprises a main carrier or holder unit 4180 configured to hold the reflector 4160 in a predetermined constant distance from the optical fiber. The holder 4180 may comprise a plurality of shafts for example four shafts 4151 connected via a plurality of connectors such as screws 4181 to a carrier unit 4182. The carrier unit 4182 is configured to hold the window 4150, the reflector 4160 and the opaque element. In some cases the carrier unit 4182 may be cylindrical shaped and may be made of metal or other materials. The screws 4181 may be further connected to a plug element 4183 configured to cover and seal elements 4150, 4160 and the opaque element 4170. The plug 4183 may be made of plastic or any other material configured to seal the cup 4100. In some instances, the cup may further comprise one or more sealing elements 4172 such as a single O-ring shaped element located below the opaque element 4170.

In some cases the range of light beam transmitted from the fiber may be $2\alpha$ in respect to an axis X. The angle $\alpha$ may be in a range of about 0-40 degrees, for example 10 degrees. Accordingly the light beam diameter may be in the range of 2 to 20 mm for example 4.61 mm of a fiber having a dimeter of about 1.08 mm and the distance from the fiber edge to the window 4150 may be for example 10 mm.

Figure 42A:
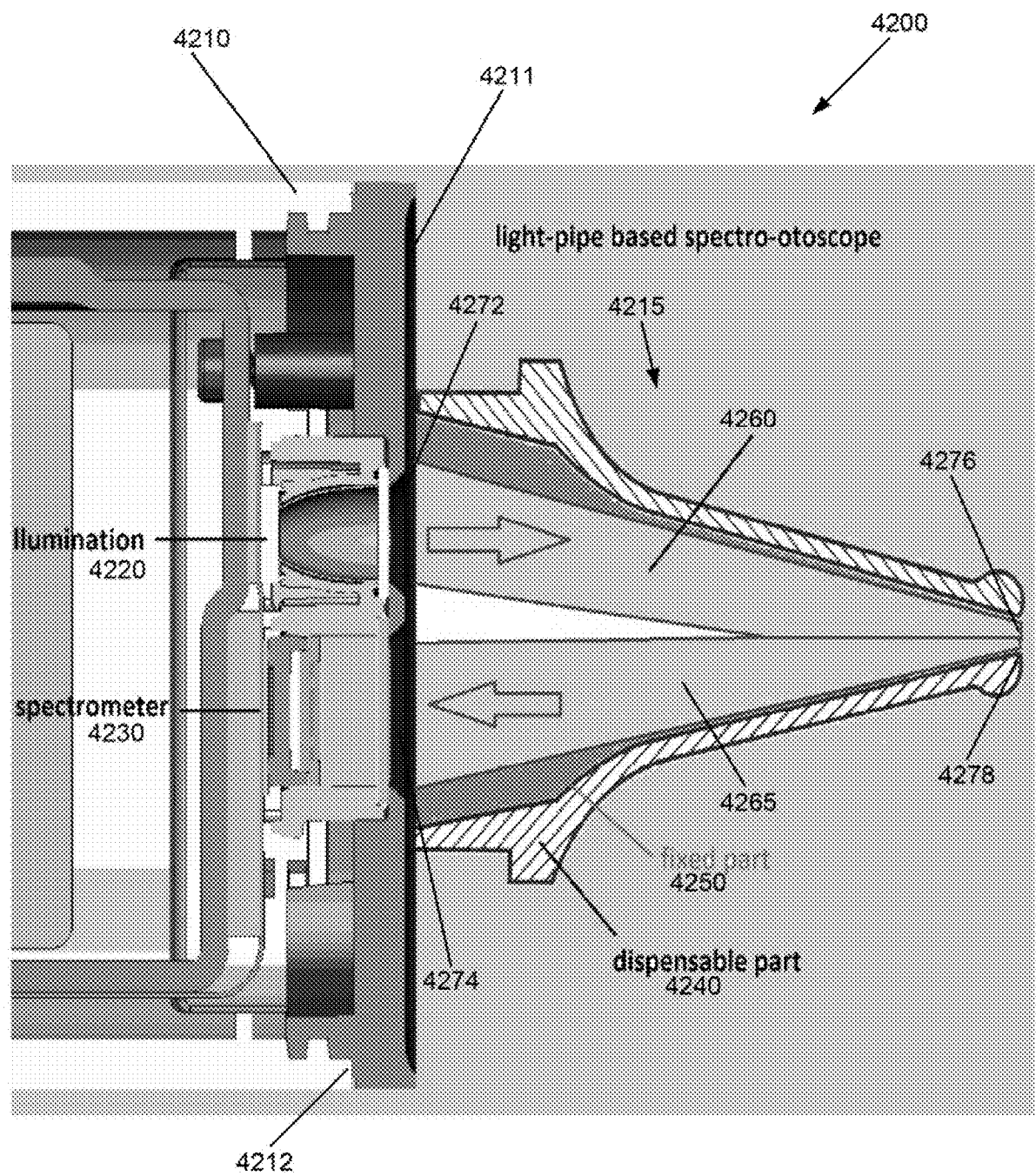
FIG. 42A shows a schematic view of a handheld device coupled to an otoscope accessory component.

FIG. 42A shows a schematic view 4200 of a handheld device 4210 coupled to an otoscope accessory component 4215 in accordance with configurations. The handheld device 4210 can comprise one or more spectrometers as described herein (e.g., FIGS. 1-15). The handheld device 4210 comprises a housing member 4212 for covering a spectrometer module 4230 and an illumination 4220 module of the handheld device 4210. The handheld device 4210 is configured and enabled to be coupled to an accessory 4215 by one or more adaptors such as fixed parts 4250. The accessory 4215 may form a part of a spectro-otoscope. The otoscope accessory component 4215 may comprise an otoscope cover 4240 configured to be inserted to the ear of a subject. The otoscope cover 4240 may have a tapered profile, for example having a cone shape, to facilitate insertion into the ear. The otoscope cover 4240 may be disposable. The otoscope cover 4240 may be positioned over inner fixed parts 4250 which may not be disposable. The otoscope cover 4240 can be configured to provide an external barrier for the entirety of the inner fixed parts 4250 such that the inner fixed parts 4250 can remain sterile while the otoscope cover 4240 contacts a subject. In some cases, the otoscope cover 4240 may be configured to not be reusable such that a different cover 4240 is used for each subject or ear. The otoscope cover 4240 can preferably be dispensable. The otoscope cover 4240 may be made of plastic or other material. The otoscope cover 4240 can be configured to be removably coupled to the inner fixed parts 4250 such that the otoscope cover 4240 is changed between subjects and/or ears, while the inner fixed parts 4250 can be reused, thereby reducing components which need to be sterilized and/or dispensed for examination of the different subjects and/or ears. The inner fixed parts 4250 can be changed at a lower frequency than the otoscope cover 4240.

The one or more inner fixed parts 4250 may be more permanently attached or coupled to the handheld device 4210, such as via a handheld device cover 4211. The inner fixed parts 4250 can be coupled to the spectrometer to facilitate positioning the otoscope cover 4240 at a desired position relative to the handheld device 4210. As described herein, the handheld device 4210 can comprise a spectrometer. The otoscope cover 4240 can be positioned relative to the spectrometer such that the spectrometer module 4230 and the illumination module 4220 can be in optical communication with the inside of a subject's ear when at least a portion of the otoscope accessory unit 4215 is positioned within the subject's ear. In some cases, the otoscope accessory unit 4215 may comprise a first light pipe 4260 and a second light pipe 4265 for guiding light accordingly from the illumination module 4220 to the ear, such as the ear drum or another portion of the ear, and back to the spectrometer module 4230. Preferably the otoscope accessory unit 4215 is placed in front of the spectrometer head, covering the illumination module 4220 and the spectrometer module 4230. In some cases, however, the otoscope accessory unit 4215 may be located or connected to other units of the handheld device 4210 and may be in communication with the illumination module 4220 and the spectrometer module 4230 via the light pipes. The first light pipe 4260 and the second light pipe 4265 may be positioned within the inner fixed parts 4250 such that the light pipes are protected by the inner fixed parts 4250.

In accordance with embodiments the first light pipe 4260 and the second light pipe 4265 are optically isolated from each other to inhibit light from traveling from one pipe to another pipe.

According to some embodiments the light pipe diameter at sections 4272 and 4274 (e.g. the side proximate to the spectrometer and illumination units of the spectrometer) is wider than that of the light pipe distal from the spectrometer and illumination units. For example, the light pipe can be as wide as possible, such as based on dimensions of the inner fixed parts 4250. For example, the diameter of each of the first and second light pipes at sections 4272 and 4274 can be in the range of about 2 to about 6 mm. For example, the diameter of each of the first and second light pipes at sections 4276 and 4278 can be about 1 mm to about 4 mm.

According to some embodiments a window made of for example plastic or glass may be attached to the end of either the fixed parts 4250 or the cover 4240, to avoid the need for sterilizing the fixed elements such as the fixed parts of the device 4200.

Figure 42B:
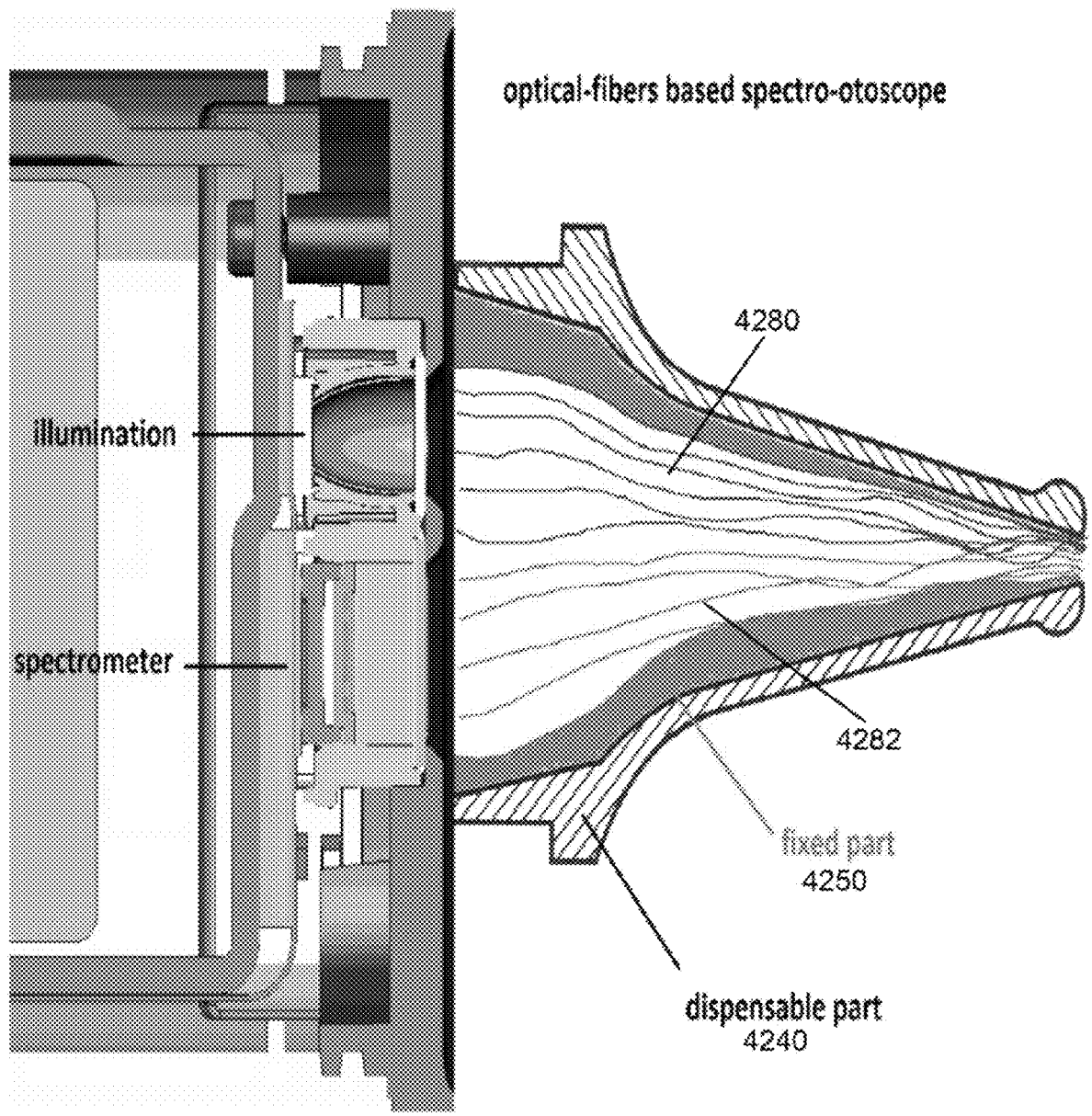
FIG. 42B shows another embodiment of an otoscope accessory unit wherein one or more optical fibers are used for guiding light accordingly from the illumination module to a portion of the ear, such as the ear drum, and back to the spectrometer module.

FIG. 42B shows another embodiment of an otoscope accessory unit 4255 wherein one or more optical fibers 4280 and 4282 are used for guiding light accordingly from the illumination module 4220 to a portion of the ear, such as the ear drum, and back to the spectrometer module 4230.

Figure 43:
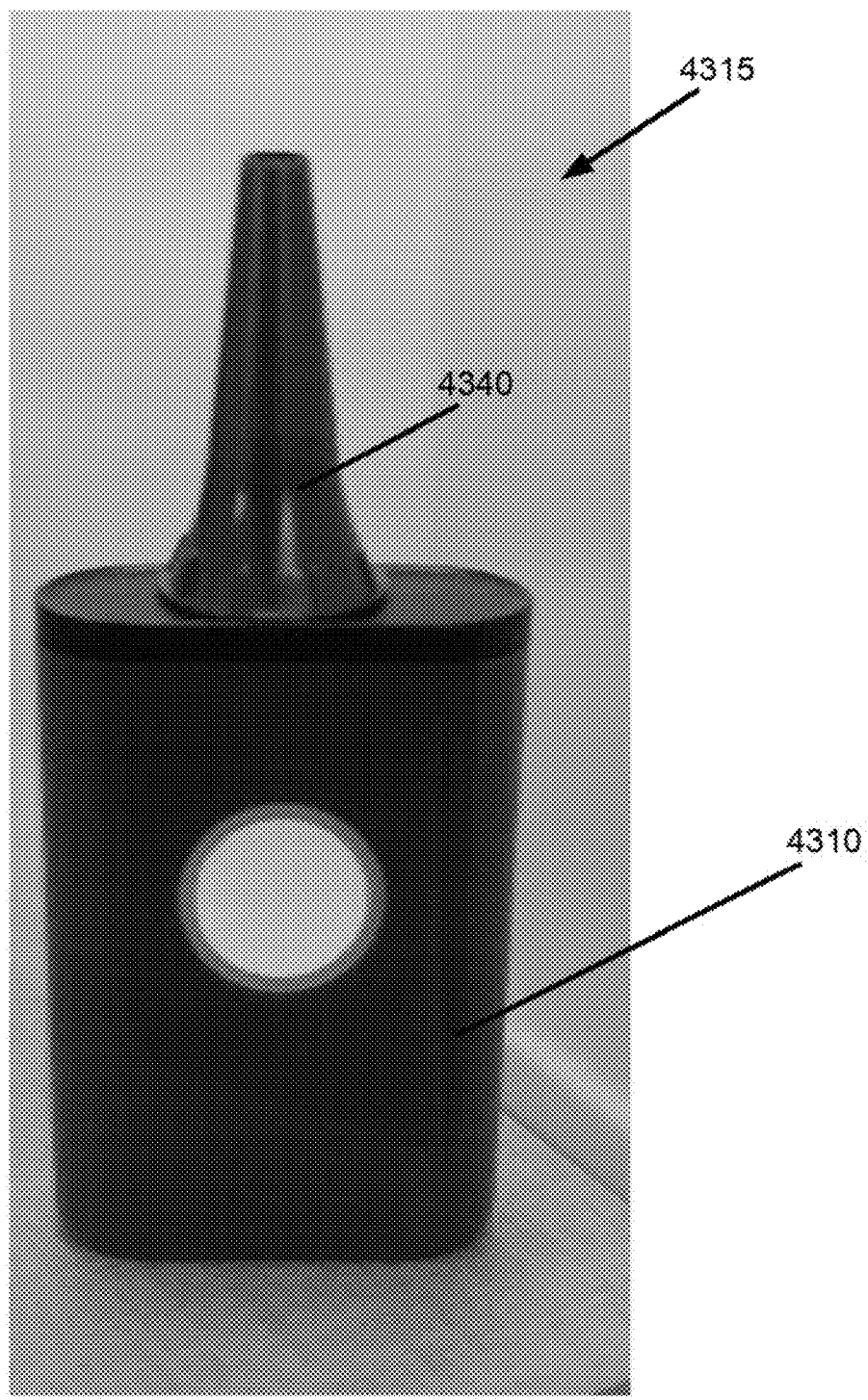

FIG. 43 shows a perspective view of a spectro-otoscope 4315 comprising an otoscope accessory component 4340 coupled to a handheld device 4310, in accordance with embodiments. The handheld device 4310 can comprise a spectrometer such that the inside of a subject's ear can be analyzed using the spectrometer when at least a portion of the otoscope accessory component 4340 is inserted into the ear.

According to some embodiments there is provided a system, device and method for obtaining a spectrum of reflected light from a body lumen of a subject. More specifically there is provided a handheld device configured and enabled to obtain a spectrum of reflected light from an ear. The handheld device may be for example the handheld device or the spectrometer as illustrated in FIGS. 1-10 or any handheld devices configured and enabled to obtain a spectrum of reflected light from an ear.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A system comprising a handheld spectrometer and a liquid measurement accessory for said handheld spectrometer, the liquid measurement accessory comprising a pipette unit comprising an injection unit;
    wherein said injection unit is configured to be inserted into an injection unit receiving recess of the handheld spectrometer to permit the handheld spectrometer to obtain a measurement of a sample contained in the injection unit of the pipette unit, wherein the injection unit is configured to be disposed between optical components of the handheld spectrometer when inserted into said receiving recess; and
    wherein said injection unit is configured to deform upon said insertion into said injection unit receiving recess.

2. The system of claim 1, wherein the injection unit comprises a syringe, a cylinder, or a piston.

3. The system of claim 1, wherein the pipette unit is a disposable pipette.

4. The system of claim 1, wherein the pipette unit is a reusable pipette.

5. The system of claim 1, wherein the injection unit is configured to be in optical communication with the handheld spectrometer.

6. The system of claim 1, wherein the handheld spectrometer comprises a light concentrator disposed between a light source and the injection unit.

7. The system of claim 1, wherein the handheld spectrometer comprises a diffuser.

8. The system of claim 1, wherein the injection unit is configured to provide suction to intake liquid.

* * * * *